United States Patent
Oh et al.

(10) Patent No.: US 9,808,507 B2
(45) Date of Patent: Nov. 7, 2017

(54) ANTI-C-MET/ANTI-ANG2 BISPECIFIC ANTIBODY

(71) Applicant: Samsung Electronics Co., Ltd., Suwon-si, Gyeonggi-do (KR)

(72) Inventors: Seungja Oh, Seoul (KR); Kyung Ah Kim, Seongnam-si (KR); Bo Gyou Kim, Seoul (KR); Seung Hyun Lee, Suwon-si (KR); Ji Min Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/835,376

(22) Filed: Aug. 25, 2015

(65) Prior Publication Data

US 2016/0053025 A1 Feb. 25, 2016

(30) Foreign Application Priority Data

Aug. 25, 2014 (KR) .................. 10-2014-0110868

(51) Int. Cl.
| | | |
|---|---|---|
| *C07K 16/22* | (2006.01) | |
| *A61K 38/18* | (2006.01) | |
| *C07K 16/28* | (2006.01) | |
| *A61K 39/00* | (2006.01) | |

(52) U.S. Cl.
CPC .......... *A61K 38/18* (2013.01); *A61K 38/1891* (2013.01); *C07K 16/22* (2013.01); *C07K 16/2863* (2013.01); *A61K 2039/507* (2013.01); *A61K 2039/545* (2013.01); *C07K 2317/24* (2013.01); *C07K 2317/31* (2013.01); *C07K 2317/622* (2013.01); *C07K 2317/73* (2013.01); *C07K 2317/92* (2013.01)

(58) Field of Classification Search
CPC ............... C07K 16/22; C07K 16/2863; C07K 16/2317; C07K 16/31; C07K 2317/73; A61K 38/18; A61K 38/1891; A61K 2039/507; A61K 2300/00
USPC ................... 424/136.1; 435/69.6; 530/387.3; 536/23.53
See application file for complete search history.

(56) References Cited

U.S. PATENT DOCUMENTS

| | | |
|---|---|---|
| 6,984,389 B2 | 1/2006 | Li |
| 8,029,808 B2 | 10/2011 | Srivastava |
| 8,563,696 B2 | 10/2013 | Cheong et al. |
| 2006/0014204 A1 | 1/2006 | Gale et al. |
| 2011/0097300 A1 | 4/2011 | Van Slyke et al. |
| 2011/0118298 A1 | 5/2011 | Fritz et al. |
| 2012/0064175 A1 | 3/2012 | Vukovic et al. |
| 2013/0023420 A1 | 1/2013 | Thomas et al. |
| 2013/0259868 A1 | 10/2013 | Roschke et al. |
| 2014/0378664 A1* | 12/2014 | Suh ........................ C07K 16/22 530/387.3 |
| 2015/0152192 A1* | 6/2015 | Kim ....................... C07K 16/22 424/136.1 |

FOREIGN PATENT DOCUMENTS

| | | |
|---|---|---|
| JP | 2006-501147 A | 1/2006 |
| JP | 2006-526644 A | 11/2006 |
| KR | 2004-0106394 A | 12/2004 |
| KR | 2010-1224468 A | 11/2010 |
| KR | 2011-0047698 A | 5/2011 |
| KR | 2014-0035266 A | 3/2014 |
| WO | WO 03/090686 A2 | 11/2003 |
| WO | WO 2004/003019 * | 6/2004 |
| WO | WO 2005/000212 A2 | 1/2005 |
| WO | WO 2010/020618 A1 | 2/2010 |
| WO | WO 2011/060328 A1 | 5/2011 |
| WO | WO 2011/146803 A1 | 11/2011 |
| WO | WO 2012/037072 A1 | 3/2012 |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
R&D Systems (Catalog No. 358-MT; pp. 1-2; Oct. 12, 2015).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401-410).*

* cited by examiner

*Primary Examiner* — Lynn Bristol
(74) *Attorney, Agent, or Firm* — Leydig, Voit & Mayer, Ltd.

(57) ABSTRACT

An anti-c-Met/anti-Ang2 bispecific antibody including (a) an anti-c-Met antibody or antigen-binding fragment thereof and (b) an anti-Ang2 antibody or antigen-binding fragment thereof, a pharmaceutical composition including the anti-c-Met/anti-Ang2 bispecific antibody, and a method using the anti-c-Met/anti-Ang2 bispecific antibody.

13 Claims, 21 Drawing Sheets

SEQUENCE LISTING

<160> NUMBER OF SEQ ID NOS: 198

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
 1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
 1               5                  10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4

Xaa Xaa Tyr Tyr Met Ser
 1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val

```
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
 1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
 1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
 1               5                  10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8
```

```
Trp Xaa Ser Xaa Arg Val Xaa
  1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
  1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
  1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
  1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
  1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13
```

Gln Gln Ser Tyr Ser Arg Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
 1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
 1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

Asp Ile Gln Met Thr Gln Ser Pro Ser Ser Leu Ser Ala Ser Val Gly

```
            1               5                  10                 15
Asp Arg Val Thr Ile Thr Cys Lys Ser Ser Gln Ser Leu Leu Ala Ser
                    20                  25                  30

Gly Asn Gln Asn Asn Tyr Leu Ala Trp His Gln Gln Lys Pro Gly Lys
                35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                 70                  75                  80

Ile Ser Ser Leu Gln Pro Glu Asp Phe Ala Thr Tyr Tyr Cys Ala Gln
                    85                  90                  95

Ser Tyr Ser His Pro Phe Ser Phe Gly Gln Gly Thr Lys Val Glu Ile
                100                 105                 110

Lys Arg
```

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                    20                  25                  30

Gly Asn Gln Asn Asn Tyr Leu Ala Trp His Gln Gln Lys Pro Gly Lys
                35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                 70                  75                  80

Ile Ser Ser Leu Gln Pro Glu Asp Phe Ala Thr Tyr Tyr Cys Gln Gln
                    85                  90                  95

Ser Tyr Ser Arg Pro Phe Thr Phe Gly Gln Gly Thr Lys Val Glu Ile
                100                 105                 110

Lys Arg
```

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

```
Pro Glu Tyr Tyr Met Ser
 1               5
```

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

```
Pro Asp Tyr Tyr Met Ser
 1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
 1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
 1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
```

```
                1               5                  10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
  1               5                  10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
  1               5                  10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
  1               5                  10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
  1               5                  10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
  1               5

<210> SEQ ID NO 35
```

```
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
 1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
 1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
 1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctctg taacactttt aaatggtatc      60
cagtgtgagg tgaagctggt ggagtctgga ggaggcttgg tacagcctgg gggttctctg     120
```

```
agactctcct gtgcaacttc tgggttcacc ttcactgatt actacatgag ctgggtccgc    180
cagcctccag gaaaggcact tgagtggttg ggttttatta gaaacaaagc taatggttac    240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc caagggactc tggtcactgt ctctgcagct    420
agcaccaagg gcccatcggt cttccccctg gcacctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc cccatcccg ggaggagatg   1140 accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                             1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference

```
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg      60
ctgctgctat cggtatctgg tacctgtgga gacattttga tgacccagtc tccatcctcc    120
ctgactgtgt cagcaggaga gaaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                           759

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
             85                  90                  95

Tyr Cys Ala Arg Asp Asn Trp Phe Ala Tyr Trp Gly Gln Gly Thr Leu
        100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Asp Tyr
            20                  25                  30
Tyr Met Ser Trp Val Arg Gln Ala Pro Gly Lys Gly Leu Glu Trp Leu
        35                  40                  45
Gly Phe Ile Arg Asn Lys Ala Asn Gly Tyr Thr Thr Glu Tyr Ser Ala
    50                  55                  60
Ser Val Lys Gly Arg Phe Thr Ile Ser Arg Asp Asn Ser Lys Asn Ser
65                  70                  75                  80
Leu Tyr Leu Gln Met Asn Ser Leu Arg Ala Glu Asp Thr Ala Val Tyr
                85                  90                  95
Tyr Cys Ala Arg Asp Asn Trp Phe Ala Tyr Trp Gly Gln Gly Thr Leu
            100                 105                 110
Val Thr Val Ser Ser Ala Ser Thr Lys Gly Pro Ser Val Phe Pro Leu
        115                 120                 125
```

```
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45
```

```
Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
```

```
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Ala Ser
             20                  25                  30

Gly Asn Gln Asn Asn Tyr Leu Ala Trp His Gln Gln Lys Pro Gly Gln
         35                  40                  45

Pro Pro Lys Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
             85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
  1               5                  10                  15

Glu Pro Ala Ser Ile Ser Cys Lys Ser Ser Gln Ser Leu Leu Ala Ser
             20                  25                  30

Gly Asn Gln Asn Asn Tyr Leu Ala Trp His Leu Gln Lys Pro Gly Gln
         35                  40                  45

Ser Pro Gln Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
             85                  90                  95

Ser Tyr Ser Ala Pro Leu Thr Phe Gly Gln Gly Thr Lys Leu Glu Leu
            100                 105                 110
```

```
Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 46
<211> LENGTH: 219
<212> TYPE: PRT
<213> ORGANISM: Artificial Sequence
```

<220> FEATURE:
<223> OTHER INFORMATION: Synthetic amino acid sequence of H4-light

<400> SEQUENCE: 46

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215
```

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180
gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
```

| | |
|---|---|
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

| | |
|---|---|
| gaggtgcagc tggtggagtc tgggggaggc ttggtccagc ctggagggtc cctgagactc | 60 |
| tcctgtgcag cctctggatt caccttcact gactactaca tgagctgggt ccgccaggct | 120 |
| ccagggaagg ggctggagtg gttgggcttt attagaaaca agctaacgg ttacaccaca | 180 |
| gaatacagtg cgtctgtgaa aggcagattc accatctcaa gagataattc aaagaactca | 240 |
| ctgtatctgc aaatgaacag cctgcgtgct gaggacacgg ccgtgtatta ctgtgctaga | 300 |
| gataactggt tgcttactg gggtcaagga accctggtca ccgtctcctc ggctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc caggggggctc actccgtttg      60 tcctgtgcag cttctggctt caccttcact gattactaca tgagctgggt gcgtcaggcc     120
ccgggtaagg gcctggaatg gttgggtttt attagaaaca aagctaatgg ttacacaaca     180
gagtacagtg catctgtgaa gggtcgtttc actataagca gagataattc caaaaacaca     240
ctgtacctgc agatgaacag cctgcgtgct gaggacactg ccgtctatta ttgtgctaga     300
gataactggt ttgcttactg gggccaaggg actctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660 gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atgactcgag                                     1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50

```
gacatcgtga tgacccagtc tccagactcc ctggctgtgt ctctgggcga gagggccacc      60
atcaactgca gtccagcca gagtcttta gctagcggca accaaaataa ctacttagct     120
tggcaccagc agaaaccagg acagcctcct aagatgctca tatttgggc atctacccgg     180 gtatccgggg tccctgaccg attcagtggc agcgggtctg ggacagattt cactctcacc     240
atcagcagcc tgcaggctga agatgtggca gtttattact gtcagcaatc ctatagtgct     300
cctctcacgt tcggaggcgg taccaaggtg gagatcaaac gtacggtggc tgcaccatct     360
```

```
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
tgactcgag                                                            669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51

```
gatattgtga tgacccagac tccactctcc ctgcccgtca cccctggaga gccggcctcc    60
atctcctgca agtccagtca gagtctttta gctagtggga accaaaataa ctacttggcc    120
tggcacctgc agaagccagg gcagtctcca cagatgctga tcatttgggc atccactagg    180
gtatctggag tcccagacag gttcagtggc agtgggtcag gcactgattt cacactgaaa    240
atcagcaggg tggaggctga ggatgttgga gtttattact gccagcagtc ctacagcgct    300
ccgctcacgt tcggacaggg taccaagctg gagctcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
tgactcgag                                                            669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52

```
gacatcgtga tgacccagtc tccagactcc ctggctgtgt ctctgggcga gagggccacc    60
atcaactgca agtccagcca gagtctttta gctagcggca accaaaataa ctacttagct    120
tggtaccagc agaaaccagg acagcctcct aagctgctca tttatttggc atctacccgg    180
gtatccgggg tccctgaccg attcagtggc agcgggtctg gacagattt cactctcacc    240 atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
tgactcgag                                                            669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

| | | | | | |
|---|---|---|---|---|---|
| gatatccaga | tgacccagtc | cccgagctcc | ctgtccgcct | ctgtgggcga | tagggtcacc | 60 |
| atcacctgca | agtccagtca | gagtcttta | gctagtggca | accaaaataa | ctacttggcc | 120 |
| tggcaccaac | agaaaccagg | aaaagctccg | aaaatgctga | ttatttgggc | atccactagg | 180 |
| gtatctggag | tcccttctcg | cttctctgga | tccgggtctg | gacggattt | cactctgacc | 240 |
| atcagcagtc | tgcagccgga | agacttcgca | acttattact | gtcagcagtc | ctacagcgct | 300 |
| ccgctcacgt | tcggacaggg | taccaaggtg | gagatcaaac | gtacggtggc | tgcaccatct | 360 |
| gtcttcatct | tcccgccatc | tgatgagcag | ttgaaatctg | gaactgcctc | tgttgtgtgc | 420 |
| ctgctgaata | acttctatcc | cagagaggcc | aaagtacagt | ggaaggtgga | taacgccctc | 480 |
| caatcgggta | actcccagga | gagtgtcaca | gagcaggaca | gcaaggacag | cacctacagc | 540 |
| ctcagcagca | ccctgacgct | gagcaaagca | gactacgaga | aacacaaagt | ctacgcctgc | 600 |
| gaagtcaccc | atcagggcct | gagctcgccc | gtcacaaaga | gcttcaacag | gggagagtgt | 660 |
| tgactcgag | | | | | | 669 |

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Ser Gly
 1               5                  10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
    huAbF46 antibody

<400> SEQUENCE: 55

| | | | | | |
|---|---|---|---|---|---|
| gctagcgttt | tagcagaagt | tcaattggtt | gaatctggtg | gtggtttggt | tcaaccaggt | 60 |
| ggttctttga | gattgtcttg | tgctgcttct | ggttttactt | tcaccgatta | ttacatgtcc | 120 |
| tgggttagac | aagctccagg | taaaggtttg | gaatggttgg | gtttcattag | aaacaaggct | 180 |
| aacggttaca | ctaccgaata | ttctgcttct | gttaaggta | gattcaccat | ttctagagac | 240 |
| aactctaaga | acaccttgta | cttgcaaatg | aactccttga | gagctaaga | tactgctgtt | 300 |
| tattactgcg | ctagagataa | ttggtttgct | tattgggtc | aaggtacttt | ggttactgtt | 360 |
| tcttctggcc | tcgggggcct | cggaggagga | ggtagtggcg | gaggaggctc | cggtggatcc | 420 |
| agcggtgtgg | gttccgatat | tcaaatgacc | caatctccat | cttctttgtc | tgcttcagtt | 480 |
| ggtgatagag | ttaccattac | ttgtaagtcc | tcccaatctt | tgttggcttc | tggtaatcag | 540 |

-continued

```
aacaattact tggcttggca tcaacaaaaa ccaggtaaag ctccaaagat gttgattatt      600
tgggcttcta ccagagtttc tggtgttcca tctagatttt ctggttctgg ttccggtact      660
gattttactt tgaccatttc atccttgcaa ccagaagatt tcgctactta ctactgtcaa      720
caatcttact ctgctccatt gacttttggt caaggtacaa aggtcgaaat caagagagaa      780
ttcggtaagc ctatccctaa ccctctcctc ggtctcgatt ctacgggtgg tggtggatct      840
ggtggtggtg ttctggtgg tggtggttct caggaactga caactatatg cgagcaaatc      900
ccctcaccaa ctttagaatc gacgccgtac tctttgtcaa cgactactat tttggccaac      960
gggaaggcaa tgcaaggagt ttttgaatat tacaaatcag taacgtttgt cagtaattgc     1020
ggttctcacc cctcaacaac tagcaaaggc agccccataa acacacagta tgttttttga     1080
gtttaaac                                                              1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

```
acggattaga agccgccgag cgggtgacag ccctccgaag gaagactctc ctccgtgcgt       60
cctcgtcttc accggtcgcg ttcctgaaac gcagatgtgc ctcgcgccgc actgctccga      120
acaataaaga ttctacaata ctagctttta tggttatgaa gaggaaaaat tggcagtaac      180
ctggccccac aaaccttcaa atgaacgaat caaattaaca accataggat gataatgcga      240
```

```
ttagttttttt agccttattt ctggggtaat taatcagcga agcgatgatt tttgatctat      300
taacagatat ataaatgcaa aaactgcata accactttaa ctaatacttt caacattttc      360
ggtttgtatt acttcttatt caaatgtaat aaaagtatca acaaaaaatt gttaatatac      420
ctctatactt taacgtcaag gagaaaaaac cccggatcgg actactagca gctgtaatac      480
gactcactat agggaatatt aagctaattc tacttcatac attttcaatt aagatgcagt      540
tacttcgctg ttttcaata ttttctgtta ttgctagcgt tttagcagaa gttcaattgg       600
ttgaatctgg tggtggtttg gttcaaccag gtggttcttt gagattgtct tgtgctgctt      660
ctggttttac tttcaccgat tattacatgt cctgggttag acaagctcca ggtaaaggtt      720
tggaatggtt gggtttcatt agaaacaagg ctaacggtta cactaccgaa tattctgctt      780
ctgttaaggg tagattcacc atttctagag acaactctaa gaacaccttg tacttgcaaa      840
tgaactcctt gagagctgaa gatactgctg tttattactg cgctagagat aattggtttg      900
cttattgggg tcaaggtact ttggttactg tttcttctgg cctcggggc ctcggaggag       960 gaggtagtgg cggaggaggc tccggtggat ccagcggtgt gggttccgat attcaaatga     1020
cccaatctcc atcttctttg tctgcttcag ttggtgatag agttaccatt acttgtaagt     1080
cctcccaatc tttgttggct tctggtaatc agaacaatta cttggcttgg catcaacaaa     1140
aaccaggtaa agctccaaag atgttgatta tttgggcttc taccagagtt tctggtgttc     1200
catctagatt ttctggttct ggttccgtta ctgattttac tttgaccatt tcatccttgc     1260
aaccagaaga tttcgctact tactactgtc aacaatctta ctctgctcca ttgacttttg     1320
gtcaaggtac aaaggtcgaa atcaagagag aattcggtaa gcctatccct aaccctctcc     1380
tcggtctcga ttctacgggt ggtggtggat ctggtggtgg tggttctggt ggtggtggtt     1440
ctcaggaact gacaactata tgcgagcaaa tcccctcacc aactttagaa tcgacgccgt     1500
actctttgtc aacgactact attttggcca acgggaaggc aatgcaagga gtttttgaat     1560
attacaaatc agtaacgttt gtcagtaatt gcggttctca cccctcaaca actagcaaag     1620
gcagccccat aaacacacag tatgttttttt gagtttaaac ccgctgatct gataacaaca     1680
gtgtagatgt aacaaaatcg actttgttcc cactgtactt ttagctcgta caaaatacaa     1740 tatactttc atttctccgt aaacaacatg ttttcccatg taatatcctt ttctattttt      1800
cgttccgtta ccaactttac acatacttta tatagctatt cacttctata cactaaaaaa     1860
ctaagacaat tttaattttg ctgcctgcca tatttcaatt tgttataaat tcctataatt     1920
tatcctatta gtagctaaaa aaagatgaat gtgaatcgaa tcctaagaga attgggcaag     1980
tgcacaaaca atacttaaat aaatactact cagtaataac ctatttctta gcattttga     2040 cgaaatttgc tattttgtta gagtctttta caccatttgt ctccacacct ccgcttacat     2100
caacaccaat aacgccattt aatctaagcg catcaccaac attttctggc gtcagtccac     2160
cagctaacat aaaatgtaag ctctcggggc tctcttgcct tccaacccag tcagaaatcg     2220
agttccaatc caaaagttca cctgtcccac ctgcttctga atcaaacaag ggaataaacg     2280
aatgaggttt ctgtgaagct gcactgagta gtatgttgca gtcttttgga aatacgagtc     2340
ttttaataac tggcaaaccg aggaactctt ggtattcttg ccacgactca tctccgtgca     2400
gttggacgat atcaatgccg taatcattga ccagagccaa acatcctcc ttaggttgat      2460 tacgaaacac gccaaccaag tatttcggag tgcctgaact atttttatat gcttttacaa     2520
gacttgaaat tttccttgca ataaccgggt caattgttct ctttctattg ggcacacata     2580
```

```
taatacccag caagtcagca tcggaatcta gagcacattc tgcggcctct gtgctctgca    2640
agccgcaaac tttcaccaat ggaccagaac tacctgtgaa attaataaca gacatactcc    2700
aagctgcctt tgtgtgctta atcacgtata ctcacgtgct caatagtcac caatgccctc    2760
cctcttggcc ctctccttttt cttttttcga ccgaatttct tgaagacgaa agggcctcgt    2820
gatacgccta tttttatagg ttaatgtcat gataataatg gtttcttagg acggatcgct    2880
tgcctgtaac ttacacgcgc ctcgtatctt ttaatgatgg aataatttgg gaatttactc    2940
tgtgtttatt tatttttatg ttttgtattt ggattttaga aagtaaataa agaaggtaga    3000
agagttacgg aatgaagaaa aaaaaataaa caaaggttta aaaaatttca acaaaaagcg    3060
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaggt agtatttgtt    3240
ggcgatcccc ctagagtctt ttacatcttc ggaaaacaaa aactattttt tcttaatt    3300
cttttttac tttctatttt taatttatat atttatatta aaaatttaa attataatta    3360
tttttatagc acgtgatgaa aaggaccag gtggcacttt tcggggaaat gtgcgcggaa    3420
cccctattg tttatttttc taaatacatt caaatatgta tccgctcatg agacaataac    3480
cctgataaat gcttcaataa tattgaaaaa ggaagagtat gagtattcaa catttccgtg    3540
tcgcccttat tccctttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga agaacgtttt ccaatgatga    3720
gcacttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga caacgatcgg aggaccgaag gagctaaccg    3960
cttttttgca caacatgggg gatcatgtaa ctcgccttga tcgttgggaa ccggagctga    4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca agtttactca tatatacttt agattgattt aaaacttcat ttttaattta    4440
aaaggatcta ggtgaagatc cttttttgata atctcatgac caaaatccct taacgtgagt    4500
tttcgttcca ctgagcgtca gaccccgtag aaaagatcaa aggatcttct tgagatcctt    4560
tttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
```

```
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
ttttgtgatg ctcgtcaggg gggccgagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                   5597

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
  1               5                  10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc ccgtacacgt tcggacaggg taccaaggtg    420
gagatcaaac gtacg                                                    435

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180
```

```
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgggcagtc ctacagccgt ccgctcacgt tcggacaggg taccaaggtg    420
gagatcaaac gtacg                                                     435

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60
gaattcacta gtgattaatt cgccgccacc atggattcac aggcccaggt cctcatgttg    60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgcacagtc ctacagccat ccgttctctt tcggacaggg taccaaggtg    420
gagatcaaac gtacg                                                     435

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61
gaattcacta gtgattaatt cgccgccacc atggattcac aggcccaggt cctcatgttg    60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                     435

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, U6-HC7 hinge and constant region of human IgG1

<400> SEQUENCE: 62

Met Glu Trp Ser Trp Val Phe Leu Val Thr Leu Leu Asn Gly Ile Gln
 1               5                  10                  15
```

-continued

```
Cys Glu Val Gln Leu Val Glu Ser Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65              70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
             100                 105                 110

Tyr Tyr Cys Ala Arg Asp Asn Trp Phe Ala Tyr Trp Gly Gln Gly Thr
         115                 120                 125

Leu Val Thr Val Ser Ser Ala Ser Thr Lys Gly Pro Ser Val Phe Pro
     130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                 165                 170                 175

Ser Gly Ala Leu Thr Ser Gly Val His Thr Phe Pro Ala Val Leu Gln
             180                 185                 190

Ser Ser Gly Leu Tyr Ser Leu Ser Ser Val Val Thr Val Pro Ser Ser
         195                 200                 205

Ser Leu Gly Thr Gln Thr Tyr Ile Cys Asn Val Asn His Lys Pro Ser
     210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                 245                 250                 255

Leu Phe Pro Pro Lys Pro Lys Asp Thr Leu Met Ile Ser Arg Thr Pro
             260                 265                 270

Glu Val Thr Cys Val Val Val Asp Val Ser His Glu Asp Pro Glu Val
         275                 280                 285

Lys Phe Asn Trp Tyr Val Asp Gly Val Glu Val His Asn Ala Lys Thr
     290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                 325                 330                 335

Lys Val Ser Asn Lys Ala Leu Pro Ala Pro Ile Glu Lys Thr Ile Ser
             340                 345                 350

Lys Ala Lys Gly Gln Pro Arg Glu Pro Gln Val Tyr Thr Leu Pro Pro
         355                 360                 365

Ser Arg Glu Glu Met Thr Lys Asn Gln Val Ser Leu Thr Cys Leu Val
     370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                 405                 410                 415

Gly Ser Phe Phe Leu Tyr Ser Lys Leu Thr Val Asp Lys Ser Arg Trp
             420                 425                 430

Gln Gln Gly Asn Val Phe Ser Cys Ser Val Met His Glu Ala Leu His
```

435                 440                 445
Asn His Tyr Thr Gln Lys Ser Leu Ser Leu Ser Pro Gly Lys
    450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63
gaattcgccg ccaccatgga atggagctgg gttttctcg taacactttt aaatggtatc      60
cagtgtgagg ttcagctggt ggagtctggc ggtggcctgg tgcagccagg ggctcactc     120 cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc aagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca gagcaggtg gcagcagggg   1320 aacgtcttct catgctccgt gatgcatgag gctctgcaca accactacac gcagaagagc   1380
ctctccctgt ctccgggtaa atgactcgag                                    1410

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of human
      IgG1

<400> SEQUENCE: 64

Met Glu Trp Ser Trp Val Phe Leu Val Thr Leu Leu Asn Gly Ile Gln
 1               5                  10                  15

```
Cys Glu Val Gln Leu Val Glu Ser Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
 50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
             100                 105                 110

Tyr Tyr Cys Ala Arg Asp Asn Trp Phe Ala Tyr Trp Gly Gln Gly Thr
         115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                 165                 170                 175

Ser Gly Ala Leu Thr Ser Gly Val His Thr Phe Pro Ala Val Leu Gln
             180                 185                 190

Ser Ser Gly Leu Tyr Ser Leu Ser Ser Val Val Thr Val Pro Ser Ser
         195                 200                 205

Ser Leu Gly Thr Gln Thr Tyr Ile Cys Asn Val Asn His Lys Pro Ser
210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                 245                 250                 255

Phe Pro Pro Lys Pro Lys Asp Thr Leu Met Ile Ser Arg Thr Pro Glu
             260                 265                 270

Val Thr Cys Val Val Val Asp Val Ser His Glu Asp Pro Glu Val Lys
         275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                 325                 330                 335

Val Ser Asn Lys Ala Leu Pro Ala Pro Ile Glu Lys Thr Ile Ser Lys
             340                 345                 350

Ala Lys Gly Gln Pro Arg Glu Pro Gln Val Tyr Thr Leu Pro Pro Ser
         355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                 405                 410                 415

Ser Phe Phe Leu Tyr Ser Lys Leu Thr Val Asp Lys Ser Arg Trp Gln
             420                 425                 430
```

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG1

<400> SEQUENCE: 65
gaattcgccg ccaccatgga atggagctgg gttttttctcg taacactttt aaatggtatc       60
cagtgtgagg ttcagctggt ggagtctggc ggtggcctgg tgcagccagg gggctcactc      120
cgtttgtcct gtgcagcttc tggcttcacc ttcactgatt actacatgag ctgggtgcgt      180
caggccccgg gtaagggcct ggaatggttg gttttattta gaaacaaagc taatggttac      240
acaacagagt acagtgcatc tgtgaagggt cgtttcacta taagcagaga taattccaaa      300
aacacactgt acctgcagat gaacagcctg cgtgctgagg acactgccgt ctattattgt      360
gctagagata actggtttgc ttactggggc cagggactc tggtcaccgt ctcctcggct       420
agcaccaagg gcccatcggt cttcccctg caccctcct ccaagagcac ctctgggggc        480
acagcggccc tgggctgcct ggtcaaggac tacttcccg aaccggtgac ggtgtcgtgg       540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagaggaag     720
tgctgtgtgg agtgccccc ctgcccagca cctgaactcc tggggggacc gtcagtcttc      780
ctcttccccc caaaacccaa ggacaccctc atgatctccc ggaccctga ggtcacatgc       840
gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
aaggtctcca acaaagccct cccagcccc atcgagaaaa ccatctccaa agccaaaggg      1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac    1260
ggctccttct cctctacag caagctcacc gtggacaaga gcaggtggca gcaggggaac     1320
gtcttctcat gctccgtgat gcatgaggct ctgcacaacc actacacgca gaagagcctc    1380
tccctgtctc cgggtaaatg actcgag                                        1407

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of human
      IgG2

<400> SEQUENCE: 66

Met Glu Trp Ser Trp Val Phe Leu Val Thr Leu Leu Asn Gly Ile Gln

```
  1               5                  10                 15
Cys Glu Val Gln Leu Val Glu Ser Gly Gly Gly Leu Val Gln Pro Gly
                 20                 25                 30
Gly Ser Leu Arg Leu Ser Cys Ala Ala Ser Gly Phe Thr Phe Thr Asp
                 35                 40                 45
Tyr Tyr Met Ser Trp Val Arg Gln Ala Pro Gly Lys Gly Leu Glu Trp
     50                  55                 60
Leu Gly Phe Ile Arg Asn Lys Ala Asn Gly Tyr Thr Thr Glu Tyr Ser
 65                  70                  75                 80
Ala Ser Val Lys Gly Arg Phe Thr Ile Ser Arg Asp Asn Ser Lys Asn
                 85                  90                 95
Thr Leu Tyr Leu Gln Met Asn Ser Leu Arg Ala Glu Asp Thr Ala Val
                100                 105                110
Tyr Tyr Cys Ala Arg Asp Asn Trp Phe Ala Tyr Trp Gly Gln Gly Thr
                115                 120                125
Leu Val Thr Val Ser Ser Ala Ser Thr Lys Gly Pro Ser Val Phe Pro
        130                 135                 140
Leu Ala Pro Cys Ser Arg Ser Thr Ser Glu Ser Thr Ala Ala Leu Gly
145                 150                 155                160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
        180                 185                 190
Ser Ser Gly Leu Tyr Ser Leu Ser Ser Val Val Thr Val Pro Ser Ser
        195                 200                 205
Asn Phe Gly Thr Gln Thr Tyr Thr Cys Asn Val Asp His Lys Pro Ser
        210                 215                 220
Asn Thr Lys Val Asp Lys Thr Val Glu Arg Lys Cys Cys Val Glu Cys
225                 230                 235                240
Pro Pro Cys Pro Ala Pro Pro Val Ala Gly Pro Ser Val Phe Leu Phe
                245                 250                 255
Pro Pro Lys Pro Lys Asp Thr Leu Met Ile Ser Arg Thr Pro Glu Val
                260                 265                 270
Thr Cys Val Val Val Asp Val Ser His Glu Asp Pro Glu Val Gln Phe
        275                 280                 285
Asn Trp Tyr Val Asp Gly Val Glu Val His Asn Ala Lys Thr Lys Pro
        290                 295                 300
Arg Glu Glu Gln Phe Asn Ser Thr Phe Arg Val Val Ser Val Leu Thr
305                 310                 315                320
Val Val His Gln Asp Trp Leu Asn Gly Lys Glu Tyr Lys Cys Lys Val
                325                 330                 335
Ser Asn Lys Gly Leu Pro Ala Pro Ile Glu Lys Thr Ile Ser Lys Thr
                340                 345                 350
Lys Gly Gln Pro Arg Glu Pro Gln Val Tyr Thr Leu Pro Pro Ser Arg
                355                 360                 365
Glu Glu Met Thr Lys Asn Gln Val Ser Leu Thr Cys Leu Val Lys Gly
                370                 375                 380
Phe Tyr Pro Ser Asp Ile Ala Val Glu Trp Glu Ser Asn Gly Gln Pro
385                 390                 395                400
Glu Asn Asn Tyr Lys Thr Thr Pro Pro Met Leu Asp Ser Asp Gly Ser
                405                 410                 415
Phe Phe Leu Tyr Ser Lys Leu Thr Val Asp Lys Ser Arg Trp Gln Gln
                420                 425                 430
```

Gly Asn Val Phe Ser Cys Ser Val Met His Glu Ala Leu His Asn His
              435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG2

<400> SEQUENCE: 67

| | | | | | |
|---|---|---|---|---|---|
| gaattcgccg | ccaccatgga | atggagctgg | gttttctcg | taacactttt | aaatggtatc | 60 |
| cagtgtgagg | ttcagctggt | ggagtctggc | ggtggcctgg | tgcagccagg | gggctcactc | 120 |
| cgtttgtcct | gtgcagcttc | tggcttcacc | ttcactgatt | actacatgag | ctgggtgcgt | 180 |
| caggccccgg | gtaagggcct | ggaatggttg | ggttttatta | gaaacaaagc | taatggttac | 240 |
| acaacagagt | acagtgcatc | tgtgaagggt | cgtttcacta | taagcagaga | taattccaaa | 300 |
| aacacactgt | acctgcagat | gaacagcctg | cgtgctgagg | acactgccgt | ctattattgt | 360 |
| gctagagata | actggtttgc | ttactggggc | caagggactc | tggtcaccgt | ctcctcggct | 420 |
| agcaccaagg | gcccatcggt | cttccccctg | gcgccctgct | ccaggagcac | ctccgagagc | 480 |
| acagcggccc | tgggctgcct | ggtcaaggac | tacttcccg | aaccggtgac | ggtgtcgtgg | 540 |
| aactcaggcg | ctctgaccag | cggcgtgcac | accttcccag | ctgtcctaca | gtcctcagga | 600 |
| ctctactccc | tcagcagcgt | ggtgaccgtg | ccctccagca | acttcggcac | ccagacctac | 660 |
| acctgcaacg | tagatcacaa | gcccagcaac | accaaggtgg | acaagacagt | tgagcgcaaa | 720 |
| tgttgtgtcg | agtgcccacc | gtgcccagca | ccacctgtgg | caggaccgtc | agtcttcctc | 780 |
| ttccccccaa | aacccaagga | caccctcatg | atctcccgga | cccctgaggt | cacgtgcgtg | 840 |
| gtggtggacg | tgagccacga | agaccccgag | gtccagttca | actggtacgt | ggacggcgtg | 900 |
| gaggtgcata | atgccaagac | aaagccacgg | gaggagcagt | tcaacagcac | gttccgtgtg | 960 |
| gtcagcgtcc | tcaccgttgt | gcaccaggac | tggctgaacg | gcaaggagta | caagtgcaag | 1020 |
| gtctccaaca | aaggcctccc | agcccccatc | gagaaaacca | tctccaaaac | caaagggcag | 1080 |
| ccccgagaac | cacaggtgta | caccctgccc | ccatcccggg | aggagatgac | caagaaccag | 1140 |
| gtcagcctga | cctgcctggt | caaaggcttc | taccccagcg | acatcgccgt | ggagtgggag | 1200 |
| agcaatgggc | agccggagaa | caactacaag | accacgcctc | ccatgctgga | ctccgacggc | 1260 |
| tccttcttcc | tctacagcaa | gctcaccgtg | gacaagagca | ggtggcagca | ggggaacgtc | 1320 |
| ttctcatgct | ccgtgatgca | tgaggctctg | cacaaccact | acacgcagaa | gagcctctcc | 1380 |
| ctgtctccgg | gtaaatgact | cgag | | | | 1404 |

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1(H36Y) and human kappa constant region

<400> SEQUENCE: 68

Met Asp Ser Gln Ala Gln Val Leu Met Leu Leu Leu Leu Ser Val Ser

```
              1               5                  10                 15
          Gly Thr Cys Gly Asp Ile Gln Met Thr Gln Ser Pro Ser Ser Leu Ser
                          20                  25                  30

Ala Ser Val Gly Asp Arg Val Thr Ile Thr Cys Lys Ser Gln Ser
                          35                  40                  45

Leu Leu Ala Ser Gly Asn Gln Asn Asn Tyr Leu Ala Trp Tyr Gln Gln
                       50                  55                  60

Lys Pro Gly Lys Ala Pro Lys Met Leu Ile Ile Trp Ala Ser Thr Arg
           65                  70                  75                  80

Val Ser Gly Val Pro Ser Arg Phe Ser Gly Ser Gly Ser Gly Thr Asp
                              85                  90                  95

Phe Thr Leu Thr Ile Ser Ser Leu Gln Pro Glu Asp Phe Ala Thr Tyr
                         100                 105                 110

Tyr Cys Gln Gln Ser Tyr Ser Arg Pro Tyr Thr Phe Gly Gln Gly Thr
                         115                 120                 125

Lys Val Glu Ile Lys Arg Thr Val Ala Ala Pro Ser Val Phe Ile Phe
           130                 135                 140

Pro Pro Ser Asp Glu Gln Leu Lys Ser Gly Thr Ala Ser Val Val Cys
          145                 150                 155                 160

Leu Leu Asn Asn Phe Tyr Pro Arg Glu Ala Lys Val Gln Trp Lys Val
                              165                 170                 175

Asp Asn Ala Leu Gln Ser Gly Asn Ser Gln Glu Ser Val Thr Glu Gln
                         180                 185                 190

Asp Ser Lys Asp Ser Thr Tyr Ser Leu Ser Ser Thr Leu Thr Leu Ser
                         195                 200                 205

Lys Ala Asp Tyr Glu Lys His Lys Val Tyr Ala Cys Glu Val Thr His
           210                 215                 220

Gln Gly Leu Ser Ser Pro Val Thr Lys Ser Phe Asn Arg Gly Glu Cys
          225                 230                 235                 240

<210> SEQ ID NO 69
          <211> LENGTH: 758
          <212> TYPE: DNA
          <213> ORGANISM: Artificial Sequence
          <220> FEATURE:
          <223> OTHER INFORMATION: Synthetic polynucleotide encoding polypeptide
                consisting of light chain of huAbF46-H4-A1(H36Y) and human kappa
                constant region

<400> SEQUENCE: 69
aattcactag tgattaattc gccgccacca tggattcaca ggcccaggtc ctcatgttgc    60
tgctgctatc ggtatctggt acctgtggag atatccagat gacccagtcc ccgagctccc   120
tgtccgcctc tgtgggcgat agggtcacca tcacctgcaa gtccagtcag agtcttttag   180
ctagtggcaa ccaaaataac tacttggcct ggtaccaaca gaaaccagga aaagctccga   240
aaatgctgat tatttgggca tccactaggg tatctgagt cccttctcgc ttctctggat   300
ccgggtctgg gacggatttc actctgacca tcagcagtct gcagccggaa gacttcgcaa   360
cttattactg tcagcagtcc tacagccgcc cgtacacgtt cggacagggt accaaggtgg   420
agatcaaacg tacggtggct gcaccatctg tcttcatctt cccgccatct gatgagcagt   480
tgaaatctgg aactgcctct gttgtgtgcc tgctgaataa cttctatccc agagaggcca   540
aagtacagtg gaaggtggat aacgccctcc aatcgggtaa ctcccaggag agtgtcacag   600
agcaggacag caaggacagc acctacagcc tcagcagcac cctgacgctg agcaaagcag   660
actacgagaa acacaaagtc tacgcctgcg aagtcaccca tcagggcctg agctcgcccg   720
```
tcacaaagag cttcaacagg ggagagtgtt gactcgag      758

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1 and human kappa constant region

<400> SEQUENCE: 70

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence

```
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
 1               5                  10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
 1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of anti-
      c-Met antibody (AbF46 or huAbF46-H1)

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
                20                  25                  30

Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Ser
 65                 70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of anti-
      c-Met antibody (AbF46 or huAbF46-H1)

<400> SEQUENCE: 75

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
                20                  25                  30

Gly Asn Gln Asn Asn Tyr Leu Ala Trp His Gln Gln Lys Pro Gly Gln
            35                  40                  45

Pro Pro Lys Met Leu Ile Ile Trp Ala Ser Thr Arg Val Ser Gly Val
        50                  55                  60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg ggttctctg    120 agactctcct gtgcaacttc tgggttcacc ttcactgatt actacatgag ctgggtccgc    180
cagcctccag aaaggcact tgagtggttg ggttttatta aaacaaagc taatggttac    240 acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc aagggactc tggtcactgt ctctgcagct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttccccc aaaacccaag gacaccctca tgatctcccg gacccctgag    840
gtcacatgcg tggtggtgga cgtgagccac gaagaccctg aggtcaagtt caactggtac    900
```

```
gtggacggcg tggaggtgca taatgccaag acaaagccgc gggaggagca gtacaacagc      960
acgtaccgtg tggtcagcgt cctcaccgtc ctgcaccagg actggctgaa tggcaaggag     1020
tacaagtgca aggtctccaa caaagccctc ccagccccca tcgagaaaac catctccaaa     1080
gccaaagggc agccccgaga accacaggtg tacaccctgc ccccatcccg ggaggagatg     1140
accaagaacc aggtcagcct gacctgcctg gtcaaaggct tctatcccag cgacatcgcc     1200
gtggagtggg agagcaatgg gcagccggag aacaactaca agaccacgcc tcccgtgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga ctcgag                               1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atggattcac aggcccaggt cctcatgttg       60
ctgctgctat cggtatctgg tacctgtgga gacattttga tgacccagtc tccatcctcc      120
ctgactgtgt cagcaggaga gaaggtcact atgagctgca agtccagtca gagtctttta      180
gctagtggca accaaaataa ctacttggcc tggcaccagc agaaaccagg acgatctcct      240
aaaatgctga taatttgggc atccactagg gtatctggag tccctgatcg cttcataggc      300
agtggatctg ggacggattt cactctgacc atcaacagtg tgcaggctga agatctggct      360
gtttattact gtcagcagtc ctacagcgct ccgctcacgt tcggtgctgg gaccaagctg      420
gagctgaaac gtacggtggc tgcaccatct gtcttcatct tcccgccatc tgatgagcag      480
ttgaaatctg gaactgcctc tgttgtgtgc ctgctgaata acttctatcc cagagaggcc      540
aaagtacagt ggaaggtgga taacgccctc caatcgggta actcccagga gagtgtcaca      600
gagcaggaca gcaaggacag cacctacagc ctcagcagca ccctgacgct gagcaaagca      660
```

```
gactacgaga acacaaagt ctacgcctgc gaagtcaccc atcagggcct gagctcgccc      720
gtcacaaaga gcttcaacag gggagagtgt tgactcgag                            759

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78
atgaaggccc ccgctgtgct tgcacctggc atcctcgtgc tcctgtttac cttggtgcag       60
aggagcaatg gggagtgtaa agaggcacta gcaaagtccg agatgaatgt gaatatgaag      120
tatcagcttc ccaacttcac cgcggaaaca cccatccaga atgtcattct acatgagcat      180
cacattttcc ttggtgccac taactacatt tatgttttaa atgaggaaga ccttcagaag      240
gttgctgagt acaagactgg gcctgtgctg aacacccag attgtttccc atgtcaggac       300
tgcagcagca agccaatttt atcaggaggt gtttggaaag ataacatcaa catggctcta      360
gttgtcgaca cctactatga tgatcaactc attagctgtg gcagcgtcaa cagagggacc      420
tgccagcgac atgtctttcc ccacaatcat actgctgaca tacagtcgga ggttcactgc      480
atattctccc cacagataga agagcccagc cagtgtcctg actgtgtggt gagcgccctg      540
ggagccaaag tcctttcatc tgtaaaggac cggttcatca acttctttgt aggcaatacc      600
ataaattctt cttatttccc agatcatcca ttgcattcga tatcagtgag aaggctaaag      660
gaaacgaaag atggttttat gttttttgacg gaccagtcct acattgatgt tttacctgag     720
ttcagagatt cttaccccat taagtatgtc catgcctttg aaagcaacaa ttttatttac      780
ttcttgacgg tccaaaggga aactctagat gctcagactt tcacacaag aataatcagg      840 ttctgttcca taaactctgg attgcattcc tacatggaaa tgcctctgga gtgtattctc      900
acagaaaaga gaaaaaagag atccacaaag aaggaagtgt taatatact tcaggctgcg      960 tatgtcagca agcctggggc ccagcttgct agacaaatag agccagcct gaatgatgac     1020 attcttttcg gggtgttcgc acaaagcaag ccagattctg ccgaaccaat ggatcgatct     1080
gccatgtgtg cattccctat caaatatgtc aacgacttct tcaacaagat cgtcaacaaa     1140
aacaatgtga gatgtctcca gcattttttac ggacccaatc atgagcactg ctttaatagg     1200
acacttctga gaaattcatc aggctgtgaa gcgcgccgtg atgaatatcg aacagagttt     1260
accacagctt gcagcgcgt tgacttattc atgggtcaat tcagcgaagt cctcttaaca     1320
tctatatcca ccttcattaa aggagacctc accatagcta atcttgggac atcagagggt     1380
cgcttcatgc aggttgtggt ttctcgatca ggaccatcaa cccctcatgt gaattttctc     1440
ctggactccc atccagtgtc tccagaagtg attgtggagc atacattaaa ccaaaatggc     1500
tacacactgg ttatcactgg gaagaagatc acgaagatcc cattgaatgg cttgggctgc     1560
agacatttcc agtcctgcag tcaatgcctc tctgccccac cctttgttca gtgtggctgg     1620
tgccacgaca aatgtgtgcg atcggaggaa tgcctgagcg ggacatggac tcaacagatc     1680
tgtctgcctg caatctacaa ggttttccca aatagtgcac cccttgaagg agggacaagg     1740
ctgaccatat gtggctggga ctttggattt cggaggaata taaatttga tttaaagaaa     1800 actagagttc tccttggaaa tgagagctgc accttgactt aagtgagag cacgatgaat     1860 acattgaaat gcacagttgg tcctgccatg aataagcatt tcaatatgtc cataattatt     1920
```

```
tcaaatggcc acgggacaac acaatacagt acattctcct atgtggatcc tgtaataaca      1980
agtatttcgc cgaaatacgg tcctatggct ggtggcactt tacttacttt aactggaaat      2040
tacctaaaca gtgggaattc tagacacatt tcaattggtg gaaaaacatg tactttaaaa      2100
agtgtgtcaa acagtattct tgaatgttat accccagccc aaaccatttc aactgagttt      2160
gctgttaaat tgaaaattga cttagccaac cgagagacaa gcatcttcag ttaccgtgaa      2220
gatcccattg tctatgaaat tcatccaacc aaatctttta ttagtggtgg agcacaata      2280
acaggtgttg ggaaaaacct gaattcagtt agtgtcccga gaatggtcat aaatgtgcat      2340
gaagcaggaa ggaactttac agtggcatgt caacatcgct ctaattcaga gataatctgt      2400
tgtaccactc cttccctgca acagctgaat ctgcaactcc ccctgaaaac caaagccttt      2460
ttcatgttag atgggatcct ttccaaatac tttgatctca tttatgtaca taatcctgtg      2520
tttaagcctt ttgaaaagcc agtgatgatc tcaatgggca atgaaaatgt actggaaatt      2580
aagggaaatg atattgaccc tgaagcagtt aaaggtgaag tgttaaaagt tggaaataag      2640
agctgtgaga atatacactt acattctgaa gccgttttat gcacggtccc caatgacctg      2700
ctgaaattga acagcgagct aaatatagag tggaagcaag caatttcttc aaccgtcctt      2760
ggaaaagtaa tagttcaacc agatcagaat ttcacaggat tgattgctgg tgttgtctca      2820
atatcaacag cactgttatt actacttggg ttttcctgt ggctgaaaaa gagaaagcaa      2880
attaaagatc tgggcagtga attagttcgc tacgatgcaa gagtacacac tcctcatttg      2940
gataggcttg taagtgcccg aagtgtaagc ccaactacag aaatggtttc aaatgaatct      3000
gtagactacc gagctacttt tccagaagat cagtttccta attcatctca gaacggttca      3060
tgccgacaag tgcagtatcc tctgacagac atgtccccca tcctaactag tggggactct      3120
gatatatcca gtccattact gcaaaatact gtccacattg acctcagtgc tctaaatcca      3180
gagctggtcc aggcagtgca gcatgtagtg attgggccca gtagcctgat tgtgcatttc      3240
aatgaagtca taggaagagg gcattttggt tgtgtatatc atgggacttt gttgacaat      3300
gatggcaaga aaattcactg tgctgtgaaa tccttgaaca gaatcactga cataggagaa      3360
gtttcccaat ttctgaccga gggaatcatc atgaaagatt ttagtcatcc caatgtcctc      3420
tcgctcctgg aatctgcct cgaagtgaa gggtctccgc tggtggtcct accatacatg      3480
aaacatggag atcttcgaaa tttcattcga aatgagactc ataatccaac tgtaaaagat      3540
cttattggct ttggtcttca agtagccaaa ggcatgaaat atcttgcaag caaaaagttt      3600
gtccacagag acttggctgc aagaaactgt atgctggatg aaaaattcac agtcaaggtt      3660
gctgattttg gtcttgccag agacatgtat gataaagaat actatagtgt acacaacaaa      3720
acaggtgcaa agctgccagt gaagtggatg gctttggaaa gtctgcaaac tcaaaagttt      3780
accaccaagt cagatgtgtg gtcctttggc gtgctcctct gggagctgat gacaagagga      3840
gccccacctt atcctgacgt aaacaccttt gatataactg tttacttgtt gcaagggaga      3900
agactcctac aacccgaata ctgcccagac cccttatatg aagtaatgct aaaatgctgg      3960
cacctaaag ccgaaatgcg cccatccttt tctgaactgg tgtcccggat atcagcgatc      4020
ttctctactt tcattgggga gcactatgtc catgtgaacg ctacttatgt gaacgtaaaa      4080
tgtgtcgctc cgtatccttc tctgttgtca tcagaagata cgctgatga tgaggtggac      4140
acacgaccag cctccttctg ggagacatca                                      4170
```

<210> SEQ ID NO 79
<211> LENGTH: 444

```
<212> TYPE: PRT
<213> ORGANISM: Artificial Sequence
<220> FEATURE:
<223> OTHER INFORMATION: Synthetic SEMA domain of c-Met

<400> SEQUENCE: 79
```

| | | | | | | | | | | | |
|---|---|---|---|---|---|---|---|---|---|---|---|
| Leu | His | Glu | His | His | Ile | Phe | Leu | Gly | Ala | Thr | Asn | Tyr | Ile | Tyr | Val |
| 1 | | | | 5 | | | | | 10 | | | | | 15 | |

Leu His Glu His His Ile Phe Leu Gly Ala Thr Asn Tyr Ile Tyr Val
 1               5                  10                  15

Leu Asn Glu Glu Asp Leu Gln Lys Val Ala Glu Tyr Lys Thr Gly Pro
                20                  25                  30

Val Leu Glu His Pro Asp Cys Phe Pro Cys Gln Asp Cys Ser Ser Lys
            35                  40                  45

Ala Asn Leu Ser Gly Gly Val Trp Lys Asp Asn Ile Asn Met Ala Leu
        50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
                100                 105                 110

Pro Ser Gln Cys Pro Asp Cys Val Val Ser Ala Leu Gly Ala Lys Val
            115                 120                 125

Leu Ser Ser Val Lys Asp Arg Phe Ile Asn Phe Val Gly Asn Thr
        130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
370                 375                 380

```
Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
            405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
            435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
 1                5                  10                  15

Gly Leu Gly Cys Arg His Phe Gln Ser Cys Ser Gln Cys Leu Ser Ala
                20                  25                  30

Pro Pro Phe Val Gln Cys Gly Trp Cys His Asp Lys Cys Val Arg Ser
            35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
                100                 105                 110

Thr Leu Ser Glu Ser Thr Met Asn Thr Leu Lys Cys Thr Val Gly Pro
            115                 120                 125

Ala Met Asn Lys His Phe Asn Met Ser Ile Ile Ser Asn Gly His
            130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
                180                 185                 190

Gly Gly Lys Thr Cys Thr Leu Lys Ser Val Ser Asn Ser Ile Leu Glu
            195                 200                 205

Cys Tyr Thr Pro Ala Gln Thr Ile Ser Thr Glu Phe Ala Val Lys Leu
210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
            275                 280                 285

Ser Val Pro Arg Met Val Ile Asn Val His Glu Ala Gly Arg Asn Phe
            290                 295                 300
```

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
            325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
            355                 360                 365

Ser Met Gly Asn Glu Asn Val Leu Glu Ile Lys Gly Asn Asp Ile Asp
            370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
                420                 425                 430

Ile Ser Ser Thr Val Leu Gly Lys Val Ile Val Gln Pro Asp Gln Asn
                435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

```
Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Glu Val Asp Thr
    290                 295                 300

Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain
      of c-Met

<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata gaagagccca gccagtgtcc tgactgtgtg     360
gtgagcgccc tgggagccaa agtcctttca tctgtaaagg accggttcat caacttcttt     420
gtaggcaata ccataaaatt ttcttatttc ccagatcatc cattgcattc gatatcagtg     480
agaaggctaa aggaaacgaa agatggtttt atgttttga cggaccagtc ctacattgat     540
gttttacctg agttcagaga ttcttacccc attaagtatg tccatgcctt tgaaagcaac     600
aattttattt acttcttgac ggtccaaagg gaaactctag atgctcagac ttttcacaca     660
agaataatca ggttctgttc cataaactct ggattgcatt cctacatgga aatgcctctg     720
gagtgtattc tcacagaaaa gagaaaaaag agatccacaa gaaggaagt gtttaatata     780 cttcaggctg cgtatgtcag caagcctggg gcccagcttg ctagacaaat aggagccagc     840
ctgaatgatg acattctttt cggggtgttc gcacaaagca agccagattc tgccgaacca     900
atggatcgat ctgccatgtg tgcattccct atcaaatatg tcaacgactt cttcaacaag     960
atcgtcaaca aaaacaatgt gagatgtctc cagcattttt acggacccaa tcatgagcac    1020
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aaccctcat    1260 gtgaatttc tcctggactc ccatccagtg tctccagaag tgattgtgga gcatacatta    1320
aaccaaaatg gc                                                      1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
      domain of c-Met

<400> SEQUENCE: 83

```
tacacactgg ttatcactgg gaagaagatc acgaagatcc cattgaatgg cttgggctgc      60
agacatttcc agtcctgcag tcaatgcctc tctgccccac cctttgttca gtgtggctgg     120
tgccacgaca aatgtgtgcg atcggaggaa tgcctgagcg ggacatggac tcaacagatc     180
tgtctgcctg caatctacaa ggttttccca aatagtgcac cccttgaagg agggacaagg     240
ctgaccatat gtggctggga ctttggattt cggaggaata taaatttga tttaaagaaa      300
actagagttc tccttggaaa tgagagctgc accttgactt aagtgagag cacgatgaat      360
acattgaaat gcacagttgg tcctgccatg aataagcatt tcaatatgtc cataattatt     420
tcaaatggcc acgggacaac acaatacagt acattctcct atgtggatcc tgtaataaca     480
agtatttcgc cgaaatacgg tcctatggct ggtggcactt tacttacttt aactggaaat     540
tacctaaaca gtgggaattc tagacacatt tcaattggtg aaaaacatg tactttaaaa      600
agtgtgtcaa acagtattct tgaatgttat accccagccc aaaccatttc aactgagttt     660
gctgttaaat tgaaaattga cttagccaac cgagagacaa gcatcttcag ttaccgtgaa     720
gatcccattg tctatgaaat tcatccaacc aaatctttta ttagtggtgg gagcacaata    780
acaggtgttg ggaaaaacct gaattcagtt agtgtcccga gaatggtcat aaatgtgcat    840
gaagcaggaa ggaactttac agtggcatgt caacatcgct ctaattcaga gataatctgt    900
tgtaccactc cttccctgca acagctgaat ctgcaactcc ccctgaaaac caaagccttt    960
ttcatgttag atgggatcct ttccaaatac tttgatctca tttatgtaca taatcctgtg   1020
tttaagcctt ttgaaaagcc agtgatgatc tcaatgggca atgaaaatgt actgaaaatt   1080
aagggaaatg atattgaccc tgaagcagtt aaaggtgaag tgttaaaagt tggaaataag   1140
agctgtgaga atatacactt acattctgaa gccgttttat gcacggtccc caatgacctg   1200
ctgaaattga acagcgagct aaatatagag tggaagcaag caatttcttc aaccgtcctt   1260
ggaaaagtaa tagttcaacc agatcagaat ttcacagga                           1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain
      of c-Met

<400> SEQUENCE: 84

```
gtgcatttca atgaagtcat aggaagaggg cattttggtt gtgtatatca tgggactttg      60
ttggacaatg atggcaagaa aattcactgt gctgtgaaat ccttgaacag aatcactgac     120
ataggagaag tttcccaatt tctgaccgag ggaatcatca tgaaagattt tagtcatccc     180
aatgtcctct cgctcctggg aatctgcctg cgaagtgaag ggtctccgct ggtggtccta     240
ccatacatga acatggagag tcttcgaaat tcattcgaa atgagactca taatccaact      300
gtaaagatc ttattggctt tggtcttcaa gtagccaaag gcatgaaata tcttgcaagc     360
aaaaagtttg tccacagaga cttggctgca agaaactgta tgctggatga aaaattcaca     420
```

```
gtcaaggttg ctgattttgg tcttgccaga gacatgtatg ataaagaata ctatagtgta    480
cacaacaaaa caggtgcaaa gctgccagtg aagtggatgg ctttggaaag tctgcaaact    540
caaaagttta ccaccaagtc agatgtgtgg tcctttggcg tgctcctctg ggagctgatg    600
acaagaggag ccccacctta tcctgacgta aacacctttg atataactgt ttacttgttg    660
caagggagaa gactcctaca acccgaatac tgcccagacc ccttatatga agtaatgcta    720
aaatgctggc ccctaaagc cgaaatgcgc ccatccttt ctgaactggt gtcccggata    780
tcagcgatct tctctacttt cattggggag cactatgtcc atgtgaacgc tacttatgtg    840
aacgtaaaat gtgtcgctcc gtatccttct ctgttgtcat cagaagataa cgctgatgat    900
gaggtggaca cacgaccagc ctccttctgg gagacatca                          939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met
      antibody

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

```
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of anti-
      c-Met antibody

<400> SEQUENCE: 88

Asp Ile Leu Met Thr Gln Ser Pro Ser Ser Leu Thr Val Ser Ala Gly
  1               5                  10                  15

Glu Lys Val Thr Met Ser Cys Lys Ser Ser Gln Ser Leu Leu Ala Ser
                 20                  25                  30

Gly Asn Gln Asn Asn Tyr Leu Ala Trp His Gln Gln Lys Pro Gly Arg
             35                  40                  45

Ser Pro Lys Met Leu Ile Ile Trp Ala Ser Thr Arg Val Ser Gly Val
         50                  55                  60

Pro Asp Arg Phe Ile Gly Ser Gly Ser Gly Thr Asp Phe Thr Leu Thr
 65                  70                  75                  80

Ile Asn Ser Val Gln Ala Glu Asp Leu Ala Val Tyr Tyr Cys Gln Gln
                 85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
  1               5                  10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
                 20                  25                  30

Tyr Met Ser Trp Val Arg Gln Pro Pro Gly Lys Gly Leu Glu Trp Leu
             35                  40                  45

Gly Phe Ile Arg Asn Lys Ala Asn Gly Tyr Thr Thr Glu Tyr Ser Ala
         50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Ser Ala Thr Tyr
                 85                  90                  95
```

```
Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
```

<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser

```
                20                  25                  30
Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

Asp Ile Leu Met Thr Gln Ser Pro Ser Ser Leu Thr Ala Ser Val Gly
1               5                   10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

```
Ser Tyr Ser Ala Pro Leu Thr Phe Gly Gln Gly Thr Lys Leu Glu Ile
                100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

Asp Ile Gln Met Thr Gln Ser Pro Ser Ser Leu Ser Ala Ser Val Gly
  1               5                  10                  15

Asp Arg Val Thr Ile Thr Cys Lys Ser Gln Ser Leu Leu Ala Ser
                 20                  25                  30

Gly Asn Gln Asn Asn Tyr Leu Ala Trp His Gln Gln Lys Pro Gly Lys
             35                  40                  45

Ala Pro Lys Met Leu Ile Ile Trp Ala Ser Thr Arg Val Ser Gly Val
     50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
                100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
  1               5                  10                  15

Asp Arg Val Thr Ile Thr Cys Lys Ser Gln Ser Leu Leu Ala Ser
                 20                  25                  30

Gly Asn Gln Asn Asn Tyr Leu Ala Trp His Gln Gln Lys Pro Gly Lys
             35                  40                  45

Ala Pro Lys Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
                100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)
```

<400> SEQUENCE: 100

Glu Pro Ser Cys Asp Lys His Cys Pro Pro Cys Pro
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

Glu Pro Lys Ser Cys Asp Cys His Cys Pro Pro Cys Pro
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
 1               5                  10

<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
 1               5                  10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
 1               5                  10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y -continued

<400> SEQUENCE: 106

Lys Ser Ser Gln Ser Leu Leu Ala Trp Gly Asn Gln Asn Asn Tyr Leu
 1               5                  10                  15
Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
             20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
             20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 109
<211> LENGTH: 6
<212> TYPE: PRT
<213> ORGANISM: Artificial Sequence
<220> FEATURE:
<223> OTHER INFORMATION: Synthetic CDR-H1 of anti-Ang2 antibody

<400> SEQUENCE: 109

Ser Asp Tyr Ala Trp Asn
1               5

<210> SEQ ID NO 110
<211> LENGTH: 16
<212> TYPE: PRT
<213> ORGANISM: Artificial Sequence
<220> FEATURE:
<223> OTHER INFORMATION: Synthetic CDR-H2 of anti-Ang2 antibody

<400> SEQUENCE: 110

Tyr Ile Asn Tyr Ser Gly Asn Thr Asp Tyr Asn Pro Ser Leu Lys Ser
1               5                   10                  15

<210> SEQ ID NO 111
<211> LENGTH: 9
<212> TYPE: PRT
<213> ORGANISM: Artificial Sequence
<220> FEATURE:
<223> OTHER INFORMATION: Synthetic CDR-H3 of anti-Ang2 antibody

<400> SEQUENCE: 111

Gly Asn Phe Glu Gly Ala Met Asp Tyr
1               5

<210> SEQ ID NO 112
<211> LENGTH: 11
<212> TYPE: PRT
<213> ORGANISM: Artificial Sequence
<220> FEATURE:
<223> OTHER INFORMATION: Synthetic CDR-L1 of anti-Ang2 antibody

<400> SEQUENCE: 112

Lys Ala Ser Gln Ser Val Ser Asn Asp Val Ala
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Synthetic CDR-L2 of anti-Ang2 antibody

<400> SEQUENCE: 113

Tyr Ala Ser Asn Arg Tyr Pro
1               5
```

<210> SEQ ID NO 114
<211> LENGTH: 9
<212> TYPE: PRT
<213> ORGANISM: Artificial Sequence
<220> FEATURE:
<223> OTHER INFORMATION: Synthetic CDR-L3 of anti-Ang2 antibody

<400> SEQUENCE: 114

Gln Gln Asp Tyr Ser Ser Pro Trp Thr
 1               5

<210> SEQ ID NO 115
<211> LENGTH: 118
<212> TYPE: PRT
<213> ORGANISM: Artificial Sequence
<220> FEATURE:
<223> OTHER INFORMATION: Synthetic Amino acid sequence of heavy chain
      variable region

<400> SEQUENCE: 115

Asp Val Gln Leu Gln Glu Ser Gly Pro Asp Leu Val Lys Pro Ser Gln
 1               5                  10                  15

Ser Leu Ser Leu Thr Cys Thr Val Thr Gly Tyr Ser Ile Thr Ser Asp
             20                  25                  30

Tyr Ala Trp Asn Trp Ile Arg Gln Phe Pro Gly Asn Lys Leu Glu Trp
         35                  40                  45

Met Gly Tyr Ile Asn Tyr Ser Gly Asn Thr Asp Tyr Asn Pro Ser Leu
     50                  55                  60

Lys Ser Arg Ser Ser Ile Thr Arg Asp Thr Ser Lys Asn Gln Phe Phe
 65                  70                  75                  80

Leu Gln Leu Asn Ser Val Thr Thr Gly Asp Thr Ala Thr Tyr Tyr Cys
                 85                  90                  95

Ala Arg Gly Asn Phe Glu Gly Ala Met Asp Tyr Trp Gly Gln Gly Thr
            100                 105                 110

Ser Val Thr Val Ser Ser
        115

<210> SEQ ID NO 116
<211> LENGTH: 354
<212> TYPE: DNA
<213> ORGANISM: Artificial Sequence
<220> FEATURE:
<223> OTHER INFORMATION: Synthetic Nucleotide sequence encoding heavy
      chain variable region

<400> SEQUENCE: 116
gatgtgcagc ttcaggagtc gggacctgac ctggtgaaac cttctcagtc tctgtccctc      60
acctgcactg tcactggcta ctcaatcacc agtgattatg cctggaactg gatccggcag     120
tttccaggaa acaaactgga gtggatgggc tacataaact acagtggtaa cactgactac     180
aacccatctc tcaaaagtcg aagctctatc actcgagaca catccaagaa ccagttcttc     240
ctgcagttga attctgtgac tactggggac acagccacat attactgtgc aagaggtaac     300
ttcgaaggtg ctatggacta ctggggtcaa ggaacctcag tcaccgtctc ctca           354

<210> SEQ ID NO 117
<211> LENGTH: 107
<212> TYPE: PRT
<213> ORGANISM: Artificial Sequence
<220> FEATURE:
<223> OTHER INFORMATION: Synthetic Amino acid sequence of light chain variable region

<400> SEQUENCE: 117

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Pro Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 118
<211> LENGTH: 321
<212> TYPE: DNA
<213> ORGANISM: Artificial Sequence
<220> FEATURE:
<223> OTHER INFORMATION: Synthetic Nucleotide sequence emcoding light
      chain variable region

<400> SEQUENCE: 118
agtattgtga tgacccagac tcccaaattc ctgcttgtat cagcaggaga cagggttacc      60
ataacctgca aggccagtca gagtgtgagt aatgatgtag cttggtacca acagaagcca     120
gggcagtctc ctaaactgct gatatactat gcatccaatc gctacctgg agtccctgat      180 cgcttcactg gcagtggata tgggacggat ttcactttca ccatcagcac tgtgcaggct     240
gaagacctgg cagtttattt ctgtcagcag gattatagct ctccgtggac gttcggtgga     300
ggcaccaagc tggaaatcaa a                                                321

<210> SEQ ID NO 119
<211> LENGTH: 496
<212> TYPE: PRT
<213> ORGANISM: Artificial Sequence
<220> FEATURE:
<223> OTHER INFORMATION: Synthetic Human Ang2

<400> SEQUENCE: 119

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

```
Gln Gln Asn Ala Val Gln Asn Thr Ala Val Met Ile Glu Ile Gly
            115                 120                 125
Thr Asn Leu Leu Asn Gln Thr Ala Glu Gln Thr Arg Lys Leu Thr Asp
        130                 135                 140
Val Glu Ala Gln Val Leu Asn Gln Thr Thr Arg Leu Glu Leu Gln Leu
145                 150                 155                 160
Leu Glu His Ser Leu Ser Thr Asn Lys Leu Glu Lys Gln Ile Leu Asp
                165                 170                 175
Gln Thr Ser Glu Ile Asn Lys Leu Gln Asp Lys Asn Ser Phe Leu Glu
            180                 185                 190
Lys Lys Val Leu Ala Met Glu Asp Lys His Ile Ile Gln Leu Gln Ser
        195                 200                 205
Ile Lys Glu Glu Lys Asp Gln Leu Gln Val Leu Val Ser Lys Gln Asn
    210                 215                 220
Ser Ile Ile Glu Glu Leu Glu Lys Lys Ile Val Thr Ala Thr Val Asn
225                 230                 235                 240
Asn Ser Val Leu Gln Lys Gln Gln His Asp Leu Met Glu Thr Val Asn
                245                 250                 255
Asn Leu Leu Thr Met Met Ser Thr Ser Asn Ser Ala Lys Asp Pro Thr
            260                 265                 270
Val Ala Lys Glu Glu Gln Ile Ser Phe Arg Asp Cys Ala Glu Val Phe
        275                 280                 285
Lys Ser Gly His Thr Thr Asn Gly Ile Tyr Thr Leu Thr Phe Pro Asn
    290                 295                 300
Ser Thr Glu Glu Ile Lys Ala Tyr Cys Asp Met Glu Ala Gly Gly Gly
305                 310                 315                 320
Gly Trp Thr Ile Ile Gln Arg Arg Glu Asp Gly Ser Val Asp Phe Gln
                325                 330                 335
Arg Thr Trp Lys Glu Tyr Lys Val Gly Phe Gly Asn Pro Ser Gly Glu
            340                 345                 350
Tyr Trp Leu Gly Asn Glu Phe Val Ser Gln Leu Thr Asn Gln Gln Arg
        355                 360                 365
Tyr Val Leu Lys Ile His Leu Lys Asp Trp Glu Gly Asn Glu Ala Tyr
    370                 375                 380
Ser Leu Tyr Glu His Phe Tyr Leu Ser Ser Glu Glu Leu Asn Tyr Arg
385                 390                 395                 400
Ile His Leu Lys Gly Leu Thr Gly Thr Ala Gly Lys Ile Ser Ser Ile
                405                 410                 415
Ser Gln Pro Gly Asn Asp Phe Ser Thr Lys Asp Gly Asp Asn Asp Lys
            420                 425                 430
Cys Ile Cys Lys Cys Ser Gln Met Leu Thr Gly Gly Trp Trp Phe Asp
        435                 440                 445
Ala Cys Gly Pro Ser Asn Leu Asn Gly Met Tyr Tyr Pro Gln Arg Gln
    450                 455                 460
Asn Thr Asn Lys Phe Asn Gly Ile Lys Trp Tyr Tyr Trp Lys Gly Ser
465                 470                 475                 480
Gly Tyr Ser Leu Lys Ala Thr Thr Met Met Ile Arg Pro Ala Asp Phe
                485                 490                 495

<210> SEQ ID NO 120
<211> LENGTH: 121
<212> TYPE: PRT
<213> ORGANISM: Artificial Sequence
<220> FEATURE:
<223> OTHER INFORMATION: Synthetic Amino acid sequence of heavy chain
``` variable region (4H10)

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Leu Ile Ser Pro Asp Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ile Ser Phe Trp Arg Gly Phe Asp Tyr Trp Gly
            100                 105                 110

Gln Gly Thr Leu Val Thr Val Ser Ser
        115                 120

<210> SEQ ID NO 121
<211> LENGTH: 111
<212> TYPE: PRT
<213> ORGANISM: Artificial Sequence
<220> FEATURE:
<223> OTHER INFORMATION: Synthetic Amino acid sequence of light chain
      variable region (4H10)

<400> SEQUENCE: 121

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 122
<211> LENGTH: 16
<212> TYPE: PRT
<213> ORGANISM: Artificial Sequence
<220> FEATURE:
<223> OTHER INFORMATION: Synthetic CDR-H2 of anti-Ang2 antibody

<400> SEQUENCE: 122

Lys Ile Ser Tyr Ser Gly Lys Thr Asp Tyr Asn Pro Ser Leu Lys Ser
1               5                   10                  15

<210> SEQ ID NO 123
<211> LENGTH: 16
<212> TYPE: PRT
<213> ORGANISM: Artificial Sequence
<220> FEATURE:

<223> OTHER INFORMATION: Synthetic CDR-H2 of anti-Ang2 antibody

<400> SEQUENCE: 123

Lys Ile Asn Tyr Ala Gly Asn Thr Asp Tyr Asn Pro Ser Leu Lys Ser
 1               5                  10                  15

<210> SEQ ID NO 124
<211> LENGTH: 11
<212> TYPE: PRT
<213> ORGANISM: Artificial Sequence
<220> FEATURE:
<223> OTHER INFORMATION: Synthetic CDR-L1 of anti-Ang2 antibody

<400> SEQUENCE: 124

Lys Ala Ser Gln Ser Val Ser Asn Asp Val His
 1               5                  10

<210> SEQ ID NO 125
<211> LENGTH: 11
<212> TYPE: PRT
<213> ORGANISM: Artificial Sequence
<220> FEATURE:
<223> OTHER INFORMATION: Synthetic CDR-L1 of anti-Ang2 antibody

<400> SEQUENCE: 125

Lys Ala Ser Gln Phe Val Ser Thr Asp Val His
 1               5                  10

<210> SEQ ID NO 126
<211> LENGTH: 7
<212> TYPE: PRT
<213> ORGANISM: Artificial Sequence
<220> FEATURE:
<223> OTHER INFORMATION: Synthetic CDR-L2 of anti-Ang2 antibody

<400> SEQUENCE: 126

Tyr Ala Ser Ile Pro Tyr Pro
 1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic CDR-L3 of anti-Ang2 antibody

<400> SEQUENCE: 127

Gln His Asp Tyr Ser Ser Pro Phe Thr
 1               5

<210> SEQ ID NO 128
<211> LENGTH: 16
<212> TYPE: PRT
<213> ORGANISM: Artificial Sequence
<220> FEATURE:
<223> OTHER INFORMATION: Synthetic CDR-H2 of anti-Ang2 antibody
<220> FEATURE:
<221> NAME/KEY: MOD_RES
<222> LOCATION: (1)
<223> OTHER INFORMATION: Xaa is Tyr (Y) or Lys (K)
<220> FEATURE:
<221> NAME/KEY: MOD_RES
<222> LOCATION: (3)
<223> OTHER INFORMATION: Xaa is Asn (N) or Ser (S)
<220> FEATURE:
<221> NAME/KEY: MOD_RES
<222> LOCATION: (5)
<223> OTHER INFORMATION: Xaa is Ser (S) or Ala (A)
<220> FEATURE:

```
<221> NAME/KEY: MOD_RES
<222> LOCATION: (7)
<223> OTHER INFORMATION: Xaa is Asn (N) or Lys (K)

<400> SEQUENCE: 128

Xaa Ile Xaa Tyr Xaa Gly Xaa Thr Asp Tyr Asn Pro Ser Leu Lys Ser
 1               5                  10                  15

<210> SEQ ID NO 129
<211> LENGTH: 11
<212> TYPE: PRT
<213> ORGANISM: Artificial Sequence
<220> FEATURE:
<223> OTHER INFORMATION: Synthetic CDR-L1 of anti-Ang2 antibody
<220> FEATURE:
<221> NAME/KEY: MOD_RES
<222> LOCATION: (5)
<223> OTHER INFORMATION: Xaa is Ser (S) or Phe (F)
<220> FEATURE:
<221> NAME/KEY: MOD_RES
<222> LOCATION: (8)
<223> OTHER INFORMATION: Xaa is Asn (N) or Thr (T)
<220> FEATURE:
<221> NAME/KEY: MOD_RES
<222> LOCATION: (11)
<223> OTHER INFORMATION: Xaa is Ala (A) or His (H)

<400> SEQUENCE: 129

Lys Ala Ser Gln Xaa Val Ser Xaa Asp Val Xaa
 1               5                  10

<210> SEQ ID NO 130
<211> LENGTH: 7
<212> TYPE: PRT
<213> ORGANISM: Artificial Sequence
<220> FEATURE:
<223> OTHER INFORMATION: Synthetic CDR-L2 of anti-Ang2 antibody
<220> FEATURE:
<221> NAME/KEY: MOD_RES
<222> LOCATION: (4)
<223> OTHER INFORMATION: Xaa is Asn (N) or Ile (I)
<220> FEATURE:
<221> NAME/KEY: MOD_RES
<222> LOCATION: (5)
<223> OTHER INFORMATION: Xaa is Arg (R) or Pro (P)

<400> SEQUENCE: 130

Tyr Ala Ser Xaa Xaa Tyr Pro
 1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic CDR-L3 of anti-Ang2 antibody
<220> FEATURE:
<221> NAME/KEY: MOD_RES
<222> LOCATION: (2)
<223> OTHER INFORMATION: Xaa is Gln (Q) or His (H)
<220> FEATURE:
<221> NAME/KEY: MOD_RES
<222> LOCATION: (8)
<223> OTHER INFORMATION: Xaa is Trp (W) or Phe (F)

<400> SEQUENCE: 131

Gln Xaa Asp Tyr Ser Ser Pro Xaa Thr
 1               5

<210> SEQ ID NO 132
<211> LENGTH: 30
```

```
<212> TYPE: PRT
<213> ORGANISM: Artificial Sequence
<220> FEATURE:
<223> OTHER INFORMATION: Synthetic FR1 (N-terminal frame region of CDR-
      H1 of 10D6)

<400> SEQUENCE: 132

Asp Val Gln Leu Gln Glu Ser Gly Pro Asp Leu Val Lys Pro Ser Gln
 1               5                  10                  15

Ser Leu Ser Leu Thr Cys Thr Val Thr Gly Tyr Ser Ile Thr
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Synthetic FR1 (N-terminal frame region of CDR-
      H1 of VH-hu1)

<400> SEQUENCE: 133

Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser
            20                  25                  30

<210> SEQ ID NO 134
<211> LENGTH: 30
<212> TYPE: PRT
<213> ORGANISM: Artificial Sequence
<220> FEATURE:
<223> OTHER INFORMATION: Synthetic FR1 (N-terminal frame region of CDR-
      H1 of VH-hu2)

<400> SEQUENCE: 134

Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr
            20                  25                  30

<210> SEQ ID NO 135
<211> LENGTH: 30
<212> TYPE: PRT
<213> ORGANISM: Artificial Sequence
<220> FEATURE:
<223> OTHER INFORMATION: Synthetic FR1 (N-terminal frame region of CDR-
      H1 of VH-hu5)

<400> SEQUENCE: 135

Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr
            20                  25                  30

<210> SEQ ID NO 136
<211> LENGTH: 30
<212> TYPE: PRT
<213> ORGANISM: Artificial Sequence
<220> FEATURE:
<223> OTHER INFORMATION: Synthetic FR1 (N-terminal frame region of CDR-
      H1 of VH-hu3)

<400> SEQUENCE: 136

Glu Val Gln Leu Val Glu Ser Gly Gly Gly Leu Val Gln Pro Gly Gly
 1               5                  10                  15
```

-continued

Ser Leu Arg Leu Ser Cys Ala Ala Ser Gly Tyr Ser Ile Thr
            20                  25                  30

<210> SEQ ID NO 137
<211> LENGTH: 14
<212> TYPE: PRT
<213> ORGANISM: Artificial Sequence
<220> FEATURE:
<223> OTHER INFORMATION: Synthetic FR2 (frame region between CDR-H1 and
      CDR-H2 of 10D6)

<400> SEQUENCE: 137

Trp Ile Arg Gln Phe Pro Gly Asn Lys Leu Glu Trp Met Gly
 1               5                  10

<210> SEQ ID NO 138
<211> LENGTH: 14
<212> TYPE: PRT
<213> ORGANISM: Artificial Sequence
<220> FEATURE:
<223> OTHER INFORMATION: Synthetic FR2 (frame region between CDR-H1 and
      CDR-H2 of VH-hu1)

<400> SEQUENCE: 138

Trp Ile Arg Gln Pro Pro Gly Lys Gly Leu Glu Trp Ile Gly
 1               5                  10

<210> SEQ ID NO 139
<211> LENGTH: 14
<212> TYPE: PRT
<213> ORGANISM: Artificial Sequence
<220> FEATURE:
<223> OTHER INFORMATION: Synthetic FR2 (frame region between CDR-H1 and
      CDR-H2 of VH-hu2)

<400> SEQUENCE: 139

Trp Ile Arg Gln Pro Pro Gly Lys Gly Leu Glu Trp Met Gly
 1               5                  10

<210> SEQ ID NO 140
<211> LENGTH: 14
<212> TYPE: PRT
<213> ORGANISM: Artificial Sequence
<220> FEATURE:
<223> OTHER INFORMATION: Synthetic FR2 (frame region between CDR-H1 and
      CDR-H2 of VH-hu5)

<400> SEQUENCE: 140

Trp Ile Arg Gln Pro Pro Gly Lys Gly Leu Glu Trp Ile Gly
 1               5                  10

<210> SEQ ID NO 141
<211> LENGTH: 14
<212> TYPE: PRT
<213> ORGANISM: Artificial Sequence
<220> FEATURE:
<223> OTHER INFORMATION: Synthetic FR2 (frame region between CDR-H1
      and CDR-H2 of VH-hu3)

<400> SEQUENCE: 141

Trp Val Arg Gln Ala Pro Gly Lys Gly Leu Glu Trp Met Gly
 1               5                  10

<210> SEQ ID NO 142
<211> LENGTH: 32
<212> TYPE: PRT
<213> ORGANISM: Artificial Sequence
<220> FEATURE:

```
<223> OTHER INFORMATION: Synthetic FR3 (frame region between CDR-H2
      and CDR-H3 of 10D6)

<400> SEQUENCE: 142

Arg Ser Ser Ile Thr Arg Asp Thr Ser Lys Asn Gln Phe Phe Leu Gln
1               5                   10                  15

Leu Asn Ser Val Thr Thr Gly Asp Thr Ala Thr Tyr Tyr Cys Ala Arg
            20                  25                  30

<210> SEQ ID NO 143
<211> LENGTH: 32
<212> TYPE: PRT
<213> ORGANISM: Artificial Sequence
<220> FEATURE:
<223> OTHER INFORMATION: Synthetic FR3 (frame region between CDR-H2
      and CDR-H3 of VH-hu1)

<400> SEQUENCE: 143

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 144
<211> LENGTH: 32
<212> TYPE: PRT
<213> ORGANISM: Artificial Sequence
<220> FEATURE:
<223> OTHER INFORMATION: Synthetic FR3 (frame region between CDR-H2 and
      CDR-H3 of VH-hu2)

<400> SEQUENCE: 144

Arg Ser Thr Ile Ser Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 145
<211> LENGTH: 32
<212> TYPE: PRT
<213> ORGANISM: Artificial Sequence
<220> FEATURE:
<223> OTHER INFORMATION: Synthetic FR3 (frame region between CDR-H2 and
      CDR-H3 of VH-hu5)

<400> SEQUENCE: 145

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: Synthetic FR3 (frame region between CDR-H2 and
      CDR-H3 of VH-hu3)

<400> SEQUENCE: 146

Arg Ser Thr Ile Ser Arg Asp Thr Ser Lys Asn Thr Phe Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 147
<211> LENGTH: 11
<212> TYPE: PRT
<213> ORGANISM: Artificial Sequence
<220> FEATURE:
<223> OTHER INFORMATION: Synthetic FR4 (C-terminal frame region of CDR-H3 of 10D6)

<400> SEQUENCE: 147

Trp Gly Gln Gly Thr Ser Val Thr Val Ser Ser
 1               5                  10

<210> SEQ ID NO 148
<211> LENGTH: 11
<212> TYPE: PRT
<213> ORGANISM: Artificial Sequence
<220> FEATURE:
<223> OTHER INFORMATION: Synthetic FR4 (C-terminal frame region of CDR-H3 of VH-hu1)

<400> SEQUENCE: 148

Trp Gly Gln Gly Thr Leu Val Thr Val Ser Ser
 1               5                  10

<210> SEQ ID NO 149
<211> LENGTH: 11
<212> TYPE: PRT
<213> ORGANISM: Artificial Sequence
<220> FEATURE:
<223> OTHER INFORMATION: Synthetic FR4 (C-terminal frame region of CDR-H3 of VH-hu2)

<400> SEQUENCE: 149

Trp Gly Gln Gly Thr Leu Val Thr Val Ser Ser
 1               5                  10

<210> SEQ ID NO 150
<211> LENGTH: 11
<212> TYPE: PRT
<213> ORGANISM: Artificial Sequence
<220> FEATURE:
<223> OTHER INFORMATION: Synthetic FR4 (C-terminal frame region of CDR-H3 of VH-hu5)

<400> SEQUENCE: 150

Trp Gly Gln Gly Thr Leu Val Thr Val Ser Ser
 1               5                  10

<210> SEQ ID NO 151
<211> LENGTH: 11
<212> TYPE: PRT
<213> ORGANISM: Artificial Sequence
<220> FEATURE:
<223> OTHER INFORMATION: Synthetic FR4 (C-terminal frame region of CDR-H3 of VH-hu3)

<400> SEQUENCE: 151

Trp Gly Gln Gly Thr Leu Val Thr Val Ser Ser
 1               5                  10

<210> SEQ ID NO 152
<211> LENGTH: 23
<212> TYPE: PRT
<213> ORGANISM: Artificial Sequence
<220> FEATURE:
<223> OTHER INFORMATION: Synthetic FR1 (N-terminal frame region of CDR-L1 of 10D6)

```
<400> SEQUENCE: 152

Ser Ile Val Met Thr Gln Thr Pro Lys Phe Leu Leu Val Ser Ala Gly
  1               5                  10                  15

Asp Arg Val Thr Ile Thr Cys
             20

<210> SEQ ID NO 153
<211> LENGTH: 23
<212> TYPE: PRT
<213> ORGANISM: Artificial Sequence
<220> FEATURE:
<223> OTHER INFORMATION: Synthetic FR1 (N-terminal frame region of CDR-
      L1 of VL-hu1)

<400> SEQUENCE: 153

Asp Ile Gln Met Thr Gln Ser Pro Ser Ser Leu Ser Ala Ser Val Gly
  1               5                  10                  15

Asp Arg Val Thr Ile Thr Cys
             20

<210> SEQ ID NO 154
<211> LENGTH: 15
<212> TYPE: PRT
<213> ORGANISM: Artificial Sequence
<220> FEATURE:
<223> OTHER INFORMATION: Synthetic FR2 (frame region between CDR-L1 and
      CDR-L2 of 10D6)

<400> SEQUENCE: 154

Trp Tyr Gln Gln Lys Pro Gly Gln Ser Pro Lys Leu Leu Ile Tyr
  1               5                  10                  15

<210> SEQ ID NO 155
<211> LENGTH: 15
<212> TYPE: PRT
<213> ORGANISM: Artificial Sequence
<220> FEATURE:
<223> OTHER INFORMATION: Synthetic FR2 (frame region between CDR-L1 and
      CDR-L2 of VL-hu1)

<400> SEQUENCE: 155

Trp Tyr Gln Gln Lys Pro Gly Lys Ala Pro Lys Leu Leu Ile Tyr
  1               5                  10                  15

<210> SEQ ID NO 156
<211> LENGTH: 32
<212> TYPE: PRT
<213> ORGANISM: Artificial Sequence
<220> FEATURE:
<223> OTHER INFORMATION: Synthetic FR3 (frame region between CDR-L2 and
      CDR-L3 of 10D6)

<400> SEQUENCE: 156

Gly Val Pro Asp Arg Phe Thr Gly Ser Gly Tyr Gly Thr Asp Phe Thr
  1               5                  10                  15

Phe Thr Ile Ser Thr Val Gln Ala Glu Asp Leu Ala Val Tyr Phe Cys
             20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Synthetic FR3 (frame region between CDR-L2 and
      CDR-L3 of VL-hu1)
```

<400> SEQUENCE: 157

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 158
<211> LENGTH: 10
<212> TYPE: PRT
<213> ORGANISM: Artificial Sequence
<220> FEATURE:
<223> OTHER INFORMATION: Synthetic FR4 (C-terminal frame region of
      CDR-L3 of 10D6)

<400> SEQUENCE: 158

Phe Gly Gly Gly Thr Lys Leu Glu Ile Lys
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Synthetic FR4 (C-terminal frame region of
      CDR-L3 of VL-hu1)

<400> SEQUENCE: 159

Phe Gly Gln Gly Thr Lys Val Glu Ile Lys
1               5                   10

<210> SEQ ID NO 160
<211> LENGTH: 118
<212> TYPE: PRT
<213> ORGANISM: Artificial Sequence
<220> FEATURE:
<223> OTHER INFORMATION: Synthetic Heavy chain variable region

<400> SEQUENCE: 160

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
                20                  25                  30

Tyr Ala Trp Asn Trp Ile Arg Gln Pro Pro Gly Lys Gly Leu Glu Trp
            35                  40                  45

Met Gly Lys Ile Ser Tyr Ser Gly Lys Thr Asp Tyr Asn Pro Ser Leu
    50                  55                  60

Lys Ser Arg Ser Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Asn Phe Glu Gly Ala Met Asp Tyr Trp Gly Gln Gly Thr
            100                 105                 110

Leu Val Thr Val Ser Ser
        115

<210> SEQ ID NO 161
<211> LENGTH: 118
<212> TYPE: PRT
<213> ORGANISM: Artificial Sequence
<220> FEATURE:
<223> OTHER INFORMATION: Synthetic Heavy chain variable region

<400> SEQUENCE: 161

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Lys Ile Asn Tyr Ala Gly Asn Thr Asp Tyr Asn Pro Ser Leu
    50                  55                  60

Lys Ser Arg Ser Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Gly Asn Phe Glu Gly Ala Met Asp Tyr Trp Gly Gln Gly Thr
            100                 105                 110

Leu Val Thr Val Ser Ser
        115
```

<210> SEQ ID NO 162
<211> LENGTH: 118
<212> TYPE: PRT
<213> ORGANISM: Artificial Sequence
<220> FEATURE:
<223> OTHER INFORMATION: Synthetic Heavy chain variable region

<400> SEQUENCE: 162

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Met Gly Lys Ile Ser Tyr Ser Gly Lys Thr Asp Tyr Asn Pro Ser Leu
    50                  55                  60

Lys Ser Arg Ser Thr Ile Ser Arg Asp Thr Ser Lys Asn Thr Phe Tyr
 65                  70                  75                  80

Leu Gln Met Asn Ser Leu Arg Ala Glu Asp Thr Ala Val Tyr Tyr Cys
                85                  90                  95

Ala Arg Gly Asn Phe Glu Gly Ala Met Asp Tyr Trp Gly Gln Gly Thr
            100                 105                 110

Leu Val Thr Val Ser Ser
        115
```

<210> SEQ ID NO 163
<211> LENGTH: 118
<212> TYPE: PRT
<213> ORGANISM: Artificial Sequence
<220> FEATURE:
<223> OTHER INFORMATION: Synthetic Heavy chain variable region

<400> SEQUENCE: 163

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Met Gly Lys Ile Asn Tyr Ala Gly Asn Thr Asp Tyr Asn Pro Ser Leu
```

```
                    50                  55                  60
Lys Ser Arg Ser Thr Ile Ser Arg Asp Thr Ser Lys Asn Thr Phe Tyr
 65                  70                  75                  80

Leu Gln Met Asn Ser Leu Arg Ala Glu Asp Thr Ala Val Tyr Tyr Cys
                    85                  90                  95

Ala Arg Gly Asn Phe Glu Gly Ala Met Asp Tyr Trp Gly Gln Gly Thr
                100                 105                 110

Leu Val Thr Val Ser Ser
            115

<210> SEQ ID NO 164
<211> LENGTH: 118
<212> TYPE: PRT
<213> ORGANISM: Artificial Sequence
<220> FEATURE:
<223> OTHER INFORMATION: Synthetic Heavy chain variable region

<400> SEQUENCE: 164

Gln Val Gln Leu Gln Glu Ser Gly Pro Gly Leu Val Lys Pro Ser Glu
  1               5                  10                  15

Thr Leu Ser Leu Thr Cys Ala Val Ser Gly Tyr Ser Ile Thr Ser Asp
                 20                  25                  30

Tyr Ala Trp Asn Trp Ile Arg Gln Pro Pro Gly Lys Gly Leu Glu Trp
             35                  40                  45

Ile Gly Tyr Ile Asn Tyr Ser Gly Asn Thr Asp Tyr Asn Pro Ser Leu
         50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                    85                  90                  95

Ala Arg Gly Asn Phe Glu Gly Ala Met Asp Tyr Trp Gly Gln Gly Thr
                100                 105                 110

Leu Val Thr Val Ser Ser
            115

<210> SEQ ID NO 165
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 165

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Ser Val Ser Asn Asp
                 20                  25                  30

Val Ala Trp Tyr Gln Gln Lys Pro Gly Lys Ala Pro Lys Leu Leu Ile
             35                  40                  45

Tyr Tyr Ala Ser Asn Arg Tyr Pro Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Ser Ser Pro Trp
                    85                  90                  95

Thr Phe Gly Gln Gly Thr Lys Leu Glu Ile Lys
                100                 105
```

<210> SEQ ID NO 166
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 166

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Ser Asn Asp
            20                  25                  30

Val His Trp Tyr Gln Gln Lys Pro Gly Lys Ala Pro Lys Leu Leu Ile
        35                  40                  45

Tyr Tyr Ala Ser Asn Arg Tyr Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Leu Glu Ile Lys
            100                 105

<210> SEQ ID NO 167
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 167

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Ser Asn Asp
            20                  25                  30

Val His Trp Tyr Gln Gln Lys Pro Gly Lys Ala Pro Lys Leu Leu Ile
        35                  40                  45

Tyr Tyr Ala Ser Asn Arg Tyr Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Asp Tyr Ser Ser Pro Phe
                85                  90                  95

Thr Phe Gly Gln Gly Thr Lys Leu Glu Ile Lys
            100                 105

<210> SEQ ID NO 168
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 168

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Phe Val Ser Thr Asp
            20                  25                  30

Val His Trp Tyr Gln Gln Lys Pro Gly Lys Ala Pro Lys Leu Leu Ile

```
                35                  40                  45

Tyr Tyr Ala Ser Asn Arg Tyr Pro Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Ser Ser Pro Trp
                 85                  90                  95

Thr Phe Gly Gln Gly Thr Lys Leu Glu Ile Lys
            100                 105

<210> SEQ ID NO 169
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 169

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Ser Val Ser Asn Asp
                 20                  25                  30

Val Ala Trp Tyr Gln Gln Lys Pro Gly Lys Ala Pro Lys Leu Leu Ile
            35                  40                  45

Tyr Tyr Ala Ser Ile Pro Tyr Pro Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Ser Ser Pro Trp
                 85                  90                  95

Thr Phe Gly Gln Gly Thr Lys Leu Glu Ile Lys
            100                 105

<210> SEQ ID NO 170
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 170

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Ser Val Ser Asn Asp
                 20                  25                  30

Val His Trp Tyr Gln Gln Lys Pro Gly Lys Ala Pro Lys Leu Leu Ile
            35                  40                  45

Tyr Tyr Ala Ser Ile Pro Tyr Pro Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Ser Ser Pro Trp
                 85                  90                  95

Thr Phe Gly Gln Gly Thr Lys Leu Glu Ile Lys
            100                 105

<210> SEQ ID NO 171
<211> LENGTH: 107
```

<212> TYPE: PRT
<213> ORGANISM: Artificial Sequence
<220> FEATURE:
<223> OTHER INFORMATION: Synthetic Light chain variable resion

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Phe Val Ser Thr Asp
            20                  25                  30

Val His Trp Tyr Gln Gln Lys Pro Gly Lys Ala Pro Lys Leu Leu Ile
        35                  40                  45

Tyr Tyr Ala Ser Ile Pro Tyr Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Leu Glu Ile Lys
            100                 105

<210> SEQ ID NO 172
<211> LENGTH: 354
<212> TYPE: DNA
<213> ORGANISM: Artificial Sequence
<220> FEATURE:
<223> OTHER INFORMATION: Synthetic Coding sequence of heavy chain
      variable region(SEQ ID NO: 160)

<400> SEQUENCE: 172
caggtgcaac tgcaggagtc aggccccggc ctggtaaaac cttctgaaac gctctcactt      60
acctgtgccg ttagtggata tctctatcact tccgactacg cttggaattg gattcggcag    120
cctccaggca aagggctgga atggatggga aagatttcct attccggtaa gactgactac    180
aatcccagtc tgaagagcag gtcaacaatc tccagagaca ccagcaagaa tcagttttcc    240
ctgaaattgt cctcggtgac agcagcggat accgcagtgt attattgcgc ccgcggtaac    300
ttcgagggag ctatggatta ctgggggcag ggtactctcg tcactgtgag cagc           354

<210> SEQ ID NO 173
<211> LENGTH: 354
<212> TYPE: DNA
<213> ORGANISM: Artificial Sequence
<220> FEATURE:
<223> OTHER INFORMATION: Synthetic Coding sequence of heavy chain
      variable region(SEQ ID NO: 161)

<400> SEQUENCE: 173
caggtgcaac tgcaggagtc aggccccggc ctggtaaaac cttctgaaac gctctcactt      60
acctgtgccg ttagtggata tctctatcact tccgactacg cttggaattg gattcggcag    120
cctccaggca aagggctgga atggatggga aagattaact atgccggtaa cactgactac    180
aatcccagtc tgaagagcag gtcaacaatc tccagagaca ccagcaagaa tcagttttcc    240
ctgaaattgt cctcggtgac agcagcggat accgcagtgt attattgcgc ccgcggtaac    300
ttcgagggag ctatggatta ctgggggcag ggtactctcg tcactgtgag cagc           354

<210> SEQ ID NO 174
<211> LENGTH: 354
<212> TYPE: DNA
<213> ORGANISM: Artificial Sequence
<220> FEATURE:
<223> OTHER INFORMATION: Synthetic Coding sequence of heavy chain variable region(SEQ ID NO: 162)

<400> SEQUENCE: 174

| | |
|---|---:|
| gaggttcagc tggtcgaaag cggtgggga ctcgtgcagc caggcggttc tcttagatta | 60 |
| tcatgtgccg catccgggta ctccatcacc tctgattatg catggaactg ggtcagacaa | 120 |
| gcccccggaa agggcctgga gtggatgggg aagatctcct attcagggaa gacagattat | 180 |
| aatccttcgc tgaaaagcag atcaacaatt agtagagaca cttctaaaaa tacttttac | 240 |
| ctccagatga acagtctgcg cgccgaagac accgccgtgt actactgcgc taggggaaat | 300 |
| ttcgagggag ctatggacta ttggggccag ggcacgttgg taaccgtgag cagc | 354 |

<210> SEQ ID NO 175
<211> LENGTH: 354
<212> TYPE: DNA
<213> ORGANISM: Artificial Sequence
<220> FEATURE:
<223> OTHER INFORMATION: Synthetic Coding sequence of heavy chain variable region(SEQ ID NO: 163)

<400> SEQUENCE: 175

| | |
|---|---:|
| gaggttcaac tggtagagtc cgggggcggc ctggtccagc caggaggaag cctgcggctc | 60 |
| tcttgtgccg ccagcgggta tagtatcact tcagattatg cctggaattg ggtccgccag | 120 |
| gcccccggga agggcttaga gtggatgggt aaaattaatt acgcaggcaa caccgactat | 180 |
| aatccttcac tgaaatctag atccaccatc tctagagata caagtaagaa cacctttac | 240 |
| ttgcagatga atagcctcag ggctgaagac actgctgtgt actactgcgc aagaggaaac | 300 |
| ttcgaaggag cgatggatta ttggggccag ggtacgcttg tgacagtgtc ctct | 354 |

<210> SEQ ID NO 176
<211> LENGTH: 354
<212> TYPE: DNA
<213> ORGANISM: Artificial Sequence
<220> FEATURE:
<223> OTHER INFORMATION: Synthetic Coding sequence of heavy chain variable region(SEQ ID NO: 164)

<400> SEQUENCE: 176

| | |
|---|---:|
| caggtgcagc tgcaggagtc gggcccagga ctggtgaagc cttcggagac cctgtccctc | 60 |
| acctgcgctg tctctggtta ctccatcacc agtgattatg cctggaactg gatccggcag | 120 |
| cccccaggga aggggctgga gtggattggg tacataaact acagtggtaa cactgactac | 180 |
| aacccatctc tcaaaagtcg agtcaccata tcagtagaca cgtccaagaa ccagttctcc | 240 |
| ctgaagctga gctctgtgac cgccgcagac acggccgtgt attactgtgc gagaggtaac | 300 |
| ttcgaaggtg ctatggacta ctggggtcaa ggaacgcttg tgacagtgtc ctct | 354 |

<210> SEQ ID NO 177
<211> LENGTH: 321
<212> TYPE: DNA
<213> ORGANISM: Artificial Sequence
<220> FEATURE:
<223> OTHER INFORMATION: Synthetic Coding sequence of light chain variable region(SEQ ID NO: 165)

<400> SEQUENCE: 177

| | |
|---|---:|
| gacatccaga tgacccagtc tccatcctcc ctgtctgcat ctgtaggaga cagagtcacc | 60 |
| atcacttgca aggccagtca gagtgtgagt aatgatgtag cttggtatca gcagaaacca | 120 |

```
gggaaagccc ctaagctcct gatctattat gcatccaatc gctaccctgg ggtcccatca      180
aggttcagtg gcagtggatc tgggacagat ttcactctca ccatcagcag tctgcaacct      240
gaagattttg caacttacta ctgtcagcag gattatagct ctccgtggac gttcggtgga      300
ggcaccaagg tggaaatcaa a                                                321

<210> SEQ ID NO 178
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 166)

<400> SEQUENCE: 178
gacatccaga tgacccagtc tccatcctcc ctgtctgcat ctgtaggaga cagagtcacc       60
atcacttgca aggccagtca gagtgtgagt aatgatgtac attggtatca gcagaaacca      120
gggaaagccc ctaagctcct gatctattat gcatccaatc gctaccctgg ggtcccatca      180
aggttcagtg gcagtggatc tgggacagat ttcactctca ccatcagcag tctgcaacct      240
gaagattttg caacttacta ctgtcagcag gattatagct ctccgtggac gttcggtgga      300
ggcaccaagg tggaaatcaa a                                                321

<210> SEQ ID NO 179
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 167)

<400> SEQUENCE: 179
gacatccaga tgacccagtc tccatcctcc ctgtctgcat ctgtaggaga cagagtcacc       60
atcacttgca aggccagtca gagtgtgagt aatgatgtac attggtatca gcagaaacca      120
gggaaagccc ctaagctcct gatctattat gcatccaatc gctaccctgg ggtcccatca      180
aggttcagtg gcagtggatc tgggacagat ttcactctca ccatcagcag tctgcaacct      240
gaagattttg caacttacta ctgtcagcat gattatagct ctccgttcac gttcggtgga      300
ggcaccaagg tggaaatcaa a                                                321

<210> SEQ ID NO 180
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 168)

<400> SEQUENCE: 180
gacatccaga tgacccagtc tccatcctcc ctgtctgcat ctgtaggaga cagagtcacc       60
atcacttgca aggccagtca gttcgtgagt actgatgtac attggtatca gcagaaacca      120
gggaaagccc ctaagctcct gatctattat gcatccaatc gctaccctgg ggtcccatca      180
aggttcagtg gcagtggatc tgggacagat ttcactctca ccatcagcag tctgcaacct      240
gaagattttg caacttacta ctgtcagcag gattatagct ctccgtggac gttcggtgga      300
ggcaccaagg tggaaatcaa a                                                321

<210> SEQ ID NO 181
```

```
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 169)

<400> SEQUENCE: 181
gacatccaga tgacccagtc tccatcctcc ctgtctgcat ctgtaggaga cagagtcacc      60
atcacttgca aggccagtca gagtgtgagt aatgatgtag cttggtatca gcagaaacca     120
gggaaagccc ctaagctcct gatctattat gcatccatcc atacccotgg ggtcccatca    180 aggttcagtg gcagtggatc tgggacagat ttcactctca ccatcagcag tctgcaacct    240
gaagattttg caacttacta ctgtcagcag gattatagct ctccgtggac gttcggtgga    300
ggcaccaagg tggaaatcaa a                                               321

<210> SEQ ID NO 182
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 170)

<400> SEQUENCE: 182
gacatccaga tgacccagtc tccatcctcc ctgtctgcat ctgtaggaga cagagtcacc      60
atcacttgca aggccagtca gagtgtgagt aatgatgtac attggtatca gcagaaacca    120
gggaaagccc ctaagctcct gatctattat gcatccatcc atacccotgg ggtcccatca    180 aggttcagtg gcagtggatc tgggacagat ttcactctca ccatcagcag tctgcaacct    240
gaagattttg caacttacta ctgtcagcag gattatagct ctccgtggac gttcggtgga    300
ggcaccaagg tggaaatcaa a                                               321

<210> SEQ ID NO 183
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 171)

<400> SEQUENCE: 183
gacatccaga tgacccagtc tccatcctcc ctgtctgcat ctgtaggaga cagagtcacc      60
atcacttgca aggccagtca gttcgtgagt actgatgtac attggtatca gcagaaacca    120
gggaaagccc ctaagctcct gatctattat gcatccatcc atacccotgg ggtcccatca    180 aggttcagtg gcagtggatc tgggacagat ttcactctca ccatcagcag tctgcaacct    240
gaagattttg caacttacta ctgtcagcag gattatagct ctccgtggac gttcggtgga    300
ggcaccaagg tggaaatcaa a                                               321

<210> SEQ ID NO 184
<211> LENGTH: 15
<212> TYPE: PRT
<213> ORGANISM: Artificial Sequence
<220> FEATURE:
<223> OTHER INFORMATION: Synthetic Linker

<400> SEQUENCE: 184

Gly Gly Gly Gly Ser Gly Gly Gly Gly Ser Gly Gly Gly Gly Ser
 1               5                  10                  15
```

<210> SEQ ID NO 185
<211> LENGTH: 118
<212> TYPE: PRT
<213> ORGANISM: Artificial Sequence
<220> FEATURE:
<223> OTHER INFORMATION: Synthetic 10D6-HU1

<400> SEQUENCE: 185

```
Gln Val Gln Leu Gln Glu Ser Gly Pro Gly Leu Val Lys Pro Ser Glu
  1               5                  10                  15

Thr Leu Ser Leu Thr Cys Ala Val Ser Gly Tyr Ser Ile Ser Ser Asp
             20                  25                  30

Tyr Ala Trp Asn Trp Ile Arg Gln Pro Pro Gly Lys Gly Leu Glu Trp
         35                  40                  45

Ile Gly Tyr Ile Asn Tyr Ser Gly Asn Thr Asp Tyr Asn Pro Ser Leu
     50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Asn Phe Glu Gly Ala Met Asp Tyr Trp Gly Gln Gly Thr
            100                 105                 110

Leu Val Thr Val Ser Ser
        115
```

<210> SEQ ID NO 186
<211> LENGTH: 118
<212> TYPE: PRT
<213> ORGANISM: Artificial Sequence
<220> FEATURE:
<223> OTHER INFORMATION: Synthetic 10D6-HU2

<400> SEQUENCE: 186

```
Gln Val Gln Leu Gln Glu Ser Gly Pro Gly Leu Val Lys Pro Ser Glu
  1               5                  10                  15

Thr Leu Ser Leu Thr Cys Ala Val Ser Gly Tyr Ser Ile Thr Ser Asp
             20                  25                  30

Tyr Ala Trp Asn Trp Ile Arg Gln Pro Pro Gly Lys Gly Leu Glu Trp
         35                  40                  45

Met Gly Tyr Ile Asn Tyr Ser Gly Asn Thr Asp Tyr Asn Pro Ser Leu
     50                  55                  60

Lys Ser Arg Ser Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Asn Phe Glu Gly Ala Met Asp Tyr Trp Gly Gln Gly Thr
            100                 105                 110

Leu Val Thr Val Ser Ser
        115
```

<210> SEQ ID NO 187
<211> LENGTH: 118
<212> TYPE: PRT
<213> ORGANISM: Artificial Sequence
<220> FEATURE:
<223> OTHER INFORMATION: Synthetic 10D6-HU3

<400> SEQUENCE: 187

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ser Ile Thr Ser Asp
             20                  25                  30

Tyr Ala Trp Asn Trp Val Arg Gln Ala Pro Gly Lys Gly Leu Glu Trp
             35                  40                  45

Met Gly Tyr Ile Asn Tyr Ser Gly Asn Thr Asp Tyr Asn Pro Ser Leu
         50                  55                  60

Lys Ser Arg Ser Thr Ile Ser Arg Asp Thr Ser Lys Asn Thr Phe Tyr
 65                  70                  75                  80

Leu Gln Met Asn Ser Leu Arg Ala Glu Asp Thr Ala Val Tyr Tyr Cys
             85                  90                  95

Ala Arg Gly Asn Phe Glu Gly Ala Met Asp Tyr Trp Gly Gln Gly Thr
            100                 105                 110

Leu Val Thr Val Ser Ser
            115
```

<210> SEQ ID NO 188
<211> LENGTH: 240
<212> TYPE: PRT
<213> ORGANISM: Artificial Sequence
<220> FEATURE:
<223> OTHER INFORMATION: Synthetic VH-linker-VL (scFv) of 10D6

<400> SEQUENCE: 188

```
Asp Val Gln Leu Gln Glu Ser Gly Pro Asp Leu Val Lys Pro Ser Gln
  1               5                  10                  15

Ser Leu Ser Leu Thr Cys Thr Val Thr Gly Tyr Ser Ile Thr Ser Asp
             20                  25                  30

Tyr Ala Trp Asn Trp Ile Arg Gln Phe Pro Gly Asn Lys Leu Glu Trp
             35                  40                  45

Met Gly Tyr Ile Asn Tyr Ser Gly Asn Thr Asp Tyr Asn Pro Ser Leu
         50                  55                  60

Lys Ser Arg Ser Ser Ile Thr Arg Asp Thr Ser Lys Asn Gln Phe Phe
 65                  70                  75                  80

Leu Gln Leu Asn Ser Val Thr Thr Gly Asp Thr Ala Thr Tyr Tyr Cys
             85                  90                  95

Ala Arg Gly Asn Phe Glu Gly Ala Met Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Ser Ile Val Met Thr Gln Thr Pro Lys Phe Leu
            130                 135                 140

Leu Val Ser Ala Gly Asp Arg Val Thr Ile Thr Cys Lys Ala Ser Gln
145                 150                 155                 160

Ser Val Ser Asn Asp Val Ala Trp Tyr Gln Gln Lys Pro Gly Gln Ser
                165                 170                 175

Pro Lys Leu Leu Ile Tyr Tyr Ala Ser Asn Arg Tyr Pro Gly Val Pro
                180                 185                 190

Asp Arg Phe Thr Gly Ser Gly Tyr Gly Thr Asp Phe Thr Phe Thr Ile
                195                 200                 205

Ser Thr Val Gln Ala Glu Asp Leu Ala Val Tyr Phe Cys Gln Gln Asp
            210                 215                 220

Tyr Ser Ser Pro Trp Thr Phe Gly Gly Gly Thr Lys Leu Glu Ile Lys
225                 230                 235                 240
```

<210> SEQ ID NO 189
<211> LENGTH: 720
<212> TYPE: DNA
<213> ORGANISM: Artificial Sequence
<220> FEATURE:
<223> OTHER INFORMATION: Synthetic Coding sequence of VH-linker-VL
      (scFv) of 10D6

<400> SEQUENCE: 189

```
gatgtgcagc ttcaggagtc gggacctgac ctggtgaaac cttctcagtc tctgtccctc      60
acctgcactg tcactggcta ctcaatcacc agtgattatg cctggaactg gatccggcag     120
tttccaggaa acaaactgga gtggatgggc tacataaact acagtggtaa cactgactac     180
aacccatctc tcaaaagtcg aagctctatc actcgagaca catccaagaa ccagttcttc     240
ctgcagttga attctgtgac tactggggac acagccacat attactgtgc aagaggtaac     300
ttcgaaggtg ctatggacta ctggggtcaa ggaacctcag tcaccgtctc ctcaggcggc     360
ggcggcagcg gcggcggcgg cagcggcggc ggcggcagca gtattgtgat gacccagact     420
cccaaattcc tgcttgtatc agcaggagac agggttacca taacctgcaa ggccagtcag     480
agtgtgagta atgatgtagc ttggtaccaa cagaagccag gcagtctcc taaactgctg      540 atatactatg catccaatcg ctaccctgga gtccctgatc gcttcactgg cagtggatat     600
gggacggatt tcactttcac catcagcact gtgcaggctg aagacctggc agtttatttc     660
tgtcagcagg attatagctc tccgtggacg ttcggtggag gcaccaagct ggaaatcaaa     720
```

<210> SEQ ID NO 190
<211> LENGTH: 240
<212> TYPE: PRT
<213> ORGANISM: Artificial Sequence
<220> FEATURE:
<223> OTHER INFORMATION: Synthetic VH-linker-VL (scFv) of10D6 opti-1

<400> SEQUENCE: 190

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Lys Ile Ser Tyr Ser Gly Lys Thr Asp Tyr Asn Pro Ser Leu
    50                  55                  60

Lys Ser Arg Ser Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Gly Asn Phe Glu Gly Ala Met Asp Tyr Trp Gly Gln Gly Thr
           100                 105                 110

Leu Val Thr Val Ser Ser Gly Gly Gly Ser Gly Gly Gly Gly Gly Ser
       115                 120                 125

Gly Gly Gly Gly Ser Asp Ile Gln Met Thr Gln Ser Pro Ser Ser Leu
   130                 135                 140

Ser Ala Ser Val Gly Asp Arg Val Thr Ile Thr Cys Lys Ala Ser Gln
145                 150                 155                 160

Ser Val Ser Asn Asp Val Ala Trp Tyr Gln Gln Lys Pro Gly Lys Ala
               165                 170                 175

Pro Lys Leu Leu Ile Tyr Tyr Ala Ser Asn Arg Tyr Pro Gly Val Pro
```

```
              180                 185                 190
Ser Arg Phe Ser Gly Ser Gly Ser Gly Thr Asp Phe Thr Leu Thr Ile
            195                 200                 205

Ser Ser Leu Gln Pro Glu Asp Phe Ala Thr Tyr Tyr Cys Gln Gln Asp
            210                 215                 220

Tyr Ser Ser Pro Trp Thr Phe Gly Gln Gly Thr Lys Leu Glu Ile Lys
225                 230                 235                 240
```

<210> SEQ ID NO 191
<211> LENGTH: 720
<212> TYPE: DNA
<213> ORGANISM: Artificial Sequence
<220> FEATURE:
<223> OTHER INFORMATION: Synthetic Coding sequence of VH-linker-VL
      (scFv) of 10D6 opti-1

<400> SEQUENCE: 191

```
caggtgcaac tgcaggagtc aggccccggc ctggtaaaac cttctgaaac gctctcactt    60
acctgtgccg ttagtggata ctctatcact tccgactacg cttggaattg gattcggcag   120
cctccaggca aagggctgga atggatggga aagatttcct attccggtaa gactgactac   180
aatcccagtc tgaagagcag gtcaacaatc tccagagaca ccagcaagaa tcagttttcc   240
ctgaaattgt cctcggtgac agcagcggat accgcagtgt attattgcgc cgcggtaac    300 ttcgagggag ctatggatta ctgggggcag ggtactctcg tcactgtgag cagcggcggc   360
ggcggcagcg gcggcggcgg cagcggcggc ggcggcagcg acatccagat gacccagtct   420
ccatcctccc tgtctgcatc tgtaggagac agagtcacca tcacttgcaa ggccagtcag   480
agtgtgagta atgatgtagc ttggtatcag cagaaaccag ggaaagcccc taagctcctg   540
atctattatg catccaatcg ctaccctggg gtcccatcaa ggttcagtgg cagtggatct   600
gggacagatt tcactctcac catcagcagt ctgcaacctg aagattttgc aacttactac   660
tgtcagcagg attatagctc tccgtggacg ttcggtggag gcaccaaggt ggaaatcaaa   720
```

<210> SEQ ID NO 192
<211> LENGTH: 107
<212> TYPE: PRT
<213> ORGANISM: Artificial Sequence
<220> FEATURE:
<223> OTHER INFORMATION: Synthetic Light chain variable resion (Hu1-1)

<400> SEQUENCE: 192

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Ser Val Ser Asn Asp
             20                  25                  30

Val Ala Trp Tyr Gln Gln Lys Pro Gly Lys Ala Pro Lys Leu Leu Ile
         35                  40                  45

Tyr Tyr Ala Ser Asn Arg Tyr Pro Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                 85                  90                  95

Thr Phe Gly Gly Gly Thr Lys Leu Glu Ile Lys
            100                 105
```

<210> SEQ ID NO 193

<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 192)

<400> SEQUENCE: 193

```
gacatccaga tgacccagtc tccatcctcc ctgtctgcat ctgtaggaga cagagtcacc      60
atcacttgca aggccagtca gagtgtgagt aatgatgtag cttggtatca gcagaaacca     120
gggaaagccc ctaagctcct gatctattat gcatccaatc gctaccctgg ggtcccatca     180
aggttcagtg gcagtggatc tgggacagat ttcactctca ccatcagcag tctgcaacct     240
gaagattttg caacttacta ctgtcagcag gattatagct ctccgtggac gttcggtgga     300
ggcaccaagc tggaaatcaa a                                                321
```

<210> SEQ ID NO 194
<211> LENGTH: 710
<212> TYPE: PRT
<213> ORGANISM: Artificial Sequence
<220> FEATURE:
<223> OTHER INFORMATION: Synthetic Heavy chain of anti-c-Met/anti-Ang2
      bispecific antibody

<400> SEQUENCE: 194

```
Met Glu Trp Ser Trp Val Phe Leu Val Thr Leu Leu Asn Gly Ile Gln
 1               5                  10                  15
Cys Glu Val Gln Leu Val Glu Ser Gly Gly Gly Leu Val Gln Pro Gly
            20                  25                  30
Gly Ser Leu Arg Leu Ser Cys Ala Ala Ser Gly Phe Thr Phe Thr Asp
        35                  40                  45
Tyr Tyr Met Ser Trp Val Arg Gln Ala Pro Gly Lys Gly Leu Glu Trp
    50                  55                  60
Leu Gly Phe Ile Arg Asn Lys Ala Asn Gly Tyr Thr Thr Glu Tyr Ser
65                  70                  75                  80
Ala Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Ala Arg Asp Asn Trp Phe Ala Tyr Trp Gly Gln Gly Thr
        115                 120                 125
Leu Val Thr Val Ser Ser Ala Ser Thr Lys Gly Pro Ser Val Phe Pro
    130                 135                 140
Leu Ala Pro Cys Ser Arg Ser Thr Ser Glu Ser Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Asn Phe Gly Thr Gln Thr Tyr Thr Cys Asn Val Asp His Lys Pro Ser
    210                 215                 220
Asn Thr Lys Val Asp Lys Thr Val Glu Arg Lys Cys Cys Val Glu Cys
225                 230                 235                 240
Pro Pro Cys Pro Ala Pro Pro Val Ala Gly Pro Ser Val Phe Leu Phe
                245                 250                 255
```

```
Pro Pro Lys Pro Lys Asp Thr Leu Met Ile Ser Arg Thr Pro Glu Val
        260                 265                 270

Thr Cys Val Val Asp Val Ser His Glu Asp Pro Glu Val Gln Phe
        275                 280                 285

Asn Trp Tyr Val Asp Gly Val Glu Val His Asn Ala Lys Thr Lys Pro
        290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
            325                 330                 335

Ser Asn Lys Gly Leu Pro Ala Pro Ile Glu Lys Thr Ile Ser Lys Thr
        340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
            405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys Gly Gly Gly Gly
        450                 455                 460

Ser Gly Gly Gly Gly Ser Gln Val Gln Leu Gln Glu Ser Gly Pro Gly
465                 470                 475                 480

Leu Val Lys Pro Ser Glu Thr Leu Ser Leu Thr Cys Ala Val Ser Gly
            485                 490                 495

Tyr Ser Ile Thr Ser Asp Tyr Ala Trp Asn Trp Ile Arg Gln Pro Pro
        500                 505                 510

Gly Lys Gly Leu Glu Trp Met Gly Lys Ile Ser Tyr Ser Gly Lys Thr
        515                 520                 525

Asp Tyr Asn Pro Ser Leu Lys Ser Arg Ser Thr Ile Ser Arg Asp Thr
        530                 535                 540

Ser Lys Asn Gln Phe Ser Leu Lys Leu Ser Ser Val Thr Ala Ala Asp
545                 550                 555                 560

Thr Ala Val Tyr Tyr Cys Ala Arg Gly Asn Phe Glu Gly Ala Met Asp
            565                 570                 575

Tyr Trp Gly Gln Gly Thr Leu Val Thr Val Ser Ser Gly Gly Gly Gly
            580                 585                 590

Ser Gly Gly Gly Gly Ser Gly Gly Gly Gly Ser Asp Ile Gln Met Thr
        595                 600                 605

Gln Ser Pro Ser Ser Leu Ser Ala Ser Val Gly Asp Arg Val Thr Ile
        610                 615                 620

Thr Cys Lys Ala Ser Gln Ser Val Ser Asn Asp Val Ala Trp Tyr Gln
625                 630                 635                 640

Gln Lys Pro Gly Lys Ala Pro Lys Leu Leu Ile Tyr Tyr Ala Ser Asn
            645                 650                 655

Arg Tyr Pro Gly Val Pro Ser Arg Phe Ser Gly Ser Gly Ser Gly Thr
            660                 665                 670
```

Asp Phe Thr Leu Thr Ile Ser Ser Leu Gln Pro Glu Asp Phe Ala Thr
        675                 680                 685

Tyr Tyr Cys Gln Gln Asp Tyr Ser Ser Pro Trp Thr Phe Gly Gly Gly
        690                 695                 700

Thr Lys Leu Glu Ile Lys
705             710

<210> SEQ ID NO 195
<211> LENGTH: 2130
<212> TYPE: DNA
<213> ORGANISM: Artificial Sequence
<220> FEATURE:
<223> OTHER INFORMATION: Synthetic Coding sequence of heavy chain (SEQ
      ID NO: 194)

<400> SEQUENCE: 195

| | | | |
|---|---|---|---|
| atggaatgga gctgggtttt tctcgtaaca cttttaaatg gtatccagtg tgaggttcag | | | 60 |
| ctggtggagt ctggcggtgg cctggtgcag ccagggggct cactccgttt gtcctgtgca | | | 120 |
| gcttctggct tcaccttcac tgattactac atgagctggg tgcgtcaggc ccgggggtaag | | | 180 |
| ggcctggaat ggttgggttt tattagaaac aaagctaatg gttacacaac agagtacagt | | | 240 |
| gcatctgtga agggtcgttt cactataagc agagataatt ccaaaaacac actgtacctg | | | 300 |
| cagatgaaca gcctgcgtgc tgaggacact gccgtctatt attgtgctag agataactgg | | | 360 |
| tttgcttact ggggccaagg gactctggtc accgtctcct cggctagcac caagggccca | | | 420 |
| tcggtcttcc ccctggcgcc ctgctccagg agcacctccg agagcacagc ggccctgggc | | | 480 |
| tgcctggtca aggactactt ccccgaaccg gtgacggtgt cgtggaactc aggcgctctg | | | 540 |
| accagcggcg tgcacacctt cccagctgtc ctacagtcct caggactcta ctccctcagc | | | 600 |
| agcgtggtga ccgtgccctc agcaacttc ggcacccaga cctacacctg caacgtagat | | | 660 |
| cacaagccca gcaacaccaa ggtggacaag acagttgagc gcaaatgttg tgtcgagtgc | | | 720 |
| ccaccgtgcc cagcaccacc tgtggcagga ccgtcagtct tcctcttccc cccaaaaccc | | | 780 |
| aaggacaccc tcatgatctc ccggacccct gaggtcacgt gcgtggtggt ggacgtgagc | | | 840 |
| cacgaagacc ccgaggtcca gttcaactgg tacgtggacg gcgtggaggt gcataatgcc | | | 900 |
| aagacaaagc cacgggagga gcagttcaac agcacgttcc gtgtggtcag cgtcctcacc | | | 960 |
| gttgtgcacc aggactggct gaacggcaag gagtacaagt gcaaggtctc caacaaaggc | | | 1020 |
| ctcccagccc ccatcgagaa aaccatctcc aaaaccaaag gcagccccg agaaccacag | | | 1080 |
| gtgtacaccc tgcccccatc ccgggaggag atgaccaaga accaggtcag cctgacctgc | | | 1140 |
| ctggtcaaag gcttctaccc cagcgacatc gccgtggagt gggagagcaa tgggcagccg | | | 1200 |
| gagaacaact acaagaccac gcctcccatg ctggactccg acggctcctt cttcctctac | | | 1260 |
| agcaagctca ccgtggacaa gagcaggtgg cagcagggga acgtcttctc atgctccgtg | | | 1320 |
| atgcatgagg ctctgcacaa ccactacacg cagaagagcc tctccctgtc tccgggtaaa | | | 1380 |
| ggcggtggtg gttccggagg cggcggatcc caggtccagc tgcaggagag tggtcctggc | | | 1440 |
| ctggtgaaac ccagcgaaac actgtccctg acatgcgccg tatcagggta ctctatcacc | | | 1500 |
| agcgattatg cttggaattg gatccggcag ccacctggaa agggattgga atggatgggc | | | 1560 |
| aagatttcat acagtggcaa gacagactat aacccctctc tgaaaagcag aagtaccatt | | | 1620 |
| tcccgcgaca cctctaagaa tcaatttttct ctcaaactta gctcggttac tgccgcagac | | | 1680 |
| actgcagtct actattgtgc caggggcaac ttcgaggggg ctatggatta ctgggggcag | | | 1740 |
| ggtactctcg tgacggtgtc atccggtggt ggcggttcag gcggaggtgg ctctggcggt | | | 1800 |

```
ggcggatcgg acatccagat gacccagtct ccatcctccc tgtctgcatc tgtaggagac    1860
agagtcacca tcacttgcaa ggccagtcag agtgtgagta atgatgtagc ttggtatcag    1920
cagaaaccag ggaaagcccc taagctcctg atctattatg catccaatcg ctaccctggg    1980
gtcccatcaa ggttcagtgg cagtggatct gggacagatt tcactctcac catcagcagt    2040
ctgcaacctg aagattttgc aacttactac tgtcagcagg attatagctc tccgtggacg    2100
ttcggtggag gcaccaagct ggaaatcaaa                                     2130
```

<210> SEQ ID NO 196
<211> LENGTH: 114
<212> TYPE: PRT
<213> ORGANISM: Artificial Sequence
<220> FEATURE:
<223> OTHER INFORMATION: Synthetic light chain variable region of anti
      c-Met antibody

<400> SEQUENCE: 196

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```

<210> SEQ ID NO 197
<211> LENGTH: 5
<212> TYPE: PRT
<213> ORGANISM: Artificial Sequence
<220> FEATURE:
<223> OTHER INFORMATION: Synthetic Peptide Linker

<400> SEQUENCE: 197

```
Gly Gly Gly Gly Ser
 1               5
```

<210> SEQ ID NO 198
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 198

```
Asp Tyr Lys Asp Asp Asp Asp Lys
 1               5
```

ANTI-C-MET/ANTI-ANG2 BISPECIFIC ANTIBODY

CROSS-REFERENCE TO RELATED APPLICATIONS

This application claims the benefit of Korean Patent Application No. 10-2014-0110868 filed on Aug. 25, 2014 in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 197,755 Byte ASCII (text) file named "721294_ST25-Revised.TXT," created on Jan. 31, 2017.

BACKGROUND OF THE INVENTION

1. Field

Provided is an anti-c-Met/anti-Ang2 bispecific antibody including a) an anti-c-Met antibody or an antigen-binding fragment thereof and b) an anti-Ang2 antibody or an antigen-binding fragment thereof, and a pharmaceutical composition including the anti-c-Met/anti-Ang2 bispecific antibody.

2. Description of the Related Art

Angiopoietin2 (Ang2) is an antagonistic ligand of receptor Tie2 present in vascular endothelial cell (Nat Rev Mol Cell Biol. 2009 March; 10(3):165-77), and competes with Angiopoietin1 (Ang1) which is an agonist of Tie2 for binding to Tie2, thereby inhibiting the signal transduction by Tie2 (Science. 1997 Jul. 4; 277(5322):55-60). Therefore, Ang2 inhibits Ang1-Tie2 signal transduction for maintaining stability of vascular endothelial cells, leading to stimulation of angiogenesis by dynamic rearrangement of blood vessels (Science. 1997 Jul. 4; 277(5322):48-50). Preclinical studies suggest that the inhibition of the Tie2-dependent Ang2 functions can lead to the inhibition of angiogenesis, thereby preventing additional growth of cancer (J Natl Cancer Inst. 2012 Mar. 21; 104(6):461-75). However, the recent studies suggested that when a cancer cell is treated with an angiogenesis inhibitor, a mechanism for avoiding the sudden oxygen deficiency condition is activated in the cancer cell, which can stimulate cancer metastasis (Nat Rev Clin Oncol. 2011 Mar. 1; 8(4):210-21). Therefore, to avoid such serious side effects of angiogenesis inhibitors, it is necessary to inhibit functions of cancer metastasis-related proteins as well.

C-Met is a representative receptor tyrosine kinase (RTK) present on cell surface. c-Met binds to its ligand, HGF/SF (Hepatocyte Growth Factor/Scattering Factor), to promote intracellular signal transduction, thereby stimulating cell growth, and it is overexpressed in many cancer cells, thereby widely relating to cancer occurrence, cancer metastasis, cancer cell migration, cancer cell invasion, and angiogenesis. In addition, c-Met a representative early protein of cancer metastasis, because c-Met signaling through HGF/SF weakens cell-cell contact in almost all types of epithelial tumors, leading to scattering. (Nat Rev Cancer. 2012 Jan. 24; 12(2):89-103). In particular, hypoxia-response elements are present at the upstream of c-Met gene, and the expression of the gene is increased under oxygen deficiency condition (Oral Oncol. 2006 July; 42(6):593-8).

Therefore, simultaneous inhibition of Ang2 and c-Met may lead to more effective inhibition of cancer cell growth and metastasis; however, no single therapeutic for simultaneous inhibition is currently available. This invention provides such a therapeutic.

BRIEF SUMMARY OF THE INVENTION

One embodiment of the invention provides an anti-c-Met/anti-Ang2 bispecific antibody including (a) an anti-c-Met antibody or an antigen-binding fragment thereof and (b) an anti-Ang2 antibody or an antigen-binding fragment thereof.

The anti-c-Met antibody or an antigen-binding fragment thereof may be an antibody or an antigen-binding fragment thereof which specifically recognizes and/or binds to an epitope including or consisting essentially of 5 or more consecutive amino acids in SEMA domain of c-Met protein. The anti-Ang2 antibody or an antigen-binding fragment thereof may be an antibody or an antigen-binding fragment thereof which specifically binds to Ang2, but does not inhibit the binding between Ang2 and Tie2 receptor. Therefore, the anti-Ang2 antibody binds to Tie2 receptor through Ang2.

Another embodiment provides a pharmaceutical composition including the anti-c-Met/anti-Ang2 bispecific antibody. The pharmaceutical composition may be useful in preventing and/or treating a disease associated with overproduction (or overexpression) and/or abnormal activation of c-Met and/or Ang2.

Another embodiment provides a method of preventing and/or treating a disease associated with overproduction (or overexpression) and/or abnormal activation of c-Met and/or Ang2 in a subject including administering the anti-c-Met/anti-Ang2 bispecific antibody to the subject in need thereof.

Also provided is a nucleic acid encoding the anti-c-Met/anti-Ang2 bispecific antibody described herein, optionally in a vector. The nucleic acid or vector can be in a cell.

Further provided is a method of preparing an anti-c-Met/anti-Ang2 bispecific antibody as described herein by expressing a nucleic acid encoding the anti-c-Met/anti-Ang2 bispecific antibody in a cell.

DETAILED DESCRIPTION OF THE INVENTION

Figure 1:
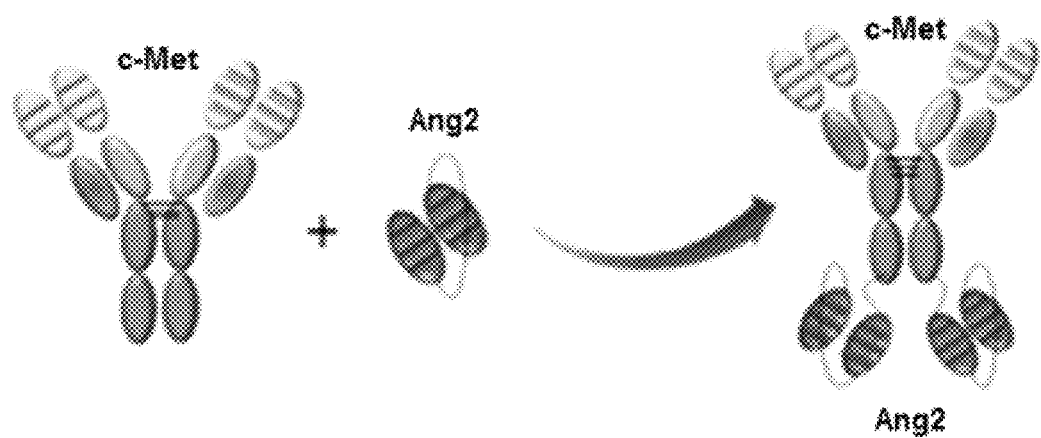
FIG. 1 is a schematic drawing of an anti-c-Met/anti-Ang2 bispecific antibody.

In one embodiment the invention provides an anti-c-Met/anti-Ang2 bispecific antibody including (a) an anti-c-Met antibody or an antigen-binding fragment thereof and (b) an anti-Ang2 antibody or an antigen-binding fragment thereof. The bispecific antibody can simultaneously recognize and bind to c-Met and Ang2, and inhibit the functions thereof, thereby exhibiting synergistic anti-cancer effects. Without wishing to be bound by any particular theory or mechanism of action, it is believed that the bispecific antibody simultaneously recognizing c-Met and Ang2 can block a signal transduction by c-Met in a cancer cell, thereby preventing the generation of a drug resistance in a subject, and thus, it can exhibit an excellent cancer cell inhibitory effect even in a cancer cell having a drug resistance.

As used herein, the term "antibody" refers to all substances generated by antigen stimulation of an immune system, which may be produced naturally (e.g., in a living body) or artificially (e.g., by any recombinant or synthetic event), and has no specific limitation in its type. The antibody may include animal antibodies, chimeric antibodies, humanized antibodies, or human antibodies. In addition, the antibody may cover any antigen-binding fragment possessing antigen binding capacity.

"c-Met" or "c-Met protein", a target of a bispecific antibody to be provided in one embodiment, refers to a receptor tyrosine kinase (RTK) which binds hepatocyte growth factor (HGF). c-Met may be derived (obtained) from any species, particularly a mammal, for instance, primates such as human c-Met (e.g., NP_000236), monkey c-Met (e.g., *Macaca mulatta*, NP_001162100), or rodents such as mouse c-Met (e.g., NP_032617.2), rat c-Met (e.g., NP_113705.1), or the like. The c-Met protein may include a polypeptide encoded by the nucleotide sequence identified as GenBank Accession Number NM_000245, a polypeptide having the amino acid sequence identified as GenBank Accession Number NP_000236 or extracellular domains thereof. The receptor tyrosine kinase c-Met participates in various biological processes, such as cancer incidence, metastasis, migration of cancer cell, invasion of cancer cell, angiogenesis, and the like.

Ang2, another target of a bispecific antibody to be provided in one embodiment, is closely related to angiogenesis. It is a soluble ligand present in blood, and it is widely involved in angiogenesis, metastasis, and cancer cell invasion. The Ang2 may be derived (obtained) from, but not limited to, mammals including primates such as humans and monkeys and rodents such as rats and mice and for example, it may be a human Ang2 (e.g., NCBI Accession #O15123), a monkey Ang2 (e.g., NCBI Accession No. Q8MIK6 etc.), a mouse Ang2 (NCBI Accession # NP_031452, Accession #O35608, etc.), a rat Ang2 (e.g., NCBI Accession No. O35462, etc.), and any combination thereof.

The anti-Ang2 antibody or an antigen-binding fragment thereof is characterized in that the antibody specifically binds to Ang2 but does not inhibit binding between Ang2 and Tie2 receptor, and forms a complex (antibody/Ang2/Tie2 complex) by binding to Tie2 receptor via Ang2. The anti-Ang2 antibody or an antigen-binding fragment thereof has ability to dimerize; through dimerization, the anti-Ang2 antibody or an antigen-binding fragment thereof can induce the activation of the Tie2 receptor and its downstream signaling by effectively clustering the Tie2 receptor in the complex. By virtue of this mechanism, the antibody and the antigen-binding fragment thereof inhibits Ang2 function by binding to Ang2 to induce the intracellular internalization and degradation thereof, and thus lowers the level of circulating Ang2. At the same time, it induces Tie2 downstream signaling by binding to the Tie2 receptor via Ang2 to activate the Tie2 receptor, like Ang1, and induces the stabilization of vascular endothelial cells. By having such dual functions, the antibody and the antigen-binding fragment thereof can be usefully employed to treat not only symptoms (disorders) due to the overexpression of Ang2 but also symptoms (disorders) due to the decrease in the stabilization of vascular endothelial cells, that is, the increase of vascular penetration.

Thus, the anti-Ang2 antibody or an antigen-binding fragment thereof is a therapeutic antibody targeting an angiogenesis-inducing factor, Ang2, which not only inhibits the functions of Ang2 by specifically binding to Ang2 but also induces the activation of Tie2 by allowing Ang2 to bind Tie2 receptor. The anti-Ang2 antibody may bind Ang2 in such a way that Ang2 may still bind with Tie2. The anti-Ang2 antibody may not directly bind to Tie2 receptor, but it can form a complex with Tie2 by binding Ang2 which, in turn, binds Tie2 receptor. The anti-Ang2 antibody or an antigen-binding fragment thereof has the effect of treating disease by binding to a Tie2 receptor together with Ang2 to activate the Tie2 receptor and thus induce the structural/functional normalization of blood vessels, along with the down-regulation of Ang2, wherein the disease may any one related to the dysfunction and/or the abnormal activation of blood vessels including cancer, sepsis, eye disorders, and the like.

One embodiment provides an anti-Ang2 antibody or an antigen-binding fragment thereof, specifically binding to (recognizing) an angiogenesis-inducing factor Ang2 (Angiopoietin-2) and binding to a Tie2 receptor together with Ang2 (e.g., via Ang2). Thus, the anti-Ang2 antibody or an antigen-binding fragment thereof may specifically recognize and/or bind to Ang2 and bind to Tie2 receptor via Ang2. Also, the anti-Ang2 antibody or an antigen-binding fragment thereof may induce the activation of the Tie2 receptor. Such activation of Tie2 receptor may be induced by an increase in the phosphorylation of Tie2 receptor and/or the phosphorylation of proteins related to the downstream signal pathway thereof, for example, at least one selected from the group consisting of Akt (e.g., encoded by NM_005163), eNOS (e.g., encoded by NM_000603), 42/44 (e.g., encoded by NM_002745), etc. Also, the anti-Ang2 antibody or an antigen-binding fragment thereof may induce the intracellular internalization of a Tie2 receptor. In other words, the anti-Ang2 antibody or an antigen-binding fragment thereof may bind to Ang2 and the Tie2 receptor via Ang2 to form a complex (antibody/Ang2/Tie2) and induce the activation of the Tie2 receptor, by not inhibiting binding between Ang2 and the Tie2 receptor while specifically binding to Ang2, unlike the pre-existing anti-Ang2 antibodies. Therefore, the anti-Ang2 antibody or an antigen-binding fragment thereof may increase the phosphorylation of a protein related to the downstream signal pathway of Tie2 receptor, such as at least one selected from the group consisting of Akt, eNOS, and 42/44, compared to the case using (treating) no antibody or any anti-Ang2 antibody inhibiting the binding between Ang2 and Tie2 receptor, such as antibody 4H10 (SEQ ID NO: 120 (heavy chain variable region) & 121 (light chain variable region)), RG antibody (Regeneron Co.), etc.

The Ang2 protein, which functions as an antigen for the anti-Ang2 antibody or antibody fragment is a soluble ligand present in blood and widely involved in angiogenesis, metastasis, cancer cell invasion, etc. Ang2 may be from mammals including primates such as humans and monkeys and rodents such as rats and mice and for example, it may be human Ang2 (e.g., NCBI Accession No. O15123, etc.), monkey Ang2 (e.g., NCBI Accession No. Q8MIK6, etc.), mouse Ang2 (e.g., NCBI Accession No. O35608, etc.), and rat Ang2 (e.g., NCBI Accession No. O35462, etc.), but is not limited thereto.

The Tie2 receptor (TEK tyrosine kinase), which is an Angiopoietin-1 receptor, is expressed in vascular endothelial cells in various mammals, such as mouse (NM_013690; NP_038718), rat, and human (NM_000459; NP_000450), and is involved in various downstream signaling.

The anti-Ang2 antibody or an antigen-binding fragment thereof may recognize (specifically bind) all or part of loop 1 of human Ang2 (hAng2; SEQ ID NO: 119; Accession #O15123). For example, the antibody or antibody fragment may specifically bind at least one amino acid residue at a site exposed to the outside of loop 1 of hAng2 (e.g., in SEQ ID NO: 119, a site from the $417^{th}$ amino acid to the $434^{th}$ amino acid) of human Ang2 or an amino acid sequence including about 2 to about 20, about 2 to about 15, about 2 to about 10, or about 2 to about 5 contiguous amino acids including at least one amino acid residue exposed to the outside of loop 1 of SEQ ID NO: 119 as an epitope.

Ang2
(SEQ ID NO: 119)

MWQIVFFTLS CDLVLAAAYN NFRKSMDSIG KKQYQVQHGS

CSYTFLLPEM DNCRSSSSPY VSNAVQRDAP LEYDDSVQRL

QVLENIMENN TQWLMKLENY IQDNMKKEMV EIQQNAVQNQ

TAVMIEIGTN LLNQTAEQTR KLTDVEAQVL NQTTRLELQL

LEHSLSTNKL EKQILDQTSE INKLQDKNSF LEKKVLAMED

KHIIQLQSIK EEKDQLQVLV SKQNSIIEEL EKKIVTATVN

NSVLQKQQHD LMETVNNLLT MMSTSNSAKD PTVAKEEQIS

FRDCAEVFKS GHTTNGIYTL TFPNSTEEIK AYCDMEAGGG

GWTIIQRRED GSVDFQRTWK EYKVGFGNPS GEYWLGNEFV

SQLTNQQRYV LKIHLKDWEG NEAYSLYEHF YLSSEELNYR

IHLKGLTGTA GKISSISQPG NDFSTKDGDN DKCICKCSQM

LTGGWWFDAC GPSNLNGMYY PQRQNTNKFN GIKWYYWKGS

GYSLKATTMM IRPADF

For example, the anti-Ang2 antibody may recognize Q418, P419, a combination of Q418 and P419 positioned at loop 1 of SEQ ID NO: 119, or an amino acid sequence site including about 2 to about 20, about 2 to about 15, about 2 to about 10, or about 2 to about 5 contiguous amino acids including the amino acid residue of Q418, P419, or combination of Q418 and P419 of SEQ ID NO: 119, as an epitope, or specifically bind to this site. In one embodiment, the anti-Ang2 antibody may recognize the amino acid residues of Q418 and P419 of SEQ ID NO: 119 as an epitope, or specifically bind to this portion.

Q418, P419, or an amino acid region including these residues, to which the anti-Ang2 antibody specifically binds, is an exposed amino acid region positioned at loop 1 of the three dimensional structure of Ang2, and it is considered to directly participate in binding between Ang2 and Tie2 receptor or to be a site regulating it.

In Q418, P419, or an amino acid region including them, to which the anti-Ang2 antibody specifically binds, the term "contiguous amino acids" may refer to amino acids which are adjacent to one another on the primary, secondary, or tertiary structure of a protein (i.e., Ang2).

Also provided is an antibody or an antigen-binding fragment thereof which competes with the above-described anti-Ang2 antibody for binding, and can inhibit Ang2 and at the same time form a complex with Ang2 and Tie2 receptor (i.e., by binding of antibody-Ang2 to the Tie2 receptor) to activate Tie2. This competitively-binding antibody may be an antibody recognizing a site adjacent to the aforementioned site on its three dimensional structure as an epitope and/or a specific binding site. The competitively-binding antibody may have a binding affinity with Ang2 of 0.1 pM to 50 nM, for example, 1 pM to 30 nM, 2 pM to 20 nM or 1 nM to 10 nM.

Therefore, the competitively-binding anti-Ang2 antibody or an antigen-binding fragment thereof may be an antibody or an antigen-binding fragment thereof specifically binding a site contiguous to the aforementioned epitope.

In a specific embodiment, the anti-Ang2 antibody or an antigen-binding fragment thereof may comprise or consist essentially of:

at least one heavy chain complementarity determining region (CDR) selected from the group consisting of a polypeptide (CDR-H1) comprising the amino acid sequence of SEQ ID NO: 109, a polypeptide (CDR-H2) comprising the amino acid sequence of SEQ ID NO: 110, and a polypeptide (CDR-H3) comprising the amino acid sequence of SEQ ID NO: 111, or a heavy chain variable region comprising the at least one heavy chain complementarity determining region;

at least one light chain complementarity determining region selected from the group consisting of a polypeptide (CDR-L1) comprising the amino acid sequence of SEQ ID NO: 112, a polypeptide (CDR-L2) comprising the amino acid sequence of SEQ ID NO: 113, and a polypeptide (CDR-L3) comprising the amino acid sequence of SEQ ID NO: 114, or a light chain variable region comprising the at least one light chain complementarity determining region;

a combination of said at least one heavy chain complementarity determining region and said at least one light chain complementarity determining region; or a combination of the heavy chain variable region and the light chain variable region.

More particularly, the anti-Ang2 antibody or an antigen-binding fragment thereof may comprise or consist essentially of:

a heavy chain variable region comprising a polypeptide (CDR-H1) comprising the amino acid sequence of SEQ ID NO: 109, a polypeptide (CDR-H2) comprising the amino acid sequence of SEQ ID NO: 110, and a polypeptide (CDR-H3) comprising the amino acid sequence of SEQ ID NO: 111; and a light chain variable region comprising a polypeptide (CDR-L1) comprising the amino acid sequence of SEQ ID NO: 112, a polypeptide (CDR-L2) comprising the amino acid sequence of SEQ ID NO: 113, and a polypeptide (CDR-L3) comprising the amino acid sequence of SEQ ID NO: 114.

Specifically, the heavy chain complementarity determining region of the anti-Ang2 antibody or an antigen-binding fragment thereof may have amino acid sequences, for example, as set forth in the following Table 1.

TABLE 1

Amino acid sequence of a heavy chain CDR

| CDRH1-KABAT | CDRH2-KABAT | CDRH3-KABAT |
|---|---|---|
| SDYAWN (SEQ ID NO: 109) | YINYSGNTDYNPSLKS (SEQ ID NO: 110) | GNFEGAMDY (SEQ ID NO: 111) |

Likewise, the light chain complementarity determining region of the anti-Ang2 antibody or an antigen-binding fragment thereof may have amino acid sequences, for example, as set forth in the following Table 2.

TABLE 2

Amino acid sequence of a light chain CDR

| CDRL1-KABAT | CDRL2-KABAT | CDRL3-KABAT |
|---|---|---|
| KASQSVSNDVA (SEQ ID NO: 112) | YASNRYP (SEQ ID NO: 113) | QQDYSSPWT (SEQ ID NO: 114) |

In one embodiment, the heavy chain variable region of the antibody or the antigen-binding fragment thereof may comprise or consist essentially of the amino acid sequence of SEQ ID NO: 115:

(SEQ ID NO: 115)
DVQLQESGPDLVKPSQSLSLTCTVTGYSITSDYAWNWIRQFPGNKLEWMG

YINYSGNTDYNPSLKSRSSITRDTSKNQFFLQLNSVTTGDTATYYCARGN

FEGAMDYWGQGTSVTVSS (In SEQ ID NO: 115 above, the underlined bold letters are CDRH1, CDRH2, and CDRH3 in sequence)

The light chain variable region of the antibody according to one embodiment may comprise or consist essentially of the amino acid sequence of SEQ ID NO: 117.

(SEQ ID NO: 117)
SIVMTQTPKFLLVSAGDRVTITCKASQSVSNDVAWYQQKPGQSPKLLIYY

ASNRYPGVPDRFTGSGYGTDFTFTISTVQAEDLAVYFCQQDYSSPWTFGG

GTKLEIK (In SEQ ID NO: 117 above, the underlined bold letters are CDRL1, CDRL2, and CDRL3 in sequence)

In this regard, the anti-Ang2 antibody or an antigen-binding fragment thereof may comprise a heavy chain variable region comprising or consisting essentially of the amino acid sequence of SEQ ID NO: 115, a light chain variable region comprising or consisting essentially of the amino acid sequence of SEQ ID NO: 117, or a combination of the heavy chain variable region and the light chain variable region.

For example, the anti-Ang2 antibody or an antigen-binding fragment thereof may comprise a heavy chain variable region comprising or consisting essentially of the amino acid sequence of SEQ ID NO: 115 and a light chain variable region comprising or consisting essentially of the amino acid sequence of SEQ ID NO: 117.

The anti-Ang2 antibody or an antigen-binding fragment thereof may be affinity-matured by substituting at least one amino acid residue of at least one CDR, for example, at least one selected from the group consisting of CDR-H2, CDR-L1, CDR-L2 and CDR-L3, with other amino acid(s) different from the original one, while maintaining the inherent activity.

For example, the affinity maturation of an anti-Ang2 antibody or an antigen-binding fragment may include at least one of the following substitutions:

(1) a substitution of the 1$^{st}$ amino acid residue Tyr (Y) of the amino acid sequence of SEQ ID NO: 110 (YINYSGNTDYNPSLKS) of CDR-H2, with Lys (K);

(2) a substitution of the 3$^{rd}$ amino acid residue Asn (N) of the amino acid sequence of SEQ ID NO: 110 (YINYSGNTDYNPSLKS) of CDR-H2, with Ser (S);

(3) a substitution of the 5$^{th}$ amino acid residue Ser (S) of the amino acid sequence of SEQ ID NO: 110 (YINYSGNTDYNPSLKS) of CDR-H2, with Ala (A);

(4) a substitution of the 7$^{th}$ amino acid residue Asn (N) of the amino acid sequence of SEQ ID NO: 110 (YINYSGNTDYNPSLKS) of CDR-H2, with Lys (K);

(5) a substitution of the 11$^{th}$ amino acid residue Ala (A) of the amino acid sequence of SEQ ID NO: 112 (KASQSVSNDVA) of CDR-L1, with His (H);

(6) a substitution of the 5$^{th}$ amino acid residue Ser (S) of the amino acid sequence of SEQ ID NO: 112 (KASQSVSNDVA) of CDR-L1, with Phe (F);

(7) a substitution of the 8$^{th}$ amino acid residue Asn (N) of the amino acid sequence of SEQ ID NO: 112 (KASQSVSNDVA) of CDR-L1, with Thr (T);

(8) a substitution of the 4$^{th}$ amino acid residue Asn (N) of the amino acid sequence of SEQ ID NO: 113 (YASNRYP) of CDR-L2, with Ile (I);

(9) a substitution of the 5$^{th}$ amino acid residue Arg (R) of the amino acid sequence of SEQ ID NO: 113 (YASNRYP) of CDR-L2, with Pro (P);

(10) a substitution of the 2$^{nd}$ amino acid residue Gln (Q) of the amino acid sequence of SEQ ID NO: 114 (QQDYSSPWT) of CDR-L3, with His (H); and

(11) a substitution of the 8$^{th}$ amino acid residue Trp (W) of the amino acid sequence of SEQ ID NO: 114 (QQDYSSPWT) of CDR-L3, with Phe (F), or any combination thereof.

In an embodiment, the affinity-matured anti-Ang2 antibody or an antigen-binding fragment thereof may comprise or consist essentially of a polypeptide comprising an amino acid sequence of represented by following general formula 1 (SEQ ID NO: 128) as a CDR-H2:

(General Formula 1)
(SEQ ID NO: 128)
X1-I-X2-Y-X3-G-X4-T-D-Y-N-P-S-L-K-S wherein, X1 is Tyr (Y) or Lys (K), X2 is Asn (N) or Ser (S), X3 is Ser (S) or Ala (A), and X4 is Asn (N) or Lys (K).

For example, the amino acid sequence of SEQ ID NO: 128 may be the amino acid sequence of SEQ ID NO: 122 or SEQ ID NO: 123.

In another embodiment, the affinity-matured anti-Ang2 antibody or an antigen-binding fragment thereof may comprise or consist essentially of a polypeptide comprising an amino acid sequence of represented by following general formula 2 (SEQ ID NO: 129) as a CDR-L1:

(General Formula 2)
(SEQ ID NO: 129)
K-A-S-Q-X5-V-S-X6-D-V-X7 wherein, X5 is Ser (S) or Phe (F), X6 is Asn (N) or Thr (T), and X7 is Ala (A) or His (H).

For example, the amino acid sequence of SEQ ID NO: 129 may be the amino acid sequence of SEQ ID NO: 124 or SEQ ID NO: 125.

In another embodiment, the affinity-matured anti-Ang2 antibody or an antigen-binding fragment thereof may comprise or consist essentially of a polypeptide comprising an amino acid sequence of represented by following general formula 3 (SEQ ID NO: 130) as a CDR-L2:

(General Formula 3)
(SEQ ID NO: 130)
Y-A-S-X8-X9-Y-P wherein, X8 is Asn (N) or Ile (I) and X9 is Arg (R) or Pro (P).

For example, the amino acid sequence of SEQ ID NO: 130 may be the amino acid sequence of SEQ ID NO: 126.

In another embodiment, the affinity-matured anti-Ang2 antibody or an antigen-binding fragment thereof may comprise or consist essentially of a polypeptide comprising an amino acid sequence of represented by following general formula 4 (SEQ ID NO: 131) as a CDR-L3:

(General Formula 4)
(SEQ ID NO: 131)
Q-X10-D-Y-S-S-P-X11-T wherein, X10 is Gln (Q) or His (H) and X11 is Trp (W) or Phe (F).

For example, the amino acid sequence of SEQ ID NO: 131 may be the amino acid sequence of SEQ ID NO: 127.

In an embodiment, the affinity-matured anti-Ang2 antibody or an antigen-binding fragment thereof may comprise or consist essentially of:

a heavy chain variable region comprising a polypeptide (CDR-H1) comprising the amino acid sequence of SEQ ID NO: 109, a polypeptide (CDR-H2) comprising the amino acid sequence of SEQ ID NO: 128, and a polypeptide (CDR-H3) comprising the amino acid sequence of SEQ ID NO: 111;

a light chain variable region comprising a polypeptide (CDR-L1) comprising the amino acid sequence of SEQ ID NO: 129, a polypeptide (CDR-L2) comprising the amino acid sequence of SEQ ID NO: 130, and a polypeptide (CDR-L3) comprising the amino acid sequence of SEQ ID NO: 131;

or a combination of the heavy chain variable region and the light chain variable region.

For example, the affinity-matured anti-Ang2 antibody or an antigen-binding fragment thereof may comprise or consist essentially of:

a heavy chain complementarity determining region comprising a polypeptide (CDR-H1) comprising the amino acid sequence of SEQ ID NO: 109, a polypeptide (CDR-H2) comprising the amino acid sequence selected from the group consisting of SEQ ID NOs: 110, 122, and 123, and a polypeptide (CDR-H3) comprising the amino acid sequence of SEQ ID NO: 111, or a heavy chain variable region comprising the heavy chain complementarity determining region;

a light chain complementarity determining region comprising a polypeptide (CDR-L1) comprising the amino acid sequence selected from the group consisting of SEQ ID NOs: 112, 124, and 125, a polypeptide (CDR-L2) comprising the amino acid sequence of SEQ ID NO: 113 or 126, and a polypeptide (CDR-L3) comprising the amino acid sequence of SEQ ID NO: 114 or 127, or a light chain variable region comprising the light chain complementarity determining region;

a combination of the heavy chain complementarity determining region and the light chain complementarity determining region; or a combination of the heavy chain variable region and the light chain variable region.

In one embodiment, the affinity-matured anti-Ang2 antibody or an antigen-binding fragment thereof of the present description does not comprise all of: a polypeptide (CDR-H1) comprising the amino acid sequence of SEQ ID NO: 109, a polypeptide (CDR-H2) comprising the amino acid sequence of SEQ ID NO: 110, a polypeptide (CDR-H3 comprising the amino acid sequence of SEQ ID NO: 111, a polypeptide (CDR-L1) comprising the amino acid sequence of SEQ ID NO: 112, a polypeptide (CDR-L2) comprising the amino acid sequence of SEQ ID NO: 113, and a polypeptide (CDR-L3) comprising the amino acid sequence of SEQ ID NO: 114, at the same time (in a single antibody or antibody fragment).

The complementarity determining regions of the anti-Ang2 antibody serving as a parent (template) antibody or an antigen-binding fragment thereof, and the affinity-matured anti-Ang2 antibody or an antigen-binding fragment thereof, are summarized in Table 3, as follows:

and CDR-L3 of SEQ ID NO: 114, or a light chain variable region comprising the light chain complementarity determining region;

(b) an anti-Ang2 antibody or an antigen-binding fragment thereof comprising a CDR-H1 of SEQ ID NO: 109, a CDR-H2 of SEQ ID NO: 122, and a CDR-H3 of SEQ ID NO: 111, or a heavy chain variable region comprising the heavy chain complementarity determining region; and a CDR-L1 of SEQ ID NO: 124, CDR-L2 of SEQ ID NO: 113, and CDR-L3 of SEQ ID NO: 114, or a light chain variable region comprising the light chain complementarity determining region;

(c) an anti-Ang2 antibody or an antigen-binding fragment thereof comprising a CDR-H1 of SEQ ID NO: 109, a CDR-H2 of SEQ ID NO: 123, and a CDR-H3 of SEQ ID NO: 111, or a heavy chain variable region comprising the heavy chain complementarity determining region; and a CDR-L1 of SEQ ID NO: 112, CDR-L2 of SEQ ID NO: 113, and CDR-L3 of SEQ ID NO: 114, or a light chain variable region comprising the light chain complementarity determining region;

(d) an anti-Ang2 antibody or an antigen-binding fragment thereof comprising a CDR-H1 of SEQ ID NO: 109, a CDR-H2 of SEQ ID NO: 123, and a CDR-H3 of SEQ ID NO: 111, or a heavy chain variable region comprising the heavy chain complementarity determining region; and a CDR-L1 of SEQ ID NO: 124, CDR-L2 of SEQ ID NO: 113, and CDR-L3 of SEQ ID NO: 114, or a light chain variable region comprising the light chain complementarity determining region;

(e) an anti-Ang2 antibody or an antigen-binding fragment thereof comprising a CDR-H1 of SEQ ID NO: 109, a

TABLE 3

| Amino acid sequence of a heavy chain CDR | | | |
|---|---|---|---|
| | CDRH1-KABAT | CDRH2-KABAT | CDRH3-KABAT |
| Parent antibody (Template) | SDYAWN (SEQ ID NO: 109) | YINYSGNTDYNPSLKS (SEQ ID NO: 110) | GNFEGAMDY (SEQ ID NO: 111) |
| Affinity-matured antibody | — | KI<u>S</u>YSG<u>K</u>TDYNPSLKS (SEQ ID NO: 122) | — |
| | | KINY<u>A</u>GNTDYNPSLKS (SEQ ID NO: 123) | — |

| Amino acid sequence of a light chain CDR | | | |
|---|---|---|---|
| | CDRL1-KABAT | CDRL2-KABAT | CDRL3-KABAT |
| Parent antibody (Template) | KASQSVSNDVA (SEQ ID NO: 112) | YASNRYP (SEQ ID NO: 113) | QQDYSSPWT (SEQ ID NO: 114) |
| Affinity-matured antibody | KASQSVSNDV<u>H</u> (SEQ ID NO: 124) KASQ<u>F</u>V<u>S</u>TDV<u>H</u> (SEQ ID NO: 125) | YAS<u>IP</u>YP (SEQ ID NO: 126) | Q<u>H</u>DYSSP<u>F</u>T (SEQ ID NO: 127) |

For example, the affinity-matured anti-Ang2 antibody or an antigen-binding fragment thereof may be selected from the group consisting of:

(a) an anti-Ang2 antibody or an antigen-binding fragment thereof comprising a CDR-H1 of SEQ ID NO: 109, a CDR-H2 of SEQ ID NO: 122, and a CDR-H3 of SEQ ID NO: 111, or a heavy chain variable region comprising the heavy chain complementarity determining regions; and a CDR-L1 of SEQ ID NO: 112, CDR-L2 of SEQ ID NO: 113, CDR-H2 of SEQ ID NO: 110, and a CDR-H3 of SEQ ID NO: 111, or a heavy chain variable region comprising the heavy chain complementarity determining region; and a CDR-L1 of SEQ ID NO: 124, CDR-L2 of SEQ ID NO: 113, and CDR-L3 of SEQ ID NO: 127, or a light chain variable region comprising the light chain complementarity determining region;

(f) an anti-Ang2 antibody or an antigen-binding fragment thereof comprising a CDR-H1 of SEQ ID NO: 109, a CDR-H2 of SEQ ID NO: 122, and a CDR-H3 of SEQ ID NO: 111, or a heavy chain variable region comprising the heavy chain complementarity determining region; and a CDR-L1 of SEQ ID NO: 125, CDR-L2 of SEQ ID NO: 113, and CDR-L3 of SEQ ID NO: 114, or a light chain variable region comprising the light chain complementarity determining region;

(g) an anti-Ang2 antibody or an antigen-binding fragment thereof comprising a CDR-H1 of SEQ ID NO: 109, a CDR-H2 of SEQ ID NO: 122, and a CDR-H3 of SEQ ID NO: 111, or a heavy chain variable region comprising the heavy chain complementarity determining region; and a CDR-L1 of SEQ ID NO: 112, CDR-L2 of SEQ ID NO: 126, and CDR-L3 of SEQ ID NO: 114, or a light chain variable region comprising the light chain complementarity determining region;

(h) an anti-Ang2 antibody or an antigen-binding fragment thereof comprising a CDR-H1 of SEQ ID NO: 109, a CDR-H2 of SEQ ID NO: 126, and a CDR-H3 of SEQ ID NO: 111, or a heavy chain variable region comprising the heavy chain complementarity determining region; and a CDR-L1 of SEQ ID NO: 124, CDR-L2 of SEQ ID NO: 126, and CDR-L3 of SEQ ID NO: 114, or a light chain variable region comprising the light chain complementarity determining region; and (i) an anti-Ang2 antibody or an antigen-binding fragment thereof comprising a CDR-H1 of SEQ ID NO: 109, a CDR-H2 of SEQ ID NO: 122, and a CDR-H3 of SEQ ID NO: 111, or a heavy chain variable region comprising the heavy chain complementarity determining region; and a CDR-L1 of SEQ ID NO: 125, CDR-L2 of SEQ ID NO: 126, and CDR-L3 of SEQ ID NO: 114, or a light chain variable region comprising the light chain complementarity determining region.

The affinity-matured anti-Ang2 antibody or an antigen-binding fragment may have an binding affinity (KD) to Ang2 of about 10 nM or less, about 5 nM or less, about 2 nM or less, or about 1 nM or less, for example, about 0.01 to about 10 nM, about 0.01 to about 5 nM, about 0.01 to about 2 nM, or about 0.01 to about 1 nM. The affinity-matured anti-Ang2 antibody or an antigen-binding fragment shows a considerable improvement in the binding affinity (KD) to Ang2, considering that the binding affinity (KD) to Ang2 of its parent antibody anti-Ang2 antibody is about 8 nM.

In another embodiment, a humanized anti-Ang2 antibody or an antigen-binding fragment thereof is provided. The humanized anti-Ang2 antibody or an antigen-binding fragment thereof may be obtained by substituting at least one amino acid residue of framework region (i.e., the region other than the heavy chain complementarity determining region) of a heavy chain variable region (e.g., SEQ ID NO: 115). The amino acid sequences of the framework region of a heavy chain variable region, which can be used in producing a humanized anti-Ang2 antibody or an antigen-binding fragment thereof, are summarized in Table 4:

TABLE 4

| (Humanization of a heavy chain) | | | | |
|---|---|---|---|---|
| | FR1 (framework region of N-terminus of CDR-H1) | FR2 (framework region between CDR-H1 and CDR-H2) | FR3 (framework region between CDR-H2 and CDR-H3) | FR4 (framework region of C-terminus of CDR-H3) |
| Parent antibody (SEQ ID NO: 115) | DVQLQESGPDLVK PSQSLSLTCTVTG YSIT (SEQ ID NO: 132) | WIRQFPGNKLEWMG (SEQ ID NO: 137) | RSSITRDTSKNQFF LQLNSVTTGDTAT YYCAR (SEQ ID NO: 142) | WGQGTSVTVSS (SEQ ID NO: 147) |
| Humanized antibody (VH-hu1) | QVQLQESGPGLVK PSETLSLTCAVSG YSIS (SEQ ID NO: 133) | WIRQPPGKGLEWIG (SEQ ID NO: 138) | RVTISVDTSKNQF SLKLSSVTAADTA VYYCAR (SEQ ID NO: 143) | WGQGTLVTVSS (SEQ ID NO: 148) |
| Humanized antibody (VH-hu2) | QVQLQESGPGLVK PSETLSLTCAVSG YSIT (SEQ ID NO: 134) | WIRQPPGKGLEWMG (SEQ ID NO: 139) | RSTISRDTSKNQFS LKLSSVTAADTAV YYCAR (SEQ ID NO: 144) | WGQGTLVTVSS (SEQ ID NO: 149) |
| Humanized antibody (VH-hu5) | QVQLQESGPGLVK PSETLSLTCAVSG YSIT (SEQ ID NO: 135) | WIRQPPGKGLEWIG (SEQ ID NO: 140) | RVTISVDTSKNQF SLKLSSVTAADTA VYYCAR (SEQ ID NO: 145) | WGQGTLVTVSS (SEQ ID NO: 150) |
| Humanized antibody (VH-hu3) | EVQLVESGGGLV QPGGSLRLSCAAS GYSIT (SEQ ID NO: 136) | WVRQAPGKGLEWMG (SEQ ID NO: 141) | RSTISRDTSKNTFY LQMNSLRAEDTA VYYCAR (SEQ ID NO: 146) | WGQGTLVTVSS (SEQ ID NO: 151) |

In addition, the humanized anti-Ang2 antibody or an antigen-binding fragment thereof may be obtained by substituting at least one amino acid residue of framework region (i.e., the region other than the heavy chain complementarity determining region) of a light chain variable region (e.g., SEQ ID NO: 117). The amino acid sequences of the framework region of a light chain variable region, which can be used in producing a humanized anti-Ang2 antibody or an antigen-binding fragment thereof, are summarized in Table 5:

TABLE 5

(Humanization of a light chain)

| | FR1 (framework region adjacent to N-terminus of CDR-L1) | FR2 (framework region between CDR-L1 and CDR-L2) | FR3 (framework region between CDR-L2 and CDR-L3) | FR4 (framework region adjacent to C-terminus of CDR-L3) |
|---|---|---|---|---|
| Original light chain (SEQ ID NO: 117) | SIVMTQTPKFLLVS AGDRVTITC (SEQ ID NO: 152) | WYQQKPGQSPKLLIY (SEQ ID NO: 154) | GVPDRFTGSGYGT DFTFTISTVQAEDL AVYFC (SEQ ID NO: 156) | FGGGTKLEIK (SEQ ID NO: 158) |
| Humanized light chain (VL-hu1) | DIQMTQSPSSLSAS VGDRVTITC (SEQ ID NO: 153) | WYQQKPGKAPKLLIY (SEQ ID NO: 155) | GVPSRFSGSGSGTD FTLTISSLQPEDFAT YYC (SEQ ID NO: 157) | FGQGTKVEIK (SEQ ID NO: 159) |

In an embodiment, a heavy chain variable region of the humanized anti-Ang2 antibody or an antigen-binding fragment thereof may comprise or consist essentially of:

a polypeptide comprising an amino acid sequence selected from the group consisting of SEQ ID NOs: 132 to 136, for example, an amino acid sequence selected from the group consisting of SEQ ID NOs: 133 to 136, as a framework region adjacent to N-terminus of CDR-H1, a polypeptide comprising an amino acid sequence selected from the group consisting of SEQ ID NOs: 137 to 141, for example, an amino acid sequence selected from the group consisting of SEQ ID NOs: 138 to 141, as a framework region between CDR-H1 and CDR-H2, a polypeptide comprising an amino acid sequence selected from the group consisting of SEQ ID NOs: 142 to 146, for example, an amino acid sequence selected from the group consisting of SEQ ID NOs: 143 to 146, as a framework region between CDR-H2 and CDR-H3, and a polypeptide comprising an amino acid sequence selected from the group consisting of SEQ ID NOs: 147 to 151, for example, an amino acid sequence selected from the group consisting of SEQ ID NOs: 148 to 151, as a framework region adjacent to C-terminus of CDR-H3.

A light chain variable region of the humanized anti-Ang2 antibody or an antigen-binding fragment thereof may comprise or consist essentially of:

a polypeptide comprising an amino acid sequence selected from the group consisting of SEQ ID NO: 152 or 153, for example, an amino acid sequence selected from the group consisting of SEQ ID NO: 153, as a framework region adjacent to N-terminus of CDR-L1, a polypeptide comprising an amino acid sequence selected from the group consisting of SEQ ID NO: 154 or 155, for example, an amino acid sequence selected from the group consisting of SEQ ID NO: 155, as a framework region between CDR-L1 and CDR-L2, a polypeptide comprising an amino acid sequence selected from the group consisting of SEQ ID NO: 156 or 157, for example, an amino acid sequence selected from the group consisting of SEQ ID NO: 157, as a framework region between CDR-L2 and CDR-L3, and a polypeptide comprising an amino acid sequence selected from the group consisting of SEQ ID NO: 158 or 159, for example, an amino acid sequence selected from the group consisting of SEQ ID NO: 159, as a framework region adjacent to C-terminus of CDR-L3.

In one embodiment, the anti-Ang2 antibody or antibody fragment does not comprise a heavy chain variable region comprising the amino acid sequence of SEQ ID NO: 132 as a framework region adjacent to N-terminus of CDR-H1, the amino acid sequence of SEQ ID NO: 137 as a framework region between CDR-H1 and CDR-H2, the amino acid sequence of SEQ ID NO: 142 as a framework region between CDR-H2 and CDR-H3, and the amino acid sequence of SEQ ID NO: 147 as a framework region adjacent to C-terminus of CDR-H3; and/or a light chain variable region comprising the amino acid sequence of SEQ ID NO: 152 as a framework region adjacent to N-terminus of CDR-L1, the amino acid sequence of SEQ ID NO: 154 as a framework region between CDR-L1 and CDR-L2, the amino acid sequence of SEQ ID NO: 156 as a framework region between CDR-L2 and CDR-L3, and the amino acid sequence of SEQ ID NO: 158 as a framework region adjacent to C-terminus of CDR-L3.

In an embodiment, the humanized anti-Ang2 antibody or an antigen-binding fragment thereof may comprise a heavy chain variable region comprising or consisting essentially of an amino acid sequence selected from the group consisting of SEQ ID NO: 160, SEQ ID NO: 161, SEQ ID NO: 162, SEQ ID NO: 163, or SEQ ID NO:164, a light chain variable region comprising or consisting essentially of an amino acid sequence selected from the group consisting of SEQ ID NO: 165, SEQ ID NO: 166, SEQ ID NO: 167, SEQ ID NO: 168, SEQ ID NO: 169, SEQ ID NO: 170, or SEQ ID NO: 171, or any combination thereof.

The anti-c-Met antibody may recognize a specific region of c-Met, e.g., a specific region in the SEMA domain, as an epitope. It may be any antibody or antigen-binding fragment that acts on c-Met to induce intracellular internalization and degradation of c-Met.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and includes a SEMA domain responsible for binding HGF, a plexin-semaphorins-integrin identity/homology domain (PSI domain) and an immunoglobulin-like fold shared by plexins and transcriptional factors domain (IPT domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79), is a loop region between the second and the third beta propellers within the epitopes of the SEMA domain. This region acts as an epitope for the anti-c-Met antibody provided in the present description.

The term "epitope," as used herein, refers to an antigenic determinant, a part of an antigen recognized by an antibody. In one embodiment, the epitope may be a region including 5 or more contiguous (consecutive on primary, secondary (two-dimensional), or tertiary (three-dimensional) structure) amino acid residues within the SEMA domain (SEQ ID NO: 79) of c-Met protein, for instance, 5 to 19 contiguous amino acid residues within the amino acid sequence of SEQ ID NO: 71. For example, the epitope may be a polypeptide having 5 to 19 contiguous amino acids selected from among partial combinations of the amino acid sequence of SEQ ID NO: 71, wherein the polypeptide includes the amino acid sequence of SEQ ID NO: 73 (EEPSQ) serving as an essential element for the epitope. For example, the epitope may be a polypeptide including, consisting essentially of, or consisting of the amino acid sequence of SEQ ID NO: 71, SEQ ID NO: 72, or SEQ ID NO: 73.

The epitope having the amino acid sequence of SEQ ID NO: 72 corresponds to the outermost part of the loop between the second and third beta propellers within the SEMA domain of a c-Met protein. The epitope having the amino acid sequence of SEQ ID NO: 73 is a site to which the antibody or antigen-binding fragment according to one embodiment most specifically binds.

Thus, the anti-c-Met antibody may specifically bind to an epitope which includes 5 to 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody or an antigen-binding fragment thereof may comprise or consist essentially of:

at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5, SEQ ID NO: 2, or an amino acid sequence including 8-19 consecutive amino acids within SEQ ID NO: 2 including amino acid residues from the $3^{rd}$ to $10^{th}$ positions of SEQ ID NO: 2; and (c) a CDR-H3 including the amino acid sequence of SEQ ID NO: 6, SEQ ID NO: 85, or an amino acid sequence including 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9, SEQ ID NO: 15, SEQ ID NO: 86, or an amino acid sequence including 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I
(SEQ ID NO: 4)
$Xaa_1$-$Xaa_2$-Tyr-Tyr-Met-Ser, wherein $Xaa_1$ is absent or Pro or Ser, and $Xaa_2$ is Glu or Asp, Formula II
(SEQ ID NO: 5)
Arg-Asn-$Xaa_3$-$Xaa_4$-Asn-Gly-$Xaa_5$-Thr, wherein $Xaa_3$ is Asn or Lys, $Xaa_4$ is Ala or Val, and $Xaa_5$ is Asn or Thr, Formula III
(SEQ ID NO: 6)
Asp-Asn-Trp-Leu-$Xaa_6$-Tyr, wherein $Xaa_6$ is Ser or Thr, Formula IV
(SEQ ID NO: 7)
Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala wherein $Xaa_7$ is His, Arg, Gln, or Lys, $Xaa_8$ is Ser or Trp, $Xaa_9$ is His or Gln, and $Xaa_{10}$ is Lys or Asn, Formula V
(SEQ ID NO: 8)
Trp-$Xaa_{11}$-Ser-$Xaa_{12}$-Arg-Val-$Xaa_{13}$ wherein $Xaa_{11}$ is Ala or Gly, $Xaa_{12}$ is Thr or Lys, and $Xaa_{13}$ is Ser or Pro, and Formula VI
(SEQ ID NO: 9)
$Xaa_{14}$-Gln-Ser-Tyr-Ser-$Xaa_{15}$-Pro-$Xaa_{16}$-Thr wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may comprise or consist essentially of an amino acid sequence selected from the group consisting of SEQ ID NO: 1, SEQ ID NO: 22, SEQ ID NO: 23, and SEQ ID NO: 24. The CDR-H2 may comprise or consist essentially of an amino acid sequence selected from the group consisting of SEQ ID NO: 2, SEQ ID NO: 25, and SEQ ID NO: 26. The CDR-H3 may comprise or consist essentially of an amino acid sequence selected from the group consisting of SEQ ID NO: 3, SEQ ID NO: 27, SEQ ID NO: 28, and SEQ ID NO: 85.

The CDR-L1 may comprise or consist essentially of an amino acid sequence selected from the group consisting of SEQ ID NO: 10, SEQ ID NO: 29, SEQ ID NO: 30, SEQ ID NO: 31, SEQ ID NO: 32, SEQ ID NO: 33 and SEQ ID NO: 106. The CDR-L2 may comprise or consist essentially of an amino acid sequence selected from the group consisting of SEQ ID NO: 11, SEQ ID NO: 34, SEQ ID NO: 35, and SEQ ID NO: 36. The CDR-L3 may comprise or consist essentially of an amino acid sequence selected from the group consisting of SEQ ID NO: 12, SEQ ID NO: 13, SEQ ID NO:

14, SEQ ID NO: 15, SEQ ID NO: 16, SEQ ID NO: 37, SEQ ID NO: 86, and SEQ ID NO: 89.

In another embodiment, the antibody or antigen-binding fragment may comprise or consist essentially of a heavy chain variable region comprising a polypeptide (CDR-H1) comprising or consisting essentially of an amino acid sequence selected from the group consisting of SEQ ID NO: 1, SEQ ID NO: 22, SEQ ID NO: 23, and SEQ ID NO: 24, a polypeptide (CDR-H2) comprising or consisting essentially of an amino acid sequence selected from the group consisting of SEQ ID NO: 2, SEQ ID NO: 25, and SEQ ID NO: 26, and a polypeptide (CDR-H3) comprising or consisting essentially of an amino acid sequence selected from the group consisting of SEQ ID NO: SEQ ID NO: 3, SEQ ID NO: 27, SEQ ID NO: 28, and SEQ ID NO: 85; and a light chain variable region comprising a polypeptide (CDR-L1) comprising or consisting essentially of an amino acid sequence selected from the group consisting of SEQ ID NO: 10, SEQ ID NO: 29, SEQ ID NO: 30, SEQ ID NO: 31, SEQ ID NO: 32, SEQ ID NO: 33, and SEQ ID NO: 106, a polypeptide (CDR-L2) comprising or consisting essentially of an amino acid sequence selected from the group consisting of SEQ ID NO: 11, SEQ ID NO: 34, SEQ ID NO: 35, and SEQ ID NO: 36, and a polypeptide (CDR-L3) comprising or consisting essentially of an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In one embodiment, the anti-c-Met antibody or an antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region having the amino acid sequence of SEQ ID NO: 100 (U7-HC6), SEQ ID NO: 101 (U6-HC7), SEQ ID NO: 102 (U3-HC9), SEQ ID NO: 103 (U6-HC8), or SEQ ID NO: 104 (U8-HC5), or a hinge region having the amino acid sequence of SEQ ID NO: 105 (non-modified human hinge). In particular, the hinge region includes the amino acid sequence of SEQ ID NO: 100 or SEQ ID NO: 101.

In one embodiment, the anti-c-Met antibody or antigen-binding fragment may comprise a heavy chain variable region comprising or consisting essentially of the amino acid sequence of SEQ ID NO: 17, SEQ ID NO: 74, SEQ ID NO: 87, SEQ ID NO: 90, SEQ ID NO: 91, SEQ ID NO: 92, SEQ ID NO: 93, or SEQ ID NO: 94; a light chain variable region comprising or consisting essentially of the amino acid sequence of SEQ ID NO: 196, SEQ ID NO: 18, SEQ ID NO: 19, SEQ ID NO: 20, SEQ ID NO: 21, SEQ ID NO: 75, SEQ ID NO: 88, SEQ ID NO: 95, SEQ ID NO: 96, SEQ ID NO: 97, SEQ ID NO: 98, SEQ ID NO: 99, or SEQ ID NO: 107; or a combination of the heavy chain variable region and the light chain variable region.

In one embodiment, the anti-c-Met antibody may be a monoclonal antibody. The monoclonal antibody may be produced by the hybridoma cell line deposited with the Korean Cell Line Research Foundation, an international depository authority located at Yungun-Dong, Jongno-Gu, Seoul, Korea, on Oct. 6, 2009, under Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include any of the antibodies described in Korean Patent Publication No. 2011-0047698.

By way of further example, the anti-c-Met antibody or the antibody fragment may comprise or consist essentially of:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the 18$^{th}$ to 462$^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the 18$^{th}$ to 461$^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

The following descriptions may be applied to both the anti-c-Met antibodies or fragments thereof and the anti-Ang2 antibodies or fragments thereof described herein.

In the anti-c-Met antibody or an antigen-binding fragment thereof and the anti-Ang2 antibody or an antigen-binding fragment thereof, the portion of the light chain and the heavy chain portion, other than the CDRs, the light chain variable region, and the heavy chain variable region as defined above, for example, the light chain constant region and the heavy chain constant region, may be those from any subtype of immunoglobulin (e.g., IgA, IgD, IgE, IgG (IgG1, IgG2, IgG3, IgG4), IgM, etc.).

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies and the anti-Ang2 antibodies may be animal antibodies (e.g., mouse-derived antibodies), chimeric antibodies (e.g., mouse-human chimeric antibodies), humanized antibodies, or human antibodies. The antibodies or antigen-binding fragments thereof may be isolated from a living body or non-naturally occurring. The antibodies or antigen-binding fragments thereof may be synthetic or recombinant. The antibody may be a monoclonal antibody.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to a part of a variable region of an antibody, which allows a binding specificity to a specific antigen and an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions (e.g., at least one CDR) having the ability to specifically bind to the antigen. In a particular embodiment, the antigen-binding fragment may be scFv, (scFv)$_2$, scFvFc, Fab, Fab', or F(ab')$_2$, but is not limited thereto.

Among the antigen-binding fragments, Fab that includes light chain and heavy chain variable regions, a light chain constant region, and a first heavy chain constant region $C_{H1}$, has one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment.

Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be the same as described in the above, for example, those including the amino acid length of about 1 to about 100, about 2 to about 50, particularly about 5 to about 25, and any kinds of amino acids may be included without any restrictions.

The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

The antibody may be a monoclonal antibody. The monoclonal antibody may be prepared by methods well known in the art. For example, it may be prepared using a phage display technique.

Meanwhile, individual monoclonal antibodies may be screened using a typical ELISA (Enzyme-Linked ImmunoSorbent Assay) format, based on the binding potential with Ang2 or c-Met. Inhibitory activities can be verified through functional analysis such as competitive ELISA for verifying the molecular interaction of binding assemblies or functional analysis such as a cell-based assay. Then, with regard to monoclonal antibody members selected on the basis of their strong inhibitory activities, their affinities (Kd values) to Ang2 or c-Met may be each verified.

In an embodiment, the anti-c-Met/anti-Ang2 bispecific antibody may include an anti-c-Met antibody or an antigen-binding fragment thereof, and an anti-Ang2 antibody or an antigen-binding fragment thereof, wherein the anti-Ang2 antibody or an antigen-binding fragment thereof is linked to C-terminus or N-terminus, e.g., C-terminus, of the anti-c-Met antibody or an antigen-binding fragment thereof.

In the anti-c-Met/anti-Ang2 bispecific antibody, in order to fully perform the anti-c-Met antibody's activity to mediate intracellular migration and degradation of c-Met proteins, it may be advantageous that the anti-c-Met antibody has its own intact antibody structure. In addition, in case of the anti-Ang2 antibody, its specific recognition and binding to Ang2 is important, and thus it will be fine that just an antigen-binding fragment recognizing Ang2 is included in the bispecific antibody. Therefore, the anti-c-Met/anti-Ang2 bispecific antibody may comprise a complete anti-c-Met antibody (e.g., IgG type antibody) and an antigen binding fragment (e.g., scFv or scFv-Fc) of the anti-Ang2 antibody linked to the C terminus of the anti-c-Met antibody (e.g., the C terminus a heavy chain), but not be limited thereto. In this case, the anti-c-Met/anti-Ang2 bispecific antibody may comprise a first polypeptide (corresponding to a heavy chain of the bispecific antibody) comprising a heavy chain of an anti-c-Met antibody and an antigen binding fragment (e.g., scFv or scFv-Fc) of the anti-Ang2 antibody linked to the C terminus of the heavy chain of the anti-c-Met antibody (optionally, via a peptide linker described below), and a second polypeptide (corresponding to a light chain of the bispecific antibody) comprising a light chain of the anti-c-Met antibody.

In the anti-c-Met/anti-Ang2 bispecific antibody, the anti-c-Met antibody or the antigen binding fragment thereof, and the anti-Ang2 antibody or the antigen binding fragment thereof, may be linked via a peptide linker. Furthermore, a heavy chain portion and a light chain portion within the antigen binding fragment, for example, a heavy chain variable region and a light chain variable region within the scFv fragment, may be linked via a peptide linker. The peptide linker which links the anti-c-Met antibody or the antigen binding fragment thereof, and the anti-Ang2 antibody or the antigen binding fragment thereof, and the peptide linker which links the heavy chain portion and the light chain portion within the antigen binding fragment may be identical or different. The peptide linker may be about 1 to about 100, particularly about 2 to about 50, amino acids in length and include any kinds of amino acids. The peptide linker may include for example, Gly, Asn and/or Ser residues, and also include neutral amino acids such as Thr and/or Ala. Amino acid sequences suitable for the peptide linker are known in the relevant art. The length of the peptide linker may be determined within such a limit that the functions of the fusion protein (bispecific antibody) will not be affected. For instance, the peptide linker may be formed by including a total of about 1 to about 100, about 2 to about 50, or about 5 to about 25 of one or more amino acids selected from the group consisting of Gly, Asn, Ser, Thr, and Ala. In one embodiment, the peptide linker may be represented as ((GGGGS) (SEQ ID NO: 197))n, wherein n is a repeat number of (GGGGS) (SEQ ID NO: 197), which is an integer of about 1 to about 10, particularly an integer of about 2 to about 5.

In a particular embodiment, the anti-c-Met/anti-Ang2 bispecific antibody may include an anti-c-Met antibody, and an scFv, scFv-Fc, (scFv)$_2$, Fab, Fab' or F(ab')$_2$, for example, scFv, of an anti-Ang2 antibody linked to the C terminus of the anti-c-Met antibody. For instance, scFv, scFv-Fc, (scFv)$_2$, Fab, Fab' or F(ab')$_2$ of the anti-Ang2 antibody may include a heavy chain variable region including the amino acid sequence selected from SEQ ID NO: 160, SEQ ID NO: 161, SEQ ID NO: 162, SEQ ID NO: 163, and SEQ ID NO: 164, and a light chain variable region including the amino acid sequence selected from SEQ ID NO: 165, SEQ ID NO: 166, SEQ ID NO: 167, SEQ ID NO: 168, SEQ ID NO: 169, SEQ ID NO: 170, and SEQ ID NO: 171.

Hence, in a particular embodiment, the anti-c-Met/anti-Ang2 bispecific antibody may include an anti-c-Met antibody, and an scFv, scFv-Fc, (scFv)$_2$, Fab, Fab' or F(ab')$_2$ of an anti-Ang2 antibody including a heavy chain variable region including the amino acid sequence selected from SEQ ID NO: 160 to SEQ ID NO: 164, and a light chain variable region the amino acid sequence selected from SEQ ID NO: 165 to SEQ ID NO: 171, which is linked to the C terminal of the anti-c-Met antibody.

In an embodiment, the heavy chain of the anti-c-Met/anti-Ang2 bispecific antibody may comprise a heavy chain of an anti-c-Met antibody at N-terminal portion, and an scFv, (scFv)$_2$, scFv-Fc, Fab, Fab' or F(ab')$_2$ of an anti-Ang2 antibody at C-terminal portion, which are linked to each other directly (i.e., through no linker) or indirectly (i.e., through a linker), and for example, comprise the amino acid sequence of SEQ ID NO: 194.

The light chain of the anti-c-Met/anti-Ang2 bispecific antibody may be the same with that of the above described anti-c-Met antibody, and for example, light chain may include an amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of the amino acid sequence of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of the amino acid sequence of SEQ ID NO: 70, and the amino acid sequence of SEQ ID NO: 108.

Due to internalization and degradation activities of the anti-c-Met antibody, the anti-c-Met/anti-Ang2 bispecific antibody is capable of not only inhibiting the activities of c-Met and Ang2, but also decreasing the total amount of c-Met and Ang2 by degrading them, thereby leading to more fundamental blocking of activity of the c-Met and Ang2. Therefore, the anti-c-Met/anti-Ang2 bispecific antibody can exhibit therapeutic effects even when it is applied to a subject who has a resistance against a preexisting Ang2-targeting drug, such as an anti-Ang2, or an anti-c-Met antibody.

As described above, the anti-Ang2 antibody or an antigen-binding fragment thereof specifically binds to Ang2, and does not inhibit but induces the binding of Ang2 and Tie2 receptor. In addition, the anti-Ang2 antibody or an antigen-binding fragment thereof binds to Ang2, to form an anti-Ang2 antibody/Ang2 conjugate. The conjugate acts as Ang1, that is, binds to Tie2 receptor (wherein Ang2 part of the conjugate participates in the binding), and leads to Tie2 receptor activation. In particular, the anti-Ang2 antibody or an antigen-binding fragment thereof inhibits the functions of Ang2, thereby inhibiting an abnormal angiogenesis, and thus, it can be applicable to prevent, alleviate, improve, and/or treat various diseases (e.g., cancer) related to abnormal angiogenesis. In addition, since the anti-Ang2 antibody or an antigen-binding fragment thereof does not inhibit the binding between Ang2 and Tie2, it can activate Tie2 receptor, thereby activating a Tie2 signaling, and it can accelerate the formation of vascular endothelium or lymphatic endothelium and increase mobility, thereby suppressing vascular permeability increase. Therefore, it can be applicable to prevent, alleviate, improve, and/or treat various diseases related to vascular permeability (for example, sepsis, eye disorders, etc.). Moreover, since the anti-Ang2 antibody or an antigen-binding fragment thereof accelerates the formation of vascular endothelium or lymphatic endothelium to increase the formation of healthy blood vessels and normalize the blood vessels, it can be also applicable to prevent, alleviate, improve, and/or treat various diseases or symptoms requiring the formation of healthy blood vessels, such as wound healing or ischemic disorders. Also, the anti-Ang2 antibody or an antigen-binding fragment thereof reduces cancer growth and metastasis possibly by changing the abnormally formed cancer blood vessels into structurally and functionally normal forms. In addition, the anti-Ang2 antibody or an antigen-binding fragment thereof has an effect of suppressing inflammatory response, whereby it is applicable to prevent, alleviate, improve, and/or treat various inflammatory disorders. In addition, the anti-Ang2 antibody or an antigen-binding fragment thereof has an effect of vascular normalization, thereby increasing transporting efficiency of an anticancer agent into cancer tissues through the normalized blood vessel and increasing sensitivity to the anticancer agent. Therefore, the anti-Ang2 antibody or an antigen-binding fragment thereof can be applicable as an adjuvant to be co-administered with an anticancer agent for enhancing the efficacy of the anticancer agent. The adjuvant may refer to a supplementary pharmaceutical composition used for enhancing the efficacy of an anticancer agent.

Therefore, provided is a pharmaceutical composition including an anti-c-Met/anti-Ang2 bispecific antibody.

Another embodiment provides a pharmaceutical composition for preventing and/or treating a disease associated with Ang2/Tie2 signal transduction system and/or HGF/c-Met signal transduction system, wherein the composition comprises an anti-c-Met/anti-Ang2 bispecific antibody as an active ingredient.

Another embodiment provides a method of preventing and/or treating a disease associated with Ang2/Tie2 signal transduction system and/or HGF/c-Met signal transduction system in a subject, comprising administering an anti-c-Met/anti-Ang2 bispecific antibody to the subject (who is in need of preventing and/or treating a disease associated with Ang2/Tie2 signal transduction system and/or HGF/c-Met signal transduction system). The anti-c-Met/anti-Ang2 bispecific antibody may be administered in a pharmaceutically effective amount for preventing and/or treating a disease associated with Ang2/Tie2 signal transduction system and/or HGF/c-Met signal transduction system. The method may further comprise a step of identifying the subject in need of preventing and/or treating a disease associated with Ang2/Tie2 signal transduction system and/or HGF/c-Met signal transduction system, before the step of administering.

The diseases associated with Ang2/Tie2 signal transduction system and/or HGF/c-Met signal transduction system may be a disease relating to angiogenesis and/or an increase in vascular permeability and/or overexpression of Ang2 and/or c-Met, and may be at least one selected from, but not be limited to, the group consisting of cancer; cancer metastasis; ocular blood vessel disorders such as retinopathy of prematurity, macular degeneration (e.g., age-related macular degeneration), diabetic retinopathy, neovascular glaucoma, etc.; inflammatory disorders such as psoriasis, rheumatoid arthritis, pneumonia, chronic inflammation, etc.; infectious disorders (infection); cardiovascular disorders such as hypertension, arteriosclerosis, etc.; renal disease; sepsis; asthma; edema; hereditary hemorrhagic telangiectasia (HHT), etc.

Another embodiment may provide a pharmaceutical composition for preventing and/or treating a cancer, wherein the composition includes the anti-c-Met/anti-Ang2 bispecific antibody as an active ingredient.

Another embodiment provides a method of preventing and/or treating a cancer in a subject, including administering the anti-c-Met/anti-Ang2 bispecific antibody to the subject (who is in need of preventing and/or treating a cancer). The anti-c-Met/anti-Ang2 bispecific antibody may be administered in a pharmaceutically effective amount for preventing and/or treating a cancer. The method may further include a step of identifying the subject in need of preventing and/or treating cancer, before the step of administering.

The prevention and/or treatment of a cancer may refer to prevention and/or treatment of a cancer and/or cancer metastasis.

The cancer may be a solid cancer or a blood cancer, and it may be at least one selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatocellular cancer, gastrointestinal cancer, gastric cancer, pancreatic cancer, glioblastoma, cervical cancer, ovarian cancer, liver cancer, bladder cancer, hepatoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like, but not limited thereto. In particular, the cancer may be one having a resistance against a preexisting anticancer drug, such as an antagonist (e.g., an anti-c-Met antibody) to c-Met or an antagonist (e.g., an anti-Ang2 antibody) to Ang2. The cancer may be a primary cancer or a metastatic cancer.

Another embodiment provides a pharmaceutical composition for normal blood vessel formation, comprising an anti-c-Met/anti-Ang2 bispecific antibody as an active ingredient. Another embodiment provides a method of increasing normal blood vessel formation in a subject, comprising administering an anti-c-Met/anti-Ang2 bispecific antibody to the subject (who is in need of increasing normal blood vessel formation). The anti-c-Met/anti-Ang2 bispecific antibody may be administered in a pharmaceutically effective amount for increasing normal blood vessel formation. The method may further include a step of identifying the subject in need of increasing normal blood vessel formation, before the step of administering.

Another embodiment provides a pharmaceutical composition for preventing and/or treating a disease relating to a decrease in normal blood vessel formation, comprising an anti-c-Met/anti-Ang2 bispecific antibody as an active ingredient. Another embodiment provides a method of preventing and/or treating a disease relating to a decrease in normal blood vessel formation in a subject, comprising administering an anti-c-Met/anti-Ang2 bispecific antibody to the subject (who is in need of preventing and/or treating a disease relating to a decrease in normal blood vessel formation). The anti-c-Met/anti-Ang2 bispecific antibody may be administered in a pharmaceutically effective amount for preventing and/or treating a disease relating to a decrease in normal blood vessel formation. The method may further include a step of identifying the subject in need of preventing and/or treating a disease relating to a decrease in normal blood vessel formation, before the step of administering.

The disease related to a decrease in normal blood vessel formation may be a disease that requires the induction of normal blood vessel formation and may be selected from the group consisting of ischemic disorders such as myocardial infarction, angina, cerebral infarction, stroke (ischemic stroke), etc., Buerger' disease (thromboangiitis obliterans), avascular necrosis, foot ulcer (e.g., diabetic foot ulcer), erectile dysfunction, and so on, but not be limited thereto.

Another embodiment provides a pharmaceutical composition for tissue regeneration and/or wound healing, comprising an anti-c-Met/anti-Ang2 bispecific antibody as an active ingredient. Another embodiment provides a method for tissue regeneration and/or wound healing in a subject, comprising administering anti-c-Met/anti-Ang2 bispecific antibody to the subject. The anti-c-Met/anti-Ang2 bispecific antibody may be administered in a pharmaceutically effective amount for tissue regeneration and/or wound healing. The subject may be in need of tissue regeneration and/or wound healing. The method may further comprise a step of identifying a subject who is in need of tissue regeneration and/or wound healing, prior to the administration step. A subject may be a subject who has a skin tissue damage or organ tissue damage or has received a skin transplant.

In the pharmaceutical composition or method, the anti-c-Met/anti-Ang2 bispecific antibody may be administered together with one or more additives selected from the group consisting of pharmaceutically acceptable carriers, diluents, excipients, and the like.

The pharmaceutically acceptable carrier may be any one commonly used in the formulation of drugs, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition may further include one or more selected from the group consisting of a diluent, an excipient, a lubricant, a wetting agent, a sweetener, a flavor enhancer, an emulsifying agent, a suspension agent, and a preservative.

The pharmaceutical composition or the anti-c-Met/anti-Ang2 bispecific antibody may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the composition may be administered using an optional device that enables an active substance to be delivered to target cells.

The suitable dose of the pharmaceutical composition or the anti-c-Met/anti-Ang2 bispecific antibody may be prescribed in a variety of ways, depending on factors such as formulation methods, administration methods, age of subjects, body weight, gender, pathologic conditions, diets, administration time, administration interval, administration route, excretion speed, and reaction sensitivity. For example, a daily dosage of the composition or the anti-c-Met/anti-Ang2 bispecific antibody may be within the range of about 0.001 to about 1000 mg/kg (e.g., about 0.001 mg/kg, about 0.01 mg/kg, about 1 mg/kg, or about 10 mg/kg), particularly about 0.01 to about 100 mg/kg (e.g., about 0.01 mg/kg, about 0.1 mg/kg, about 0.5 mg/kg, about 1 mg/kg, or about 5 mg/kg), and more particularly about 0.1 to about 50 mg/kg (e.g., about 0.1 mg/kg, about 1 mg/kg, about 10 mg/kg, or about 50 mg/kg), but is not limited thereto. The daily dosage may be formulated into a single formulation in a unit dosage form or formulated in suitably divided dosage forms, or it may be manufactured to be contained in a multiple dosage container. The term "pharmaceutically effective amount" as used herein refers to a content or dose of an active ingredient capable of showing desirable pharmacological effects and it may be determined in a variety of ways, depending on factors such as formulation methods, administration methods, age of subjects, body weight, gender, pathologic conditions, diets, administration time, administration interval, administration route, excretion speed, and reaction sensitivity.

The pharmaceutical composition or the anti-c-Met/anti-Ang2 bispecific antibody may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

Since the anti-Ang2 antibody or an antigen-binding fragment thereof comprised in the active ingredient of the pharmaceutical composition, i.e., the anti-c-Met/anti-Ang2 bispecific antibody, can be further activated by binding to Ang2, the pharmaceutical composition may also comprise Ang2 in addition to the anti-c-Met/anti-Ang2 bispecific antibody, to increase the function of the anti-Ang2 antibody or an antigen-binding fragment thereof. In addition, the method may further comprise a step of administering Ang2 to the subject, for example, in a pharmaceutically effective amount, simultaneously with the anti-c-Met/anti-Ang2 bispecific antibody or sequentially in any order.

In addition, the pharmaceutical composition or the anti-c-Met/anti-Ang2 bispecific antibody may be administered as an individual drug, or together with other drugs, and may be administered sequentially or simultaneously with pre-existing drugs.

In particular, the pharmaceutical composition including an antibody or an antigen-binding fragment thereof may be formulated into an immunoliposome since it contains an antibody or an antigen-binding fragment. A liposome containing an antibody may be prepared using any methods widely known in the art. The immunoliposome may be a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide-exchange reaction.

The subject to whom the pharmaceutical composition of the anti-c-Met/anti-Ang2 bispecific antibody is administered may be mammals, for example, primates such as humans and monkeys, or rodents such as rats and mice, or a cell or a tissue isolated from the mammal or a culture thereof, but are not be limited thereto. The subject may be a cancer patient having resistance against pre-existing anticancer drugs, for example, antagonists (e.g., an antibody) against a cancer-related target (e.g., c-Met, Ang2, etc.).

The anti-c-Met/anti-Ang2 antibody possesses both characteristics as an inhibitor against Ang2/Tie2 signal transduction and c-Met/HGF signal transduction, and may exhibit the following effects of:

1. Increasing the therapeutic efficacy compared to administration of Ang2/Tie2 inhibitor alone, HGF/c-Met inhibitor alone, or a combination thereof, thereby decreasing the administration amount thereof.

2. having an effect of inhibiting cancer metastasis as well as an effect of inhibiting cancer cell growth.

3. exhibiting an anticancer effect even on a cancer having a resistance to a pre-exiting anti-c-Met antibody and/or anti-Ang2 antibody.

4. being capable of being applied to a disease associated with Ang2/Tie2 signal transduction and HGF/c-Met signal transduction, other than cancers.

Also provided herein is a nucleic acid encoding the anti-c-Met/anti-Ang2 bispecific antibody described herein, optionally in a vector. The nucleic acid or vector can be in a cell.

The term "vector" used herein refers to a means for expressing a target gene in a host cell. For example, it includes a plasmid vector, a cosmid vector, and a virus vector such as a bacteriophage vector, an adenovirus vector, a retrovirus vector and an adeno-associated virus vector. Suitable recombinant vectors may be constructed by manipulating plasmids often used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4λB, λ-Charon, λΔz1, and M13), or a virus (for example, SV40).

The recombinant vector including the nucleic acid encoding the anti-c-Met/anti-Ang2 bispecific antibody may include the polynucleotides encoding the protein complex and an expression regulating factor (sequence) such as promoter, which are operatively linked to each other. The term "operatively linked" used herein refers to a functional linkage between a nucleotide expression regulating sequence (for example, a promoter sequence) and other nucleotide sequences. Thus, the expression regulating sequence may regulate the transcription and/or translation of the other nucleotide sequences by being operatively linked.

The recombinant (or expression) vector may be constructed typically for either cloning or expression. The recombinant vector may be made from any vector known in the pertinent art for expressing an exogenous protein in plants, animals, or microorganisms. The recombinant vector may be constructed using various methods generally known in the art.

The recombinant vector may be transformed or transfected into s host cell, such as, a prokaryotic cell or a eukaryotic cell. For example, when a prokaryotic cell is used as a host cell, the recombinant vector used generally includes a strong promoter capable of initiating transcription (for example, pL$^\lambda$ promoter, CMV promoter, trp promoter, lac promoter, tac promoter, T7 promoter, etc.), a ribosome binding site for initiating translation, and a transcription/translation termination sequence. When a eukaryotic cell is used as a host cell, the vector used generally includes the origin of replication acting in the eukaryotic cell, for example, a f1 replication origin, a SV40 replication origin, a pMB1 replication origin, an adeno replication origin, an AAV replication origin, or a BBV replication origin, but is not limited thereto. A promoter in an expression vector for a eukaryotic host cell may be a promoter derived from the genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV). A transcription termination sequence in an expression vector for a eukaryotic host cell may be, in general, a polyadenylation sequence.

A recombinant cell may obtained by transfecting (or transforming) the recombinant vector into a suitable host cell. Any host cells known in the pertinent art that enable stable and continuous cloning or expression of the recombinant vector may be used as the hose cell. Suitable prokaryotic host cells may include *E. coli* JM109, *E. coli* BL21, *E. coli* RR1, *E. coli* LE392, *E. coli* B, *E. coli* X 1776, *E. coli* W3110, *Bacillus* species strains such as *Bacillus subtillis* or *Bacillus thuringiensis*, intestinal bacteria and strains such as *Salmonella typhymurum, Serratia marcescens*, and various *Pseudomonas* species. Suitable eukaryotic host cells to be transformed may include yeasts, such as *Saccharomyce cerevisiae*, insect cells, plant cells, and animal cells, for example, Sp2/0, Chinese hamster ovary (CHO) K1, CHO, CHO-s, HEK293, HEK293f, DG44, PER.C6, W138, BHK, COS-7, 293, HepG2, Huh7, 3T3, RIN, and MDCK cell lines, but are not limited thereto.

The polynucleotide or the recombinant vector including the same may be transferred (transfected or transformed) into a host cell by using known transfer methods. Suitable transfer methods for prokaryotic host cells may include a method using $CaCl_2$ and electroporation. Suitable transfer methods for eukaryotic host cells may include microinjection, calcium phosphate precipitation, electroporation, liposome-mediated transfection, and gene bombardment, but are not limited thereto.

A transformed or transfected host cell may be selected using a phenotype expressed by a selected marker by any methods known in the art. For example, if the selected marker is a gene that is resistant to a specific antibiotic, a transformant may be easily selected by being cultured in a medium including the antibiotic.

Further provided is a method of preparing an anti-c-Met/anti-Ang2 bispecific antibody as described herein by expressing a nucleic acid encoding the anti-c-Met/anti-Ang2 bispecific antibody in a cell. The anti-c-Met/anti-Ang2 bispecific antibody can be isolated from the cell and purified to any desired degree. The step of expressing a gene may be performed in vitro. The step of expressing a gene may comprise culturing the recombinant cell in a medium for the cell and under conditions allowing expression of the gene in the cell, wherein the medium and conditions can be any known in the art for similar purposes. In addition, the method may further comprise harvesting (obtaining or separating) the polypeptide of interest from the expressing or culturing product, after the step of expressing or culturing. The step of harvesting the polypeptide of interest may be performed by separating the polypeptide from the recombinant cell, a lysate thereof, and/or a culture media (in case the polypeptide is secreted to a medium). The method of producing may further comprise an additional step, such as a step of purification and/or modification, so that the harvested polypeptide can have a desired quality and/or purity.

EXAMPLES

Hereafter, the present invention will be described in detail by examples.

The following examples are intended merely to illustrate the invention and are not construed to restrict the invention.

Reference Example 1: Construction of an Anti-c-Met Antibody 1.1. Production of "AbF46", a Mouse Antibody to c-Met
1.1.1. Immunization of a Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of a Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1\sim2 \times 10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, under Accession No. KCLRF-BP-00220 according to the Budapest Treaty (see Korean Patent Laid-Open Publication No. 2011-0047698).

1.1.4. Production and Purification of a Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) fetal bovine serum (FBS) were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody was stored in PBS before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Reference Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen), and a vector from the pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (IgBLAST online database tool, maintained by National Center for Biotechnology Information (NCBI), Bethesda, Md.) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a BLAST search. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of 5×10⁵ cells/ml. After 24 hours, when the cell number reached 1×10⁶ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% CO$_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of an scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 6, below.

TABLE 6

| CDR | Amino Acid Sequence |
| --- | --- |
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of an Antibody with Improved Affinity from Libraries

After maturation of the affinity of the constructed libraries for c-Met, the nucleotide sequence of scFv from each clone was analyzed. The nucleotide sequences thus obtained are summarized in Table 7 and were converted into IgG forms.

Four antibodies which were respectively produced from clones L3-1, L3-2, L3-3, and L3-5 were used in the subsequent experiments.

TABLE 7

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA: light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of (a) a heavy chain including the heavy chain variable region of huAbF46-H4-A1, U6-HC7 hinge, and the constant region of human IgG1 constant region, and (b) a light chain including the light chain variable region of huAbF46-H4-A1 and human kappa constant region. The antibody huAbF46-H4-A1 (IgG2 hinge) was composed of (a) a heavy chain including a heavy chain variable region, a human IgG2 hinge region, and a human IgG1 constant region, and (b) a light chain including the light chain variable region of huAbF46-H4-A1 and a human kappa constant region. The antibody huAbF46-H4-A1 (IgG2 Fc) was composed of (a) the heavy chain variable region of huAbF46-H4-A1, a human IgG2 hinge region, and a human IgG2 constant region, and (b) a light chain including the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a vector from the pOptiVEC™-TOPO TA Cloning Kit enclosed in an OptiCHO™ Antibody Express Kit (Cat no. 12762-019, Invitrogen) while DNA fragments having light chain nucleotide sequences were inserted into a vector from the pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the following examples, and referred as L3-1Y-IgG2.

Reference Example 2: Preparation of an Anti-Ang2 Antibody 2.1. Preparation of a Hybridoma A human Ang2 protein (R&D systems; 623-AN-025/CF) was administered to 5-week-old BALB/c mice along with an adjuvant to induce an immune response and then, hybridomas that produce an individual anti-Ang2 antibody were prepared according to the known methods described by Schwaber, et al. (Schwaber, J and Cohen, E. P., "Human x Mouse Somatic Cell Hybrid Clones Secreting Immunoglobulins of Both Parental Types," Nature, 244 (1973), 444-447).

More specifically, to obtain immunized mice necessary for developing hybridoma cell lines, 100 ug of human Ang2 protein (R&D Systems) mixed with the same amount of a complete Freund's adjuvant was administered via an intraperitoneal injection to each of five 4-6-week-old BALB/c mice (Japan SLC, Inc.). After two weeks, the antigen (half the previously injected amount) mixed with an incomplete Freund's adjuvant using the same method as described above was administered to each mouse via an intraperitoneal injection. After one additional week, a final boosting was performed and three days later, blood was collected from the tail of each mouse to obtain serum, which was then diluted at 1/1000 with PBS and subjected to an ELISA to verify that the titer of an antibody recognizing Ang2 was increased. From the results, mice in which a sufficient amount of the antibody was obtained were selected, and a cell fusion process was performed on the selected mice.

Three days before the cell fusion experiment, a mixture of 50 ug of PBS and 100 ug of human Ang2 protein (R&D systems) was administered via an intraperitoneal injection to BALB/c mice (Japan SLC, Inc.), and after each immunized mouse was anesthetized, its spleen located on the left side of the body was extracted. The extracted spleen was ground with a mesh to isolate cells, which were mixed with a culture medium (DMEM, Hyclon) to prepare a spleen cell suspension. The suspension was centrifuged to collect a cell layer. The obtained $1 \times 10^8$ spleen cells were mixed with $1 \times 10^7$ myeloma cells (Sp2/0), and the mixture was centrifuged to precipitate the cells. The centrifuged precipitate was slowly dispersed, treated with 1 ml of 45% polyethylene glycol (PEG 1500) contained in a culture medium (DMEM), and maintained at 37° C. for one minute before adding 1 ml of a culture medium (DMEM). Subsequently, 10 ml of the culture medium (DMEM) was added for 1 minute to the resultant, which was incubated in a water bath at 37° C. for 5 minutes and then re-centrifuged after the total volume was adjusted to 50 ml. The resulting cell precipitate was re-suspended in an isolation medium (HAT medium) at a concentration of $1 \sim 2 \times 10^5$/ml, and the resultant suspension was distributed at 0.1 ml to the each well of a 96-well plate, which was then incubated in a carbon dioxide incubator at 37° C. to prepare the hybridoma cell groups.

2.2. Selection of Anti-Ang2 Antibody Producing Clone and Purification of Antibody The above obtained individual antibody producing hybridomas were screened using a typical ELISA format to select hybridomas which produce 95 anti-Ang2 monoclonal antibodies among the hybridomas differentiated from their mother hybridomas, based on their binding potential with Ang2.

More specifically, to select the hybridoma cells that specifically react only to Ang2 protein among the hybridoma cell groups prepared in Reference Example 2.1 above, an ELISA assay method using a human Ang2 protein as an antigen was used for screening.

Human Ang-2 protein was added to a microtiter plate at the amount of 100 ng per each well to be adhered to the surface of the plate, and unreacted antigens were removed by washing. 50 μl of the hybridoma cell culture obtained in Reference Example 2.1 above was added to each well to react for 1 hour and then, the wells were sufficiently washed with phosphate buffered saline-TWEEN 20 (PBST) solution to remove unreacted culture solution. Goat anti-mouse IgG-horseradish peroxidase (goat anti-mouse IgG-HRP) was added thereto, a reaction was allowed to occur at a room temperature for 1 hour and then, washing was sufficiently performed with the TBST solution. Subsequently, substrate solution (OPD) of peroxidase was added to each well to react, and the reaction degree was measured by the absorption at 450 nm using an ELISA reader to repeatedly select hybridoma cell lines that secret antibodies having specifically high binding affinity only to human Ang2 protein. A limiting dilution was performed on the hybridoma cell lines obtained through repetitive selection to obtain final 58 clones of hybridoma cell lines producing monoclonal antibodies. The prepared hybridomas were deposited in the Korean Cell Line Bank located at Yongon-dong, Chongno-gu, Seoul, South Korea, as of Apr. 23, 2013 and received accession number KCLRF-BP-00295.

Each hybridoma obtained above was cultured in DMEM (Dulbeco's Modified Eagle's Medium) and then, the culture solutions were collected and subjected to Protein G-affinity chromatography method to purify anti-Ang2 monoclonal antibodies produced from each hybridoma.

First, the hybridoma cells cultured in 50 ml of culture medium (DMEM) containing 10% (v/v) FBS were centrifuged to obtain a cell precipitate, which was washed at least twice with 20 ml of PBS to remove the FBS. The cell precipitate was re-suspended in 50 ml of the culture medium (DMEM) and then incubated in a carbon dioxide incubator at 37° C. for 3 days. Subsequently, the cell culture was centrifuged to remove the antibody-producing cells, and the culture medium including the secreted antibodies was isolated and then, stored at 4° C. or used directly. Antibodies were purified from 50 to 300 ml of the culture medium using an AKTA purification device (GE Healthcare) equipped with an affinity column (protein G agarose column; Pharmacia, USA). The purified antibodies were stored for subsequent use after replacing the supernatant with PBS using a filter for protein aggregation (Amicon). One of the antibodies obtained from the hybridomas above was named 10D6.

The binding affinity of the above antibody to human Ang-2 protein was measured by an SPR method using a BIAcore T100 (GE Healthcare). The SPR method uses refractive index change of light which passes a sensor chip according to the state of materials coated onto the sensor chip, and if an antigen or an antibody is flowed onto a chip coated with the antigen or antibody, it causes changes in refractive index due to their binding and Kd values are thus calculated from the measured values.

First, anti-His antibody was immobilized on a CM5 sensor chip (GE healthcare) up to 8,000 RU levels using a pH 5.0 acetate solution and an amine coupling kit (GE Healthcare). 6 μg/ml of a recombinant hAng-2 (C-His, R&D Systems) protein was flowed onto the chip to be captured at 100 to 200 RU levels. The antibody obtained in Example 2 above was diluted serially from 100 nM concentration and flowed onto the chip to allowing the antibody to bind to (on), dissociate from (off), and regenerate (using 10 mM NaOH solution) from the antigen captured on the sensor chip, thereby measuring antigen-antibody affinity. With regard to hAng2, such experiments were conducted, and the results are as shown in the following Table 8.

TABLE 8

| Antibody | hAng2 (Kd) |
| --- | --- |
| SAIT-ANG2-AB-m10D6 | 8.0 nM |

2.3. Cloning of Genes of an Anti-Ang2 Antibody

A whole RNA was obtained using RNeasy mini kit (Qiagen) from the antibody-producing hybridoma ($2 \times 10^6$ cells) obtained from Reference Example 2.2 above. Then, by using this as a template, only the gene sequence of the heavy chain and light chain variable regions of the monoclonal antibody to be produced in the hybridoma was amplified using a OneStep RT-PCR kit (Qiagen), a Mouse Ig-Primer Set (Novagen), and a thermocycler (GeneAmp PCR System 9700, Applied Biosystem) under the following conditions: 5 min. at 94° C.; [30 min. at 50° C., 15 min. at 95° C.], [1 min. at 94° C., 1 min. at 50° C., 2 min. at 72° C.]×35 cycles; 6 min. at 72° C.; cooling to 4° C.

The PCR products obtained from each reaction were subjected to a direct DNA sequencing to obtain the CDR, heavy chain variable regions (wherein the 113th amino acid "S" is substituted with "L") and light chain variable regions of the antibody, and nucleotide sequences encoding them, and the obtained results are set forth in the following Tables 9 to 12.

TABLE 9

| | heavy chain CDR sequence | | |
| --- | --- | --- | --- |
| Antibody | CDRH1-KABAT | CDRH2-KABAT | CDRH3-KABAT |
| SAIT-ANG2-AB-m10D6 | SDYAWN (SEQ ID NO: 109) | YINYSGNTDYNPSLKS (SEQ ID NO: 110) | GNFEGAMDY (SEQ ID NO: 111) |

TABLE 10

| | light chain CDR sequence | | |
| --- | --- | --- | --- |
| Antibody | CDRL1-KABAT | CDRL2-KABAT | CDRL3-KABAT |
| SAIT-ANG2-AB-m10D6 | KASQSVSNDVA (SEQ ID NO: 112) | YASNRYP (SEQ ID NO: 113) | QQDYSSPWT (SEQ ID NO: 114) |

TABLE 11

| Antibody | heavy chain variable region sequence |
|---|---|
| SAIT-ANG2-AB-m10D6 | DVQLQESGPDLVKPSQSLSLTCTVTGYSITSDYAWNWIRQFPGNKLE<br>WMGYINYSGNTDYNPSLKSRSSITRDTSKNQFFLQLNSVTTGDTATY<br>YCARGNFEGAMDYWGQGTSVTVSS(SEQ ID NO: 115)<br><br>GATGTGCAGCTTCAGGAGTCGGGACCTGACCTGGTGAAACCTTCT<br>CAGTCTCTGTCCCTCACCTGCACTGTCACTGGCTACTCAATCACCA<br>GTGATTATGCCTGGAACTGGATCCGGCAGTTTCCAGGAAACAAAC<br>TGGAGTGGATGGGCTACATAAACTACAGTGGTAACACTGACTACA<br>ACCCATCTCTCAAAAGTCGAAGCTCTATCACTCGAGACACATCCA<br>AGAACCAGTTCTTCCTGCAGTTGAATTCTGTGACTACTGGGGACA<br>CAGCCACATATTACTGTGCAAGAGGTAACTTCGAAGGTGCTATGG<br>ACTACTGGGGTCAAGGAACCTCAGTCACCGTCTCCTCA(SEQ ID<br>NO: 116) |

TABLE 12

| Antibody | light chain variable region sequence |
|---|---|
| SAIT-ANG2-AB-m10D6 | SIVMTQTPKFLLVSAGDRVTITCKASQSVSNDVAWYQQKPGQSPK<br>LLIYYASNRYPGVPDRFTGSGYGTDFTFTISTVQAEDLAVYFCQQD<br>YSSPWTFGGGTKLEIK(SEQ ID NO: 117)<br><br>AGTATTGTGATGACCCAGACTCCCAAATTCCTGCTTGTATCAGCA<br>GGAGACAGGGTTACCATAACCTGCAAGGCCAGTCAGAGTGTGA<br>GTAATGATGTAGCTTGGTACCAACAGAAGCCAGGGCAGTCTCCT<br>AAACTGCTGATATACTATGCATCCAATCGCTACCCTGGAGTCCCT<br>GATCGCTTCACTGGCAGTGGATATGGGACGGATTTCACTTTCAC<br>CATCAGCACTGTGCAGGCTGAAGACCTGGCAGTTTATTTCTGTC<br>AGCAGGATTATAGCTCTCCGTGGACGTTCGGTGGAGGCACCAAG<br>CTGGAAATCAAA(SEQ ID NO: 118) |

(In above Tables 11 and 12, underlined bold letters are CDR1, CDR2, and CDR3 in sequence)

2.4. Competition ELISA Assay of 10D6 Antibody Against Ang2-Tie2 Binding

Ang2-Tie2 binding competition ELISA was conducted using the antibody binding to Ang-2 prepared in Reference Example 2.3 above.

More specifically, MaxiSorp™ flat-bottom plate (Nunc) of 96-well was coated with hTie2-Fc (R&D Systems) which is a protein bound with 4 μg/ml of Fc of human IgG1. After that, the plate was washed five times with 0.05% (v/v) Tween-20-containing PBS (phosphate buffer saline) and then blocked with 1% (v/v) BSA (bovine serum albumin; Sigma)-containing PBS at a room temperature for 2 hour.

For Ang2:Tie2 competition ELISA, each anti-Ang2 antibody obtained in Example 2 was placed at various concentrations of 400 nM-0.001 nM into each well coated with the hTie-2/Fc fusion protein along with 1% (v/v) BSA and 400 ng/ml of a FLAG-tagged hAng-2 and then, the plate was allowed to react at a room temperature for 2 hours and washed five times with PBST. After that, an anti-FLAG antibody (Sigma) conjugated with HRP diluted in 1% (v/v) BSA-containing PBS at a ratio of 1:5,000 (v/v) was added in an amount of 100 μl to each well to react at a room temperature for 1 hour and then, the plate was washed five times with PBST. Lastly, 100 μl of TMB substrate (Cell Signaling) was added to each well of the plate to induce color development for 3 min. and then, the reaction was ceased by the addition of 100 μl of Stop solution (Cell Signaling) and OD450 values were measured on a plate reader (Molecular Devices).

For comparison, the same test was carried out using 4H10 which is an anti-Ang2 antibody inhibiting Ang2-Tie2 binding. The 4H10 is an antibody having the following heavy chain variable region and light chain variable region.

Heavy chain variable region (SEQ ID NO: 120):
EVQLLESGGGLVQPGGSLRLSCAASGFTFSSYDMSWVRQAPGKGLEWVS

LISPDSSSIYYADSVKGRFTISRDNSKNTLYLQMNSLRAEDTAVYYCAKD

LISFWRGGFDYWGQGTLVTVSS

Light chain variable region (SEQ ID NO: 121)
QSVLTQPPSASGTPGQRVTISCSGSSSNIGSNYVNWYQQLPGTAPKLLIY

ADSNRPSGVPDRFSGSKSGTSASLAISGLRSEDEADYYCGSWDYSLSGYV

FGGGTKLTVLG

Figure 2:
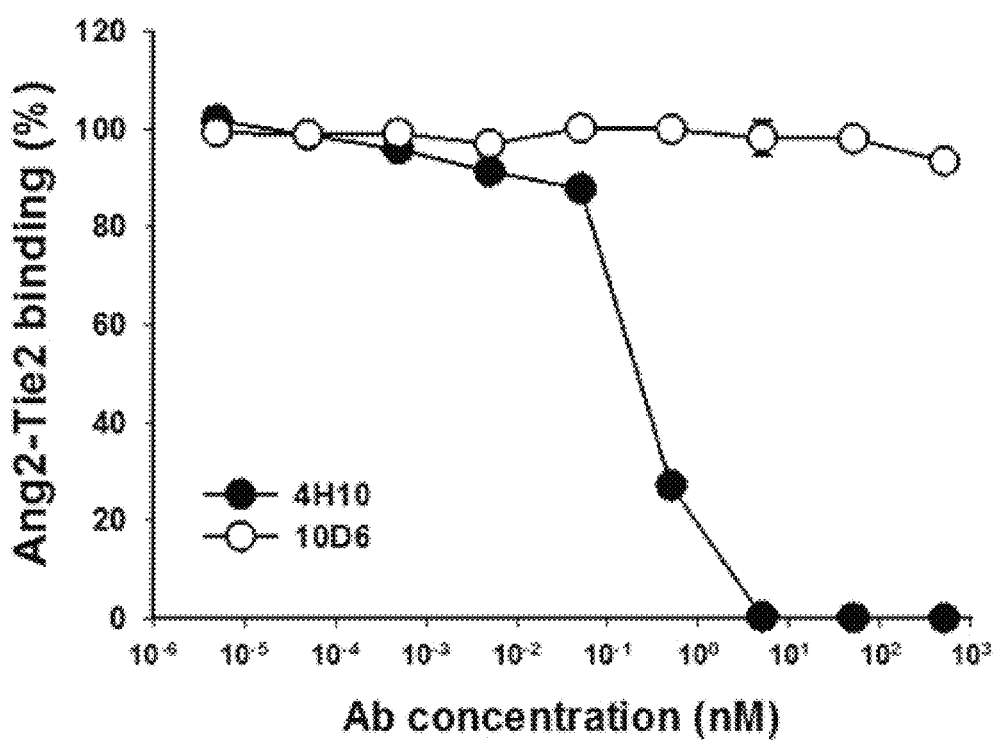
FIG. 2 provides results of Ang2-Tie2 competition ELISA showing the Ang2-Tie2 binding inhibition level depending on the concentration of an anti-Ang2 antibody.

An inhibitory degree (%) against Ang2-Tie2 binding is shown in FIG. 2. As seen in FIG. 2, unlike 4H10 which is an anti-Ang2 antibody inhibiting Ang2-Tie2 binding, the 10D6 antibody did not inhibit binding between Ang2-Tie2 receptor.

2.5. Verification of Antigen Recognizing Site (Epitope) of Ang2 Antibody

To verify the epitope (or specific binding site) of the anti-Ang2 antibody prepared in Reference Example 2.3, an ELISA was performed using a recombinant protein where a receptor binding domain (RBD) of Ang2 protein in the form of being tagged with Flag was mutated by artificial means.

Each well of a 96-well MaxiSorp™ flat-bottom plate (Nunc) was coated with 50 ul (microliter) of 1000 nM antibody. Then, the plate was washed five times with 0.05% (v/v) Tween-20-containing PBS (PBST) and blocked with 1% (v/v) BSA-containing PBS at a room temperature for 2 hours. 250 ng of each mutant Ang2 protein obtained by substituting S417, Q418, P419, N421, I434, D448, A449, P452, Y460, N467, K468, or F469 residue of Ang2 protein tagged with a FLAG sequence (DYKDDDDK (SEQ ID NO: 198), Sigma) at its N-terminal with alanine was added to each well of the plate, which was then allowed to react at a room temperature for 2 hours.

The plate was washed five times with 0.05% (v/v) Tween-20 containing PBS, reacted with an anti-FLAG antibody (SIGMA) conjugated with HRP which was diluted in 1% (v/v) BSA-containing PBS at a ratio of 1:5,000 (v/v) at a room temperature for 1 hour, and washed five times with 0.1% (v/v) Tween-20-containing PBS.

Finally, 50 ul of TMB substrates (Cell signaling) was added to each well of the plate to induce color development at a room temperature for 3 min. and the reaction was ceased by the addition of 50 ul of Stop solution (Cell signaling) and then, OD450 values were measured on a plate reader (Molecular Devices). By comparing binding affinities with mutated Ang2 to those of unmutated Ang2, each epitope of Ang2 antibodies was identified. The obtained measurement results of the binding affinities (%) with mutant Ang2 against the binding affinity with the native Ang2 are shown in the following Table 13.

TABLE 13

| | Loop 1 | | | | | Loop 2 | | | Loop 3 | | | Loop 4 |
|---|---|---|---|---|---|---|---|---|---|---|---|---|
| | 417 | 418 | 419 | 421 | 434 | 448 | 449 | 452 | 460 | 467 | 468 | 469 |
| 10D6 | 101.17 | 38.94 | 41.08 | 109.09 | 109.49 | 104.55 | 97.86 | 102.15 | 103.15 | 106.84 | 110.27 | 108.79 |

2.6. Phosphorylation Induction of Tie2 Receptor by 10D6 Antibody

As Ang2 induces a change in vascular endothelial cells by binding to a Tie-2 receptor expressed in the vascular endothelial cells to induce the phosphorylation of the receptor and activate it, a test for analyzing an influence of the anti-Ang2 antibody on Tie2 phosphorylation was conducted using a cell-based assay.

For this, HUVEC (ATCC) cells ($1 \times 10^6$) were cultured in a 100 mm culture dish using EGM-2 (Lonza) media at 37° C. and when they reached 80~90% confluency, the media were replaced with serum-free media and cultured at 37° C. for 6 to 16 hours. The dish was washed once with PBS and after the replacement with 1 nM sodium orthovanadate (Sigma)-mixed serum free media (Lonza), they were further cultured for 10 min. After washed once again with PBS, the cultured cells were treated with a mixture prepared by mixing the anti-Ang2 antibody (10D6) having various concentrations (600~0.06 nM) with 40 nM of Ang2 protein (R&D systems) and letting them stand for 20 min. and further cultured for 10 min. The cells were washed using PBS, treated with 400 μl of a lysis buffer (Roche), collected to a tube to be dissolved at 4° C. for 30 min. and then, centrifuged at 13,000 rpm for 15 min. to measure a supernatant using Nanodrop.

1 μg of Tie2 antibody (R&D system) was added to 0.8 mg of a cell lysate, which was then overnight reacted at 4° C. and then subjected to immunoprecipitation by the addition of protein A bead (GE Healthcare) thereto. The obtained reactant was centrifuged at 13,000 rpm for 15 min. to obtain a pellet, which was washed two to three times with a lysis buffer (Roche), added to a sample buffer (Invitrogen) mixed with a reducing agent, and boiled at 95° C. for 5 min., and then, applied to NuPAGE Novex 4-12% Bis-Tris gel (Invitrogen) and transferred onto nitrocellulose membrane (Invitrogen).

To see the presence of the phosphorylation of Tie2, the membranes were blocked with PBST mixed with 3% (v/v) skim milk (Sigma) for 30 min. and identified using an HRP-conjugated anti-phospho tyrosine antibody (Millipore). For Tie2 identification, the blots were reacted in a stripping buffer (Thermo) for 15 min, then blocked again and identified using an Tie2 antibody (Santa cruz).

Figure 3A:
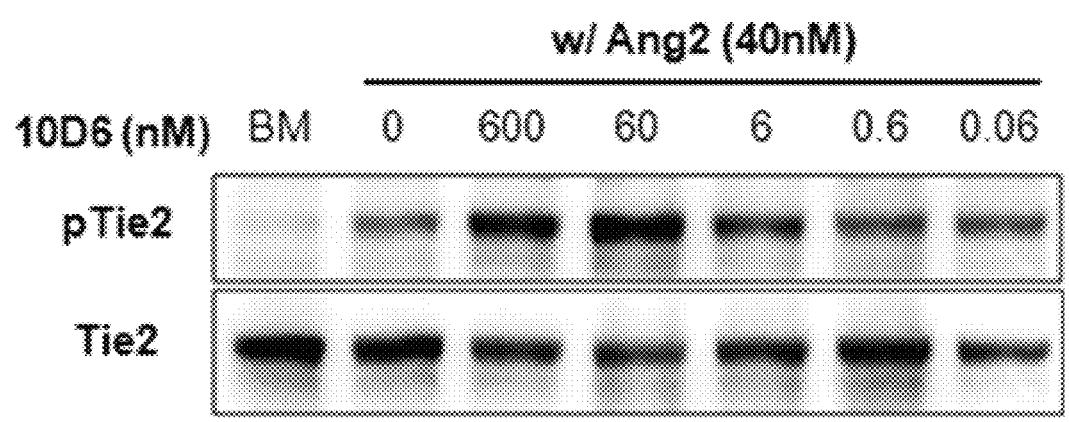
FIG. 3A provides results of immunoblotting showing the change in the level of Tie2 receptor and phosphorylated Tie2 receptor depending on the concentration of an anti-Ang2 antibody.

The obtained results are shown in FIG. 3A. As shown in FIG. 3A, when 10D6 antibody was added together with Ang2, the phosphorylation of Tie2 was more strongly induced at every antibody concentration range tested than the case in which Ang2 was treated alone.

Figure 3B:
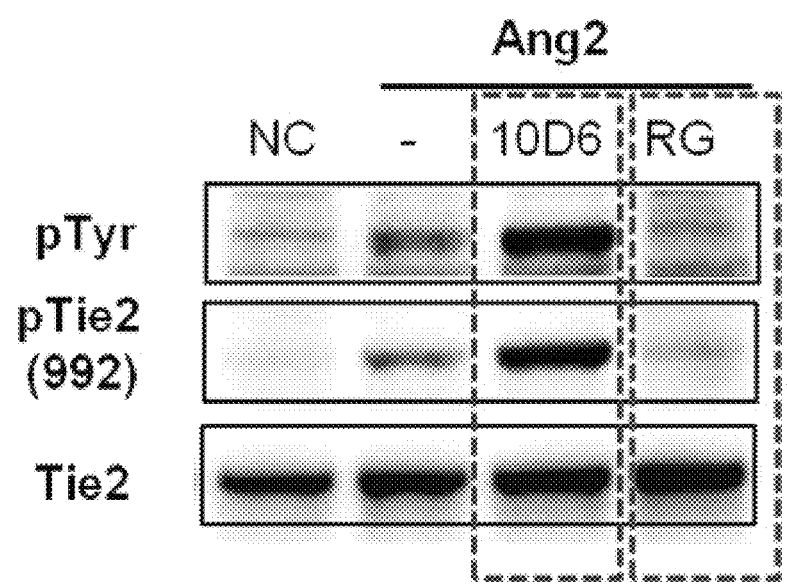
FIG. 3B provides results of immunoblotting showing the change in the level of Tie2 receptor and phosphorylated Tie2 receptor by an anti-Ang2 antibody compared to that of a control antibody (RG).

In addition, referring to the above method, when 60 nM of antibody 10D6 and Ang2 were treated, the phosphorylation level of Tie2 was measured and compared with the case of treating a control antibody (anti-Ang2 antibody (Regeneron) which has MOA of inhibiting binding between Ang2 and Tie2; represented as 'RG antibody'). The obtained immunoblotting results are shown in FIG. 3B. After treating with the antibody (10D6 or RG), the blot band density of pTyr and Tie2 was measured using ImageJ software and pTyr/Tie2 ratio was calculated. The obtained result is demonstrated in FIG. 3C.

Figure 3C:
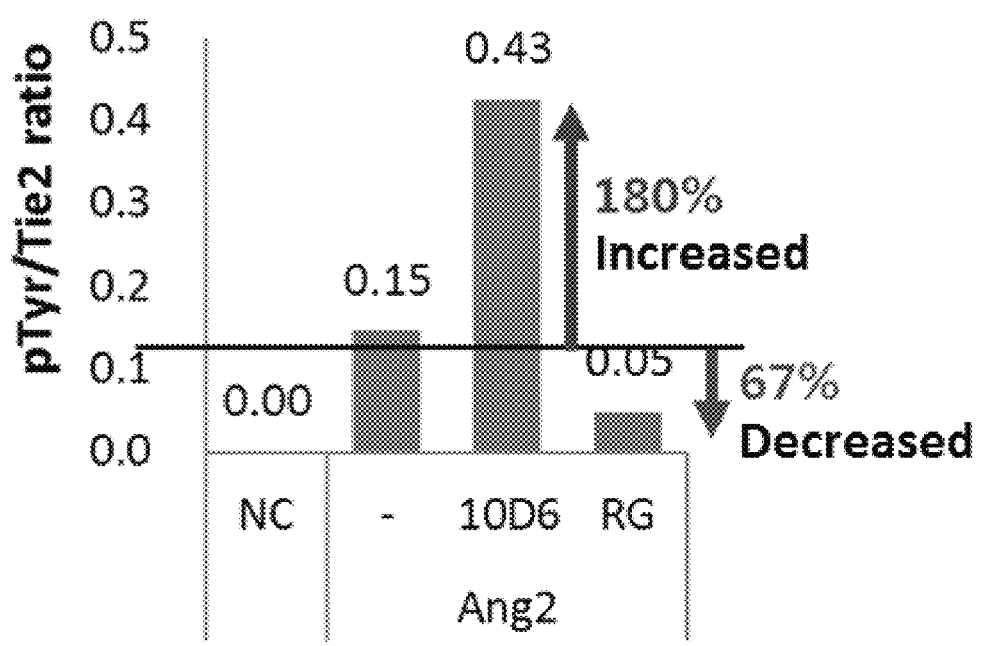
FIG. 3C is a graph showing the ratio of phosphorylated Tyr in Tie2 receptor.

As shown in FIGS. 3B and 3C, when treated with antibody 10D6, Tie2 phosphorylation level is increased by 180% compared to Ang2 treatment alone; whereas, when treated with control antibody RG, Tie2 phosphorylation level is decreased by 67% compared to Ang2 treatment alone, indicating that antibody 10D6 has about 8.6-fold higher Tie2 phosphorylation effect than control antibody. In FIGS. 3B and 3C "NC" represents Tie2 phosphorylation in untreated cells.

2.7. Activation Induction of Tie2 Signaling by 10D6 Antibody

To see whether 10D6 antibody induces the activation of the downstream signaling of a Tie2 receptor as well as the activation of the Tie2 receptor itself, the phosphorylation degrees of proteins participating in the downstream signaling when Ang2 alone or Ang2 and 10D6 antibody was treated were tested using immune blotting. To compare the activation degrees of the downstream signaling, the same test was conducted with regard to a group in which Ang1 (R&D systems), and Ang2 (R&D systems) and an anti-Ang2 antibody (RG antibody; control antibody having MOA inhibiting Ang2-Tie2 binding, Regeneron Co.) were treated together.

Specifically, HUVEC (ATCC) cells ($1 \times 10^6$) were cultured in a 6-well culture dish using EGM-2 (Lonza) media at 37° C. and when they reached 80~90% confluency, the media were replaced with serum-free media (Lonza) and cultured at 37° C. for 6 to 16 hours. The dish was washed once with PBS, and the cultured cells were treated with a mixture prepared by mixing 60 nM of the Ang2 antibody (10D6) with 40 nM of Ang2 protein (R&D systems) and letting them stand for 20 min. and further cultured for 30 min. For comparison, groups in which Ang1 (R&D systems) 4 nM, Ang2 (R&D systems) 40 nM, and Ang2 (R&D systems) 40 nM+anti-Ang2 antibody (Regeneron) 60 nM were treated respectively were prepared.

The cells were washed using PBS, treated with a lysis buffer (Roche), collected to a tube to be dissolved at 4° C.

for 30 min. and then, centrifuged at 13,000 rpm for 15 min. to measure a supernatant. A sample buffer (Invitrogen) mixed with a reducing agent was added to 25 µg of a cell lysate, which was boiled at 95° C. for 5 min., and then, applied to NuPAGE Novex 4-12% Bis-Tris gel (Invitrogen) and transferred onto nitrocellulose membrane (Invitrogen).

To see the presence of the phosphorylation of Akt, eNOS and 42/44 involved in the downstream signaling, the blots were blocked with PBST mixed with 3% (v/v) skim milk (Sigma) for 30 min. and then treated with an anti-pAkt antibody, anti-p-eNOS antibody, and anti-p-42/44 antibody (all of them; Cell signaling). The blots were reacted in a stripping buffer (Thermo) for 15 min. and then blocked again to identify Akt, eNOS, and 42/44 using an anti-Akt antibody, anti-eNOS antibody, and anti-42/44 antibody (all of them; Cell signaling).

Figure 4A:
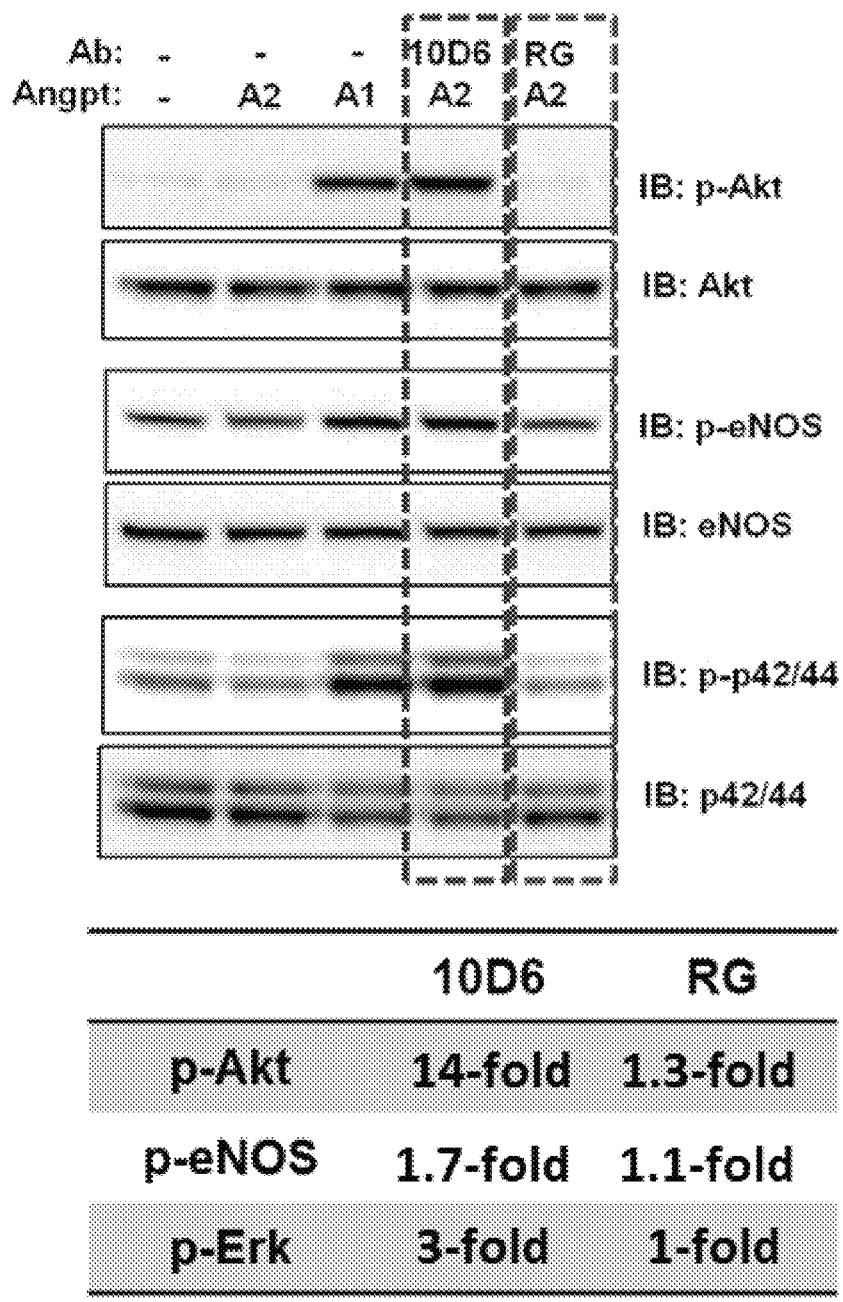
FIG. 4A provides results of immunoblotting showing the phosphorylation level of proteins relating to downstream signaling of Tie2 receptor by treatment of an anti-Ang2 antibody.

As shown in FIG. 4A, in the Ang1 only treatment group and the Ang2 and 10D6 co-treatment group, downstream signaling was strongly induced in comparison with the Ang2 only treatment group and the Ang2 and RG antibody co-treatment group, and the effects in the Ang2 and 10D6 antibody co-treatment group was at least equal to those in the Ang1 sole-treatment group.

In addition, the phosphorylation of Tie2 receptor and a protein (Akt) which participates in downstream signaling of Tie2 by treating anti-Ang2 antibody was measured in animal model (in vivo). More particularly, 5 mg/kg of antibody was injected alone or together with 20 µg of Ang2 into tail vein of 7-8 week old C57BL6 mouse, and 1 hour after, lung tissue was removed. The obtained lung tissue was subjected to homogenization lysis using lysis buffer (Roche) and Fast-Prep kit (MP biomedicals). Activities of Tie2 and Akt in the obtained tissue lysate were measured by the above-described method.

Figure 4B:
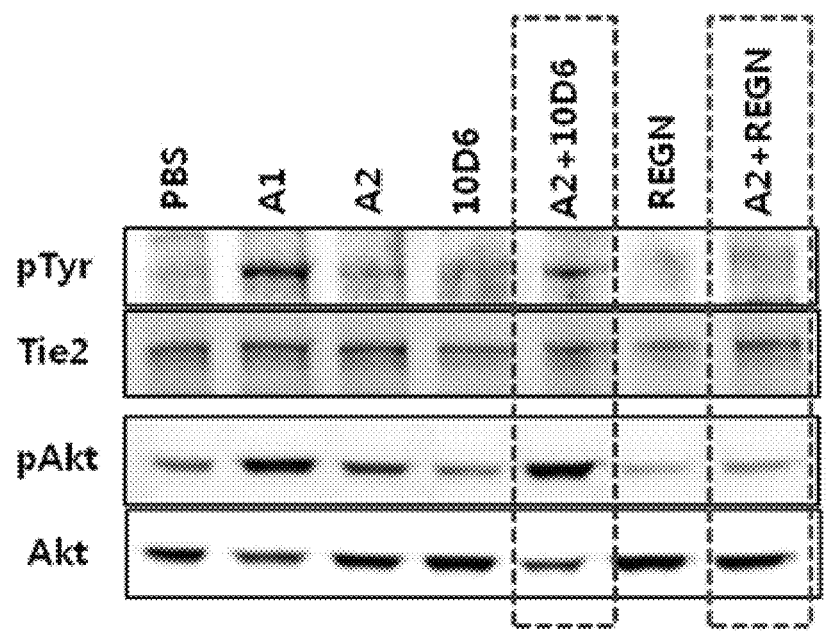
FIG. 4B provides results of immunoblotting showing the phosphorylation level of Tie2 receptor and Akt relating to downstream signaling of Tie2 receptor by treatment of an anti-Ang2 antibody in an animal model.
Figure 4C:
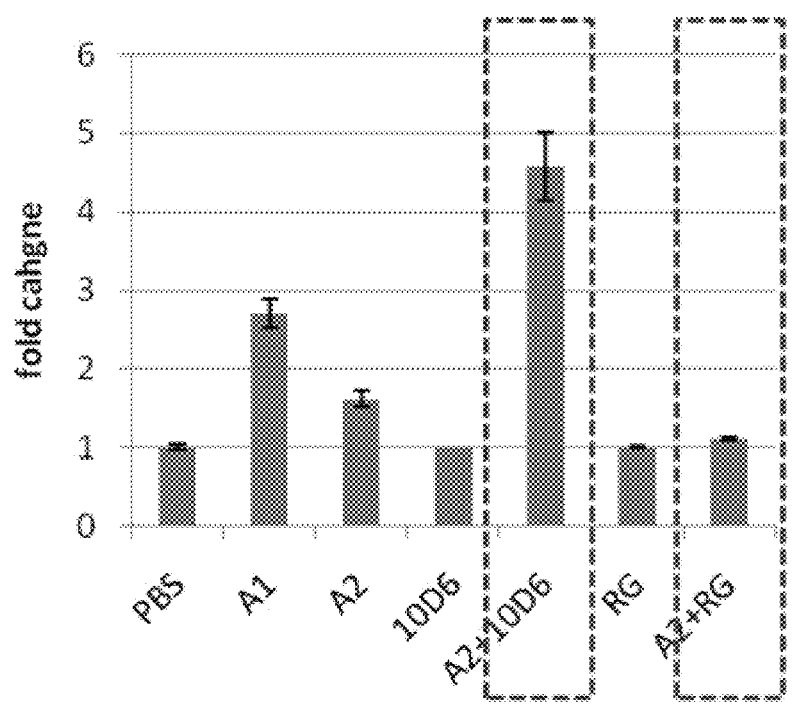
FIG. 4C is a graph showing the quantified results of FIG. 4B.

The obtained results are demonstrated in FIGS. 4B and 4C. In FIGS. 4B and 4C, "REGN" or "RG" represents a control antibody (anti-Ang2 antibody of Regeneron). As shown in FIGS. 3B and 3C, even in vivo experimentation, antibody 10D6 exhibits considerable effect of phosphorylating Tie2 and a protein, Akt, participating in downstream signaling of Tie2.

2.8. ELISA Assay for Identifying Formation of 10D6-Ang2-Tie2 Complex

As it was confirmed that 10D6 anti-Ang2 antibody activates Tie2 signaling without inhibiting Ang2-Tie2 binding, an ELISA was conducted to see whether a complex between the antibody and Ang2:Tie2 receptor is formed.

A 96-well MaxiSorp™ flat-bottom plate (Nunc) was coated with 4 µg/ml of Tie2-Fc (R&D systems) or BSA (Sigma). Then, the plate was washed five times with 0.05% (v/v) Tween-20-containing PBS (Phosphate Buffer Saline) and blocked with 1% (v/v) BSA (Bovine serum albumin; Sigma)-containing PBS at a room temperature for 2 hours. 0.25 µg/ml of Ang2 and 2 µg/ml of 10D6 antibody were added to each well of the plate, which was allowed to react at a room temperature for 2 hours and then washed five times with PBST. After that, an anti-mouse IgG antibody (Sigma) conjugated with HRP diluted in 1% (v/v) BSA-containing PBS at a ratio of 1:5,000 (v/v) was added in an amount of 100 ul to each well to react at a room temperature for 1 hour and then, the plate was washed five times with PBST. Lastly, 100 ul (microliter) of TMB substrate (Cell Signaling) was added to each well of the plate to induce color development for 3 min. and then, the reaction was ceased by the addition of 100 ul of Stop solution (Cell Signaling) and OD450 values were measured on a plate reader (Molecular Devices).

Figure 5:
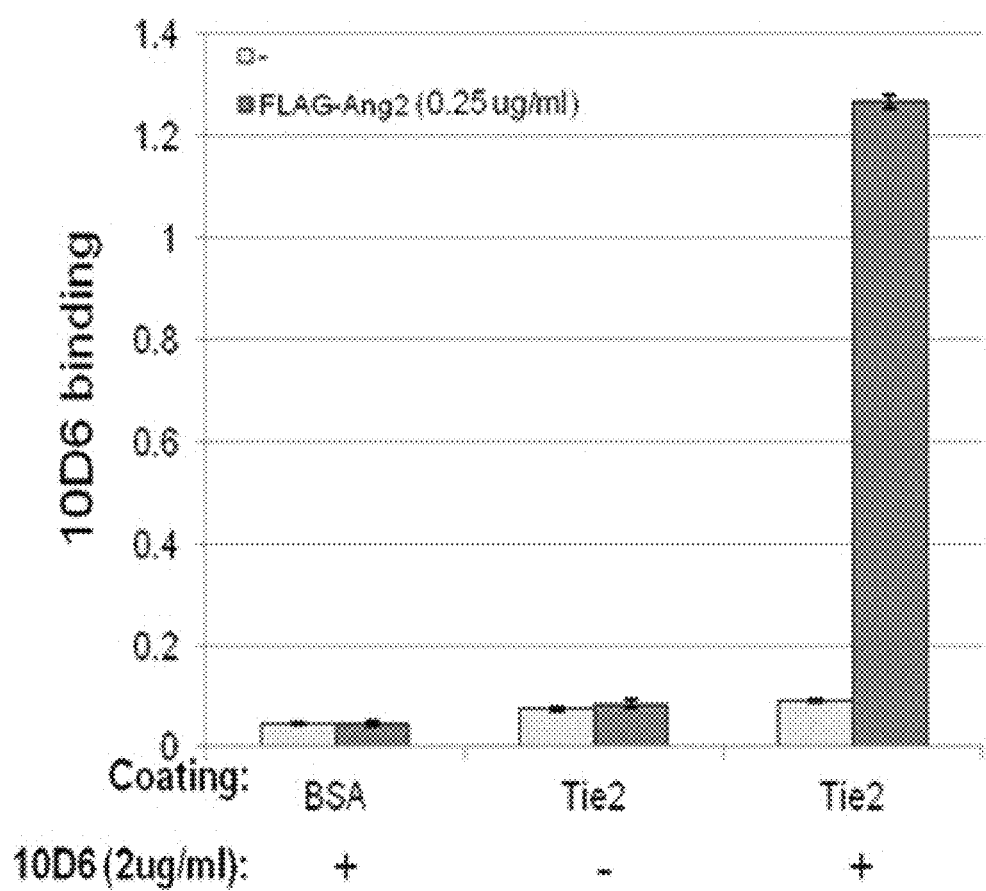
FIG. 5 is a graph showing the degree of binding between an anti-Ang2 antibody and Ang2.

The obtained results are shown in FIG. 5. As seen in FIG. 5, it was confirmed that 10D6 antibody formed a complex by binding to Ang2 which was bound to Tie2.

2.9. Preparation of an scFv of Mouse Antibody 10D6

A gene for producing an scFv fragment was designed using the heavy chain variable region and the light chain variable region of mouse antibody 10D6 prepared in Reference Example 2.3. The heavy chain variable region (amino acid sequence: SEQ ID NO: 115; coding nucleotide sequence: SEQ ID NO: 116) and the light chain variable region (amino acid sequence: SEQ ID NO: 117; coding nucleotide sequence: SEQ ID NO: 118) were linked to form 'VH-linker-VL' construct, and the linker is designed to have the amino acid sequence of 'GGGGSGGGGSGGGGS (SEQ ID NO: 184)'. The amino acid sequence of the designed 'VH-linker-VL' (scFv of 10D6) is represented in SEQ ID NO: 188 and the coding nucleotide sequence thereof is represented in SEQ ID NO: 189.

2.10. Preparation of Gene Library for Affinity Maturation 2.10.1. Selection of Target CDR and Preparation of Primers To perform affinity maturation, six complementary determining regions (CDRs) were defined from the prepared mouse antibody 10D6 according to the 'Kabat numbering' rule. The CDRs are summarized in Table 14:

TABLE 14

| CDR | Amino acid sequence |
| --- | --- |
| CDR-H1 | SDYAWN (SEQ ID NO: 109) |
| CDR-H2 | YINYSGNTDYNPSLKS (SEQ ID NO: 110) |
| CDR-H3 | GNFEGAMDY (SEQ ID NO: 111) |
| CDR-L1 | KASQSVSNDVA (SEQ ID NO: 112) |
| CDR-L2 | YASNRYP (SEQ ID NO: 113) |
| CDR-L3 | QQDYSSPWT (SEQ ID NO: 114) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of 10D6 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

2.10.2. Construction of Gene Library of scFv of 10D6 Antibody

Figure 6:
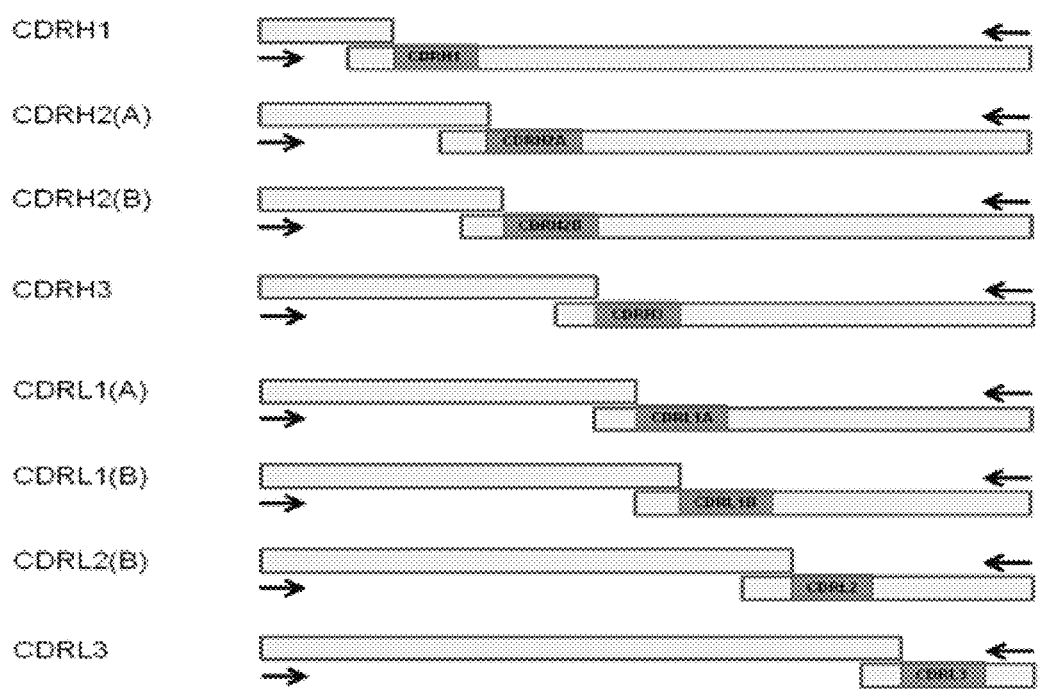
FIG. 6 schematically shows the process of overlap extension PCR (polymerase chain reaction) for establishing scFv library genes of 10D6 antibody variants wherein a certain desired CDR is modified.

The construction of antibody gene libraries through the introduction of random sequences was carried out using the primers synthesized in the same manner as in Reference Example 2.10.1. Two PCR products were obtained using a polynucleotide covering the 10D6 scFv (SEQ ID NO: 189) as a template (see FIG. 6), and were subjected to overlap extension PCR to give scFv library genes for 10D6 antibodies in which only desired CDRs were mutated. $10^7 \sim 10^8$ libraries targeting each of the six CDRs prepared from the scFv library genes were constructed.

The affinity for Ang2 of each library was compared to that of the wild-type. Most libraries were lower in affinity for Ang2, compared to the wild-type. However, in some mutants, the affinity for Ang2 was retained.

2.11. Selection of Antibody with Improved Affinity from Libraries

Among the scFv libraries provided in Reference Example 2.10, the scFv fragments showing upper 1.0 percent of affinity to Ang-2 were selected, and this process was repeated four times. The nucleotide sequence of each of the selected scFv was analyzed. The obtained nucleotide sequences are summarized in Table 15, and were converted into IgG forms (a heavy chain constant region: constant region of human IgG1, a light chain constant region: constant region of human KAPPA Chain). Five antibodies which were respectively produced from clones VH-6.6, VH-6.7, VL-(6.11), VL-(6.17), and VL-HU1(6.22) were used in the subsequent experiments.

TABLE 15

| Clone | Library constructed | CDR sequence |
|---|---|---|
| VH-6.6 | CDR-H2 | KISYSGKTDYNPSLKS (SEQ ID NO: 122) |
| VH-6.7 | CDR-H2 | KINYAGNTDYNPSLKS (SEQ ID NO: 123) |
| VL-(6.11) | CDR-L1 | KASQSVSNDVH (SEQ ID NO: 124) |
| VL-(6.17) | CDR-L3 | QHDYSSPFT (SEQ ID NO: 127) |
| VL-(6.22) | CDR-L1 + CDR-L3 | KASQSVSNDVH (SEQ ID NO: 124) + QHDYSSPFT (SEQ ID NO: 127) |

2.12. Preparation of Humanized Antibody 10D6-HU1, 10D6-HU2, 10D6-HU3, and 10D6-HU5, from Mouse Antibody 10D6

2.12.1. Heavy Chain Humanization)

To design three domains 10D6-HU1 Heavy, 10D6-HU2-heavy, and 10D6-HU5-heavy, human germline genes which share the highest identity/homology with the VH gene of the mouse antibody 10D6 purified were analyzed through an Ig BLAST (IgBLAST online database tool, maintained by National Center for Biotechnology Information (NCBI), Bethesda, Md.). The analysis results revealed IGHV4-b*01 (DP-67; accession number: Z12367) has an identity/identity/homology of 72% at the amino acid level. CDR-H1(SEQ ID NO: 109), CDR-H2(SEQ ID NO: 110), and CDR-H3(SEQ ID NO: 111) of the mouse antibody 10D6 were defined according to Kabat numbering. A design was made to introduce the CDR of the mouse antibody 10D6 into the framework of IGHV4-b*01 (named as 10D6-HU1, SEQ ID NO: 185; QVQLQESGPGLVKPSETLSLTCAVSGYSISSDYAWN-WIRQPPGKGLEWIGYINYSGN TDYNPSLKSRVTIS-VDTSKNQFSLKLSSVTAADTAVYYCARGNFEGAM-DYWGQGTL VTVSS). Hereupon, a back mutation to the amino acid sequence of the mouse 10D6 were conducted at positions 30 (S→T), to establish antibody 10D6-HU5 (SEQ ID NO: 164). Then, 10D6-HU5 was further mutated at positions 48 (I→M), 67 (V→S), and 71 (V→R), to establish 10D6-HU2(SEQ ID NO: 186; QVQLQESGPGLVKPSETLSLTCAVSGYSITSDYAWN-WIRQPPGKGLEWMGYINYSG NTDYNPSLK-SRSTISRDTSKNQFSLKLSSVTAADTAVYYCARGNFE-GAMDYWGQGT LVTVSS).

For use in designing 10D6-HU3-heavy, human antibody frameworks were analyzed by a BLAST search. The result revealed that the Herceptin backbone, which known to show very low immunogenicity of about 0.1% level among the pre-existing humanized antibodies, is very similar in framework and sequence to the mouse antibody 10D6. CDR-H1, CDR-H2, and CDR-H3 of the mouse antibody 10D6 were defined according to Kabat numbering and introduced into the Herceptin backbone, wherein back mutations were conducted at positions 27 (F-Y), 28 (N→S), 30 (K→T), 48 (V→M), 49 (A→G), 67 (F→S), 71 (A→R), 78 (A→F), and 93 (S→A), to establish 10D6-HU3 (SEQ ID NO: 187; EVQLVESGGGLVQPGGSLRLSCAASGYSITSDYAWN-WVRQAPGKGLEWMGYINYS GNTDYNPSLK-SRSTISRDTSKNTFYLQMNSLRAEDTAVYYCARGN-FEGAMDYWGQ GTLVTVSS).

2.12.2. Light Chain Humanization

To design a H1-light, human germline genes which share the highest identity/homology with the VL gene of the mouse antibody 10D6 were analyzed through an Ig BLAST (IgBLAST online database tool, maintained by National Center for Biotechnology Information (NCBI), Bethesda, Md.). The analysis results revealed IGKV1-39*01(012; accession number: X59315) has an identity/identity/homology of 66% at the amino acid level. CDR-L1(SEQ ID NO: 112), CDR-L2(SEQ ID NO: 113), and CDR-L3(SEQ ID NO: 114) of the mouse antibody 10D6 were defined according to Kabat numbering. A design was made to introduce the CDR of the mouse antibody 10D6 into the framework of IGKV1-39*01.

Thereafter, DNA fragments of heavy chains (10D6-VHHU1, 10D6-VHHU2, 10D6-VHHU3, and 10D6-VHHU5) were respectively cloned into a vector of pOptiVEC™-TOPO TA Cloning Kit enclosed in an OptiCHO™ Antibody Express Kit (Cat no. 12762-019, Invitrogen) using EcoRI (NEB, R0101S) and nheI (NEB, R0131), and a DNA fragment of a light chain (10D6-VLHU1 (SEQ ID NO: 165), coding sequence: SEQ ID NO: 177) was cloned into a vector of pcDNATM3.3-TOPO TA Cloning Kit using EcoRI (NEB, R0101S) and XhoI (NEB, R0146S), to construct recombinant vectors for expressing a humanized antibody.

The constructed vectors were amplified using a Qiagen Maxiprep kit (Cat No. 12662), and the vectors including the heavy chain and the vector including the light chain were added to 293T cells (2.5×10$^7$) at a ratio of about 4:1 (about 80 µg:20 µg) with 360 µl of 2 M $CaCl_2$ and were transfected. Next, the mixture was cultured in a DMEM medium with 10% (w/v) FBS at 37° C. in 5% (v/v) $CO_2$ conditions for 5 hours, and then cultured in a DMEM medium without FBS at 37° C. in 5% (v/v) $CO_2$ conditions for 48 hours.

The cultured cells were centrifuged, and 100 ml of each supernatant was purified using AKTA Prime (GE healthcare). Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was replaced with a PBS buffer, and thus final humanized antibodies 10D6-HU1, 10D6-HU2, 10D6-HU3, and 10D6-HU5 were purified.

2.13. Incorporation of the Selected CDRs into Humanized Antibody and Transformation to IgG The selected CDRs were incorporated into the heavy chain and the light chain of the humanized antibodies. Polynucleotides encoding the heavy chain of the antibodies were synthesized by Bioneer, Inc. so as to consist of 'EcoRI-signal sequence-VH-NheI-CH-XhoI' (SEQ ID NOs: 172-176). Polynucleotides encoding the light chain of the antibodies were synthesized by Bioneer, Inc. so as to consist of 'EcoRI-signal sequence-VL-BsiWI-CL-XhoI' (SEQ ID NOs: 177-179). The polynucleotides (SEQ ID NOs: 172-176) encoding the heavy chain were respectively cloned into a vector of pOptiVEC™-TOPO TA Cloning Kit included in OptiCHO™ Antibody Express Kit (Cat no. 12762-019;

Invitrogen), and the polynucleotides (SEQ ID NOs: 177-179) encoding the light chain were respectively cloned into a vector of pcDNA™3.3-TOPOTA Cloning Kit (Cat no. 8300-01), using EcoRI (NEB, R0101S) and XhoI (NEB, R0146S), to establish vectors for expressing affinity matured antibodies.

The constructed vectors were amplified using a Qiagen Maxiprep kit (Cat No. 12662), and the vectors including the heavy chain and the vector including the light chain were added to 293T cells ($2.5 \times 10^7$) at a ratio of about 4:1 (about 80 μg:20 μg) with 360 μl of 2 M $CaCl_2$ and were transfected. Next, the mixture was cultured in a DMEM medium with 10% (w/v) FBS at 37° C. in 5% (v/v) $CO_2$ conditions for 5 hours, and then cultured in a DMEM medium without FBS at 37° C. in 5% (v/v) $CO_2$ conditions for 48 hours.

The cultured cells were centrifuged, and 100 ml of each supernatant was purified using AKTA Prime (GE healthcare). Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was replaced with a PBS buffer, and thus final affinity-matured antibodies h10D6-Opti-1, h10D6-Opti-2, h10D6-Opti-3, and h10D6-Opti-4 were purified.

TABLE 16

| Clone | Antibody sequence (VH) | Antibody sequence (VL) |
|---|---|---|
| h10D6-OPTI-1 | >HU2-6.6:<br>QVQLQESGPGLVKPSETLSLTCA<br>VSGYSITSDYAWNWIRQPPGKG<br>LEWMGKISYSGKTDYNPSLKSR<br>STISRDTSKNQFSLKLSSVTAADT<br>AVYYCARGNFEGAMDYWGQG<br>TLVTVSS (SEQ ID NO: 160)<br>(Coding nucleotide sequence):<br>CAGGTGCAACTGCAGGAGTCA<br>GGCCCCGGCCTGGTAAAACCTT<br>CTGAAACGCTCTCACTTACCTG<br>TGCCGTTAGTGGATACTCTATC<br>ACTTCCGACTACGCTTGGAATT<br>GGATTCGGCAGCCTCCAGGCA<br>AAGGGCTGGAATGGATGGGAA<br>AGATTTCCTATTCCGGTAAGAC<br>TGACTACAATCCCAGTCTGAAG<br>AGCAGGTCAACAATCTCCAGA<br>GACACCAGCAAGAATCAGTTTT<br>CCCTGAAATTGTCCTCGGTGAC<br>AGCAGCGGATACCGCAGTGTA<br>TTATTGCGCCCGCGGTAACTTC<br>GAGGGAGCTATGGATTACTGG<br>GGGCAGGGTACTCTCGTCACTG<br>TGAGCAGC (SEQ ID NO: 172) | >HU1:<br>DIQMTQSPSSLSASVGDRVTITCK<br>ASQSVSNDVAWYQQKPGKAPKL<br>LIYYASNRYPGVPSRFSGSGSGTD<br>FTLTISSLQPEDFATYYCQQDYSSP<br>WTFGQGTKLEIK (SEQ ID NO: 165)<br>(Coding nucleotide sequence):<br>GACATCCAGATGACCCAGTCTCC<br>ATCCTCCCTGTCTGCATCTGTAG<br>GAGACAGAGTCACCATCACTTGC<br>AAGGCCAGTCAGAGTGTGAGTA<br>ATGATGTAGCTTGGTATCAGCAG<br>AAACCAGGGAAAGCCCCTAAGC<br>TCCTGATCTATTATGCATCCAAT<br>CGCTACCCTGGGGTCCCATCAAG<br>GTTCAGTGGCAGTGGATCTGGGA<br>CAGATTTCACTCTCACCATCAGC<br>AGTCTGCAACCTGAAGATTTTGC<br>AACTTACTACTGTCAGCAGGATT<br>ATAGCTCTCCGTGGACGTTCGGT<br>GGAGGCACCAAGGTGGAAATCA<br>AA (SEQ ID NO: 177) |
| h10D6-OPTI-2 | >HU2-6.7:<br>QVQLQESGPGLVKPSETLSLTCA<br>VSGYSITSDYAWNWIRQPPGKG<br>LEWMGKINYAGNTDYNPSLKS<br>RSTISRDTSKNQFSLKLSSVTAAD<br>TAVYYCARGNFEGAMDYWGQ<br>GTLVTVSS (SEQ ID NO: 161)<br>(Coding nucleotide sequence):<br>CAGGTGCAACTGCAGGAGTCA<br>GGCCCCGGCCTGGTAAAACCTT<br>CTGAAACGCTCTCACTTACCTG<br>TGCCGTTAGTGGATACTCTATC<br>ACTTCCGACTACGCTTGGAATT<br>GGATTCGGCAGCCTCCAGGCA<br>AAGGGCTGGAATGGATGGGAA<br>AGATTAACTATGCCGGTAACAC<br>TGACTACAATCCCAGTCTGAAG<br>AGCAGGTCAACAATCTCCAGA<br>GACACCAGCAAGAATCAGTTTT<br>CCCTGAAATTGTCCTCGGTGAC<br>AGCAGCGGATACCGCAGTGTA<br>TTATTGCGCCCGCGGTAACTTC<br>GAGGGAGCTATGGATTACTGG<br>GGGCAGGGTACTCTCGTCACTG<br>TGAGCAGC (SEQ ID NO: 173) | >HU1:<br>DIQMTQSPSSLSASVGDRVTITCK<br>ASQSVSNDVAWYQQKPGKAPKL<br>LIYYASNRYPGVPSRFSGSGSGTD<br>FTLTISSLQPEDFATYYCQQDYSSP<br>WTFGQGTKLEIK (SEQ ID NO: 165)<br>(Coding nucleotide sequence):<br>GACATCCAGATGACCCAGTCTCC<br>ATCCTCCCTGTCTGCATCTGTAG<br>GAGACAGAGTCACCATCACTTGC<br>AAGGCCAGTCAGAGTGTGAGTA<br>ATGATGTAGCTTGGTATCAGCAG<br>AAACCAGGGAAAGCCCCTAAGC<br>TCCTGATCTATTATGCATCCAAT<br>CGCTACCCTGGGGTCCCATCAAG<br>GTTCAGTGGCAGTGGATCTGGGA<br>CAGATTTCACTCTCACCATCAGC<br>AGTCTGCAACCTGAAGATTTTGC<br>AACTTACTACTGTCAGCAGGATT<br>ATAGCTCTCCGTGGACGTTCGGT<br>GGAGGCACCAAGGTGGAAATCA<br>AA (SEQ ID NO: 177) |
| h10D6-OPTI-43 | >HU2-6.6:<br>QVQLQESGPGLVKPSETLSLTCA<br>VSGYSITSDYAWNWIRQPPGKG<br>LEWMGKISYSGKTDYNPSLKSR<br>STISRDTSKNQFSLKLSSVTAADT<br>AVYYCARGNFEGAMDYWGQG<br>TLVTVSS (SEQ ID NO: 160)<br>(Coding nucleotide sequence):<br>CAGGTGCAACTGCAGGAGTCA<br>GGCCCCGGCCTGGTAAAACCTT | >HU1-6.11:<br>DIQMTQSPSSLSASVGDRVTITCK<br>ASQSVSNDVHWYQQKPGKAPKL<br>LIYYASNRYPGVPSRFSGSGSGTD<br>FTLTISSLQPEDFATYYCQQDYSSP<br>WTFGQGTKLEIK (SEQ ID NO: 166)<br>(Coding nucleotide sequence):<br>GACATCCAGATGACCCAGTCTCC<br>ATCCTCCCTGTCTGCATCTGTAG |

TABLE 16-continued

| Clone | Antibody sequence (VH) | Antibody sequence (VL) |
|---|---|---|
| | CTGAAACGCTCTCACTTACCTG<br>TGCCGTTAGTGGATACTCTATC<br>ACTTCCGACTACGCTTGGAATT<br>GGATTCGGCAGCCTCCAGGCA<br>AAGGGCTGGAATGGATGGGAA<br>AGATTTCCTATTCCGGTAAGAC<br>TGACTACAATCCCAGTCTGAAG<br>AGCAGGTCAACAATCTCCAGA<br>GACACCAGCAAGAATCAGTTTT<br>CCCTGAAATTGTCCTCGGTGAC<br>AGCAGCGGATACCGCAGTGTA<br>TTATTGCGCCCGCGGTAACTTC<br>GAGGGAGCTATGGATTACTGG<br>GGGCAGGGTACTCTCGTCACTG<br>TGAGCAGC (SEQ ID NO: 172) | GAGACAGAGTCACCATCACTTGC<br>AAGGCCAGTCAGAGTGTGAGTA<br>ATGATGTACATTGGTATCAGCAG<br>AAACCAGGGAAAGCCCCTAAGC<br>TCCTGATCTATTATGCATCCAAT<br>CGCTACCCTGGGGTCCCATCAAG<br>GTTCAGTGGCAGTGGATCTGGGA<br>CAGATTTCACTCTCACCATCAGC<br>AGTCTGCAACCTGAAGATTTTGC<br>AACTTACTACTGTCAGCAGGATT<br>ATAGCTCTCCGTGGACGTTCGGT<br>GGAGGCACCAAGGTGGAAATCA<br>AA (SEQ ID NO: 178) |
| h10D6-OPTI-55 | >HU2-6.7:<br>QVQLQESGPGLVKPSETLSLTCA<br>VSGYSITSDYAWNWIRQPPGKG<br>LEWMGKINYAGNTDYNPSLKS<br>RSTISRDTSKNQFSLKLSSVTAAD<br>TAVYYCARGNFEGAMDYWGQ<br>GTLVTVSS (SEQ ID NO: 161)<br>(Coding nucleotide sequence):<br>CAGGTGCAACTGCAGGAGTCA<br>GGCCCCGGCCTGGTAAAACCTT<br>CTGAAACGCTCTCACTTACCTG<br>TGCCGTTAGTGGATACTCTATC<br>ACTTCCGACTACGCTTGGAATT<br>GGATTCGGCAGCCTCCAGGCA<br>AAGGGCTGGAATGGATGGGAA<br>AGATTAACTATGCCGGTAACAC<br>TGACTACAATCCCAGTCTGAAG<br>AGCAGGTCAACAATCTCCAGA<br>GACACCAGCAAGAATCAGTTTT<br>CCCTGAAATTGTCCTCGGTGAC<br>AGCAGCGGATACCGCAGTGTA<br>TTATTGCGCCCGCGGTAACTTC<br>GAGGGAGCTATGGATTACTGG<br>GGGCAGGGTACTCTCGTCACTG<br>TGAGCAGC (SEQ ID NO: 173) | HU1-6.11:<br>DIQMTQSPSSLSASVGDRVTITCK<br>ASQSVSNDVHWYQQKPGKAPKL<br>LIYYASNRYPGVPSRFSGSGSGTD<br>FTLTISSLQPEDFATYYCQQDYSSP<br>WTFGQGTKLEIK (SEQ ID NO: 166)<br>(Coding nucleotide sequence):<br>GACATCCAGATGACCCAGTCTCC<br>ATCCTCCCTGTCTGCATCTGTAG<br>GAGACAGAGTCACCATCACTTGC<br>AAGGCCAGTCAGAGTGTGAGTA<br>ATGATGTACATTGGTATCAGCAG<br>AAACCAGGGAAAGCCCCTAAGC<br>TCCTGATCTATTATGCATCCAAT<br>CGCTACCCTGGGGTCCCATCAAG<br>GTTCAGTGGCAGTGGATCTGGGA<br>CAGATTTCACTCTCACCATCAGC<br>AGTCTGCAACCTGAAGATTTTGC<br>AACTTACTACTGTCAGCAGGATT<br>ATAGCTCTCCGTGGACGTTCGGT<br>GGAGGCACCAAGGTGGAAATCA<br>AA (SEQ ID NO: 178) |
| h10D6-OPTI-3 | >HU3-6.6:<br>EVQLVESGGGLVQPGGSLRLSC<br>AASGYSITSDYAWNWVRQAPG<br>KGLEWMGKISYSGKTDYNPSL<br>KSRSTISRDTSKNTFYLQMNSLR<br>AEDTAVYYCARGNFEGAMDY<br>WGQGTLVTVSS (SEQ ID NO: 162)<br>(Coding nucleotide sequence):<br>GAGGTTCAGCTGGTCGAAAGC<br>GGTGGGGGACTCGTGCAGCCA<br>GGCGGTTCTCTTAGATTATCAT<br>GTGCCGCATCCGGGTACTCCAT<br>CACCTCTGATTATGCATGGAAC<br>TGGGTCAGACAAGCCCCCGGA<br>AAGGGCCTGGAGTGGATGGGG<br>AAGATCTCCTATTCAGGGAAGA<br>CAGATTATAATCCTTCGCTGAA<br>AAGCAGATCAACAATTAGTAG<br>AGACACTTCTAAAAATACTTTT<br>TACCTCCAGATGAACAGTCTGC<br>GCGCCGAAGACACCGCCGTGT<br>ACTACTGCGCTAGGGGAAATTT<br>CGAGGGAGCTATGGACTATTG<br>GGGCCAGGGCACGTTGGTAAC<br>CGTGAGCAGC (SEQ ID NO: 174) | >HU1:<br>DIQMTQSPSSLSASVGDRVTITCK<br>ASQSVSNDVAWYQQKPGKAPKL<br>LIYYASNRYPGVPSRFSGSGSGTD<br>FTLTISSLQPEDFATYYCQQDYSSP<br>WTFGQGTKLEIK (SEQ ID NO: 165)<br>(Coding nucleotide sequence):<br>GACATCCAGATGACCCAGTCTCC<br>ATCCTCCCTGTCTGCATCTGTAG<br>GAGACAGAGTCACCATCACTTGC<br>AAGGCCAGTCAGAGTGTGAGTA<br>ATGATGTAGCTTGGTATCAGCAG<br>AAACCAGGGAAAGCCCCTAAGC<br>TCCTGATCTATTATGCATCCAAT<br>CGCTACCCTGGGGTCCCATCAAG<br>GTTCAGTGGCAGTGGATCTGGGA<br>CAGATTTCACTCTCACCATCAGC<br>AGTCTGCAACCTGAAGATTTTGC<br>AACTTACTACTGTCAGCAGGATT<br>ATAGCTCTCCGTGGACGTTCGGT<br>GGAGGCACCAAGGTGGAAATCA<br>AA (SEQ ID NO: 177) |
| h10D6-OPTI-4 | >HU3-6.7:<br>EVQLVESGGGLVQPGGSLRLSC<br>AASGYSITSDYAWNWVRQAPG<br>KGLEWMGKINYAGNTDYNPSL<br>KSRSTISRDTSKNTFYLQMNSLR<br>AEDTAVYYCARGNFEGAMDY<br>WGQGTLVTVSS (SEQ ID NO: 163)<br>(Coding nucleotide sequence):<br>GAGGTTCAACTGGTAGAGTCCG<br>GGGGCGGCCTGGTCCAGCCAG | >HU1:<br>DIQMTQSPSSLSASVGDRVTITCK<br>ASQSVSNDVAWYQQKPGKAPKL<br>LIYYASNRYPGVPSRFSGSGSGTD<br>FTLTISSLQPEDFATYYCQQDYSSP<br>WTFGQGTKLEIK (SEQ ID NO: 165)<br>(Coding nucleotide sequence):<br>GACATCCAGATGACCCAGTCTCC<br>ATCCTCCCTGTCTGCATCTGTAG |

TABLE 16-continued

| Clone | Antibody sequence (VH) | Antibody sequence (VL) |
|---|---|---|
| | GAGGAAGCCTGCGGCTCTCTTG<br>TGCCGCCAGCGGGTATAGTATC<br>ACTTCAGATTATGCCTGGAATT<br>GGGTCCGCCAGGCCCCCGGGA<br>AGGGCTTAGAGTGGATGGGTA<br>AAATTAATTACGCAGGCAACA<br>CCGACTATAATCCTTCACTGAA<br>ATCTAGATCCACCATCTCTAGA<br>GATACAAGTAAGAACACCTTTT<br>ACTTGCAGATGAATAGCCTCAG<br>GGCTGAAGACACTGCTGTGTAC<br>TACTGCGCAAGAGGAAACTTC<br>GAAGGAGCGATGGATTATTGG<br>GGCCAGGGTACGCTTGTGACA<br>GTGTCCTCT (SEQ ID NO: 175) | GAGACAGAGTCACCATCACTTGC<br>AAGGCCAGTCAGAGTGTGAGTA<br>ATGATGTAGCTTGGTATCAGCAG<br>AAACCAGGGAAAGCCCCTAAGC<br>TCCTGATCTATTATGCATCCAAT<br>CGCTACCCTGGGGTCCCATCAAG<br>GTTCAGTGGCAGTGGATCTGGGA<br>CAGATTTCACTCTCACCATCAGC<br>AGTCTGCAACCTGAAGATTTTGC<br>AACTTACTACTGTCAGCAGGATT<br>ATAGCTCTCCGTGGACGTTCGGT<br>GGAGGCACCAAGGTGGAAATCA<br>AA (SEQ ID NO: 177) |
| h10D6-OPTI-16 | >HU3-6.6:<br>EVQLVESGGGLVQPGGSLRLSC<br>AASGYSITSDYAWNWVRQAPG<br>KGLEWMGKISYSGKTDYNPSL<br>KSRSTISRDTSKNTFYLQMNSLR<br>AEDTAVYYCARGNFEGAMDY<br>WGQGTLVTVSS (SEQ ID NO: 162)<br>(Coding nucleotide sequence):<br>GAGGTTCAGCTGGTCGAAAGC<br>GGTGGGGGACTCGTGCAGCCA<br>GGCGGTTCTCTTAGATTATCAT<br>GTGCCGCATCCGGGTACTCCAT<br>CACCTCTGATTATGCATGGAAC<br>TGGGTCAGACAAGCCCCCGGA<br>AAGGGCCTGGAGTGGATGGGG<br>AAGATCTCCTATTCAGGGAAGA<br>CAGATTATAATCCTTCGCTGAA<br>AAGCAGATCAACAATTAGTAG<br>AGACACTTCTAAAAATACTTTT<br>TACCTCCAGATGAACAGTCTGC<br>GCGCCGAAGACACCGCCGTGT<br>ACTACTGCGCTAGGGGAAATTT<br>CGAGGGAGCTATGGACTATTG<br>GGGCCAGGGCACGTTGGTAAC<br>CGTGAGCAGC (SEQ ID NO: 174) | >HU1-6.11:<br>DIQMTQSPSSLSASVGDRVTITCK<br>ASQSVSNDVHWYQQKPGKAPKL<br>LIYYASNRYPGVPSRFSGSGSGTD<br>FTLTISSLQPEDFATYYCQQDYSSP<br>WTFGQGTKLEIK (SEQ ID NO: 166)<br>(Coding nucleotide sequence):<br>GACATCCAGATGACCCAGTCTCC<br>ATCCTCCCTGTCTGCATCTGTAG<br>GAGACAGAGTCACCATCACTTGC<br>AAGGCCAGTCAGAGTGTGAGTA<br>ATGATGTACATTGGTATCAGCAG<br>AAACCAGGGAAAGCCCCTAAGC<br>TCCTGATCTATTATGCATCCAAT<br>CGCTACCCTGGGGTCCCATCAAG<br>GTTCAGTGGCAGTGGATCTGGGA<br>CAGATTTCACTCTCACCATCAGC<br>AGTCTGCAACCTGAAGATTTTGC<br>AACTTACTACTGTCAGCAGGATT<br>ATAGCTCTCCGTGGACGTTCGGT<br>GGAGGCACCAAGGTGGAAATCA<br>AA (SEQ ID NO: 178) |
| h10D6-OPTI-17 | >HU3-6.7:<br>EVQLVESGGGLVQPGGSLRLSC<br>AASGYSITSDYAWNWVRQAPG<br>KGLEWMGKINYAGNTDYNPSL<br>KSRSTISRDTSKNTFYLQMNSLR<br>AEDTAVYYCARGNFEGAMDY<br>WGQGTLVTVSS (SEQ ID NO: 163)<br>GAGGTTCAACTGGTAGAGTCCG<br>GGGGCGGCCTGGTCCAGCCAG<br>GAGGAAGCCTGCGGCTCTCTTG<br>TGCCGCCAGCGGGTATAGTATC<br>ACTTCAGATTATGCCTGGAATT<br>GGGTCCGCCAGGCCCCCGGGA<br>AGGGCTTAGAGTGGATGGGTA<br>AAATTAATTACGCAGGCAACA<br>CCGACTATAATCCTTCACTGAA<br>ATCTAGATCCACCATCTCTAGA<br>GATACAAGTAAGAACACCTTTT<br>ACTTGCAGATGAATAGCCTCAG<br>GGCTGAAGACACTGCTGTGTAC<br>TACTGCGCAAGAGGAAACTTC<br>GAAGGAGCGATGGATTATTGG<br>GGCCAGGGTACGCTTGTGACA<br>GTGTCCTCT (SEQ ID NO: 175) | >HU1-6.11:<br>DIQMTQSPSSLSASVGDRVTITCK<br>ASQSVSNDVHWYQQKPGKAPKL<br>LIYYASNRYPGVPSRFSGSGSGTD<br>FTLTISSLQPEDFATYYCQQDYSSP<br>WTFGQGTKLEIK (SEQ ID NO: 166)<br>(Coding nucleotide sequence):<br>GACATCCAGATGACCCAGTCTCC<br>ATCCTCCCTGTCTGCATCTGTAG<br>GAGACAGAGTCACCATCACTTGC<br>AAGGCCAGTCAGAGTGTGAGTA<br>ATGATGTACATTGGTATCAGCAG<br>AAACCAGGGAAAGCCCCTAAGC<br>TCCTGATCTATTATGCATCCAAT<br>CGCTACCCTGGGGTCCCATCAAG<br>GTTCAGTGGCAGTGGATCTGGGA<br>CAGATTTCACTCTCACCATCAGC<br>AGTCTGCAACCTGAAGATTTTGC<br>AACTTACTACTGTCAGCAGGATT<br>ATAGCTCTCCGTGGACGTTCGGT<br>GGAGGCACCAAGGTGGAAATCA<br>AA (SEQ ID NO: 178) |
| h10D6-OPTI-42 | >HU5:<br>QVQLQESGPGLVKPSETLSLTCA<br>VSGYSITSDYAWNWIRQPPGKG<br>LEWIGYINYSGNTDYNPSLKSR<br>VTISVDTSKNQFSLKLSSVTAAD<br>TAVYYCARGNFEGAMDYWGQ<br>GTLVTVSS (SEQ ID NO: 164)<br>(Coding nucleotide sequence):<br>CAGGTGCAGCTGCAGGAGTCG<br>GGCCCAGGACTGGTGAAGCCTT<br>CGGAGACCCTGTCCCTCACCTG | >HU1-22:<br>DIQMTQSPSSLSASVGDRVTITCK<br>ASQSVSNDVHWYQQKPGKAPKL<br>LIYYASNRYPGVPSRFSGSGSGTD<br>FTLTISSLQPEDFATYYCQHDYSSP<br>FTFGQGTKLEIK (SEQ ID NO: 167)<br>(Coding nucleotide sequence):<br>GACATCCAGATGACCCAGTCTCC<br>ATCCTCCCTGTCTGCATCTGTAG<br>GAGACAGAGTCACCATCACTTGC |

TABLE 16-continued

| Clone | Antibody sequence (VH) | Antibody sequence (VL) |
|---|---|---|
| | CGCTGTCTCTGGTTACTCCATC | AAGGCCAGTCAGAGTGTGAGTA |
| | ACCAGTGATTATGCCTGGAACT | ATGATGTACATTGGTATCAGCAG |
| | GGATCCGGCAGCCCCCAGGGA | AAACCAGGGAAAGCCCCTAAGC |
| | AGGGGCTGGAGTGGATTGGGT | TCCTGATCTATTATGCATCCAAT |
| | ACATAAACTACAGTGGTAACA | CGCTACCCTGGGGTCCCATCAAG |
| | CTGACTACAACCCATCTCTCAA | GTTCAGTGGCAGTGGATCTGGGA |
| | AAGTCGAGTCACCATATCAGTA | CAGATTTCACTCTCACCATCAGC |
| | GACACGTCCAAGAACCAGTTCT | AGTCTGCAACCTGAAGATTTTGC |
| | CCCTGAAGCTGAGCTCTGTGAC | AACTTACTACTGTCAGCATGATT |
| | CGCCGCAGACACGGCCGTGTAT | ATAGCTCTCCGTTCACGTTCGGT |
| | TACTGTGCGAGAGGTAACTTCG | GGAGGCACCAAGGTGGAAATCA |
| | AAGGTGCTATGGACTACTGGG | AA (SEQ ID NO: 179) |
| | GTCAAGGAACGCTTGTGACAGT | |
| | GTCCTCT (SEQ ID NO: 176) | |

(In Table 16, the bold letters are CDR1, CDR2, and CDR3 in sequence)

2.14. Analysis of Binding Affinity of Selected Antibodies

The binding affinity (KD values) of the antibodies to human Ang2 protein was measured by an SPR method using a BIAcore T100 (GE Healthcare). 25 μg/ml anti-His antibody was immobilized on a CM5 sensor chip (GE healthcare) using a pH 5.0 acetate solution and an amine coupling kit (GE Healthcare). 6 μg/ml of a recombinant hAng2 (C-His, R&D Systems) protein was flowed onto the chip to be captured at 100 to 200 RU levels. The antibodies obtained in the above examples were diluted serially to twice each time starting from 100 nM concentration and it was each flowed onto the chip to allow it to be bound to (on), dissociated from (off), and regenerated (using 10 mM NaOH solution) from the antigen captured on the sensor chip, thereby to measure antigen-antibody affinity. The KD values were calculated from the values of $k_{on}$, $k_{off}$, and the results are as shown in the following Table 17.

TABLE 17

| Antibody | kon (1/Ms) | koff (1/s) | KD (nM) |
|---|---|---|---|
| m10D6 | $2.410 \times 10^4$ | $1.932 \times 10^{-4}$ | 8 |
| 10D6-HU1 | $3.082 \times 10^4$ | 0.002599 | 84 |
| 10D6-HU2 | $7.298 \times 10^4$ | 0.003464 | 47 |
| 10D6-HU3 | $4.503 \times 10^4$ | 0.001938 | 43 |
| 10D6-HU5 | $4.856 \times 10^4$ | 0.003115 | 64 |
| h10D6-OPTI-1 | $4.737 \times 10^5$ | $3.209 \times 10^{-4}$ | 0.68 |
| h10D6-OPTI-2 | $4.237 \times 10^5$ | $1.488 \times 10^{-4}$ | 0.34 |
| h10D6-OPTI-43 | $1.531 \times 10^6$ | $5.760 \times 10^{-4}$ | 0.38 |
| h10D6-OPTI-55 | $6.210 \times 10^5$ | $8.489 \times 10^{-5}$ | 0.14 |
| h10D6-OPTI-3 | $6.239 \times 10^5$ | $3.070 \times 10^{-4}$ | 0.49 |
| h10D6-OPTI-4 | $7.357 \times 10^5$ | $2.460 \times 10^{-4}$ | 0.33 |
| h10D6-OPTI-16 | $4.794 \times 10^5$ | $4.434 \times 10^{-4}$ | 0.92 |
| h10D6-OPTI-17 | $4.600 \times 10^5$ | $3.503 \times 10^{-4}$ | 0.76 |
| h10D6-OPTI-42 | $3.358 \times 10^5$ | $2.862 \times 10^{-4}$ | 0.85 |

As shown in Table 17, the affinity to Ang2 of the mouse antibody 10D6 is about 8 nM, the affinities to Ang2 of the 5 affinity-matured and humanized antibodies are from about 0.14 nM to about 0.92 nM. The results indicate that the affinity to Ang2 can be improved at least about 5 times up to about 37 times in the affinity-matured antibodies in an IgG form transformed from a scFv form.

2.15. Analysis of In Vitro Biological Property of the Selected Affinity-Matured Antibodies—Akt Phosphorylation To examine whether the humanized and/or affinity-matured 10D6 antibodies can induce activation of downstream signaling as well as Tie2 receptor, the levels of Akt phosphorylation in HUVEC (ATCC) cells treated with Ang2 and each of the antibodies (see Table 16) of Reference Example 2.13 were measured and compared to that of the case treated with Ang2 only. HUVEC (ATCC) cells (2×10⁴ cells) were cultured in 96 well plate using EGM-2 medium (Lonza) at 37° C., and when they reached 80~90% confluency, the media were replaced with serum-free medium (Lonza) and cultured at 37° C. for 6 hours. The cultured cells were treated with a mixture prepared by mixing 6 nM or 1.2 nM of each of the anti-Ang2 antibodies of Reference Example 2.13 with 4 nM of Ang2 protein (R&D systems) and letting them stand for 20 min. and further cultured for 30 min.

The phosphorylation of Akt which participates in downstream signaling of Tie2 receptor was examined using PathScan® Phospho-Akt Chemiluminescent Sandwich ELISA Kit (Cell signaling, #7134). The cells were washed using PBS, treated with 30 μl of a lysis buffer (Roche), to be subjected to cell lysis at 4° C. for 30 minutes. Then, 30 μl of diluent buffer (Cell Signaling) was added to each well and sufficiently mixed with pipet, and 50 ul of the diluted product was collected and transferred to a phosphor-Akt Ab coated microwell, to react at room temperature for 2 hours. After 2 hours, the well was washed with 1× washing buffer (Cell Signaling) four times, and treated with 50 μl of Akt1 detection antibody solution (Cell Signaling), to react at room temperature for one hour. As the same process, the well was washed, and reacted with 50 ul of HRP-conjugated secondary antibody (Cell Signaling) at room temperature for 30 minutes. As the same process, the well was washed, and treated with 50 ul of a mixture solution of luminol/enhancer solution (GE healthcare) and stable peroxide buffer (GE healthcare) at the ratio of 1:1 (v/v). Then the plate was placed in a luminometer (Envision 2104 plate reader, Perkin Elmer), to measure a relative light unit (RLU).

Figure 7A:
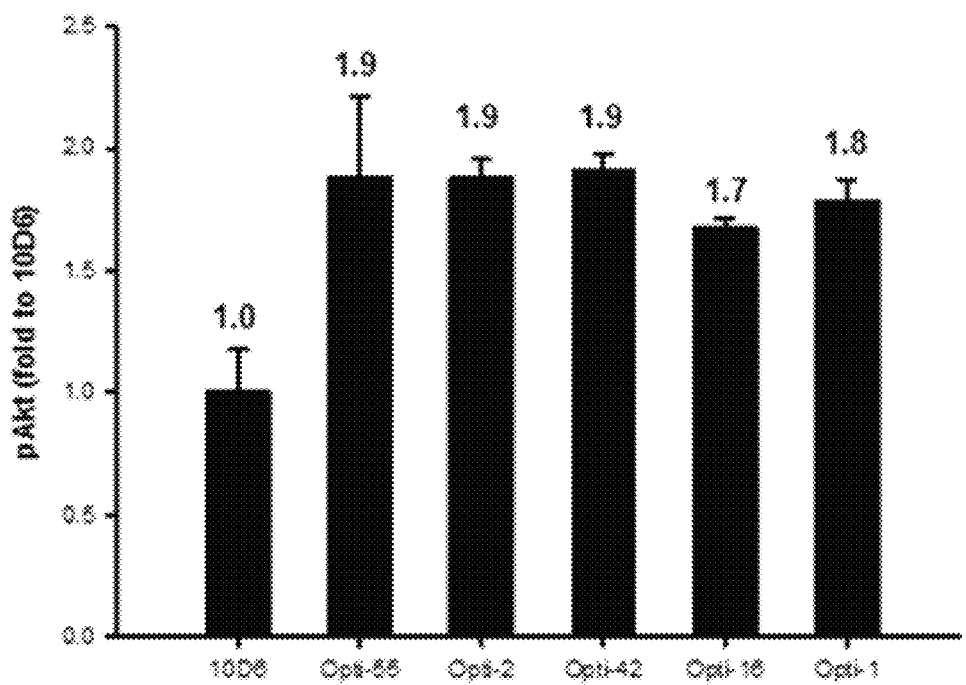
FIG. 7A is a graph showing the phosphorylation level of Akt protein relating to downstream signaling of Tie2 receptor by treatment of a humanized and affinity-matured anti-Ang2 antibody (6 nM) together with Ang2 (4 nM).
Figure 7B:
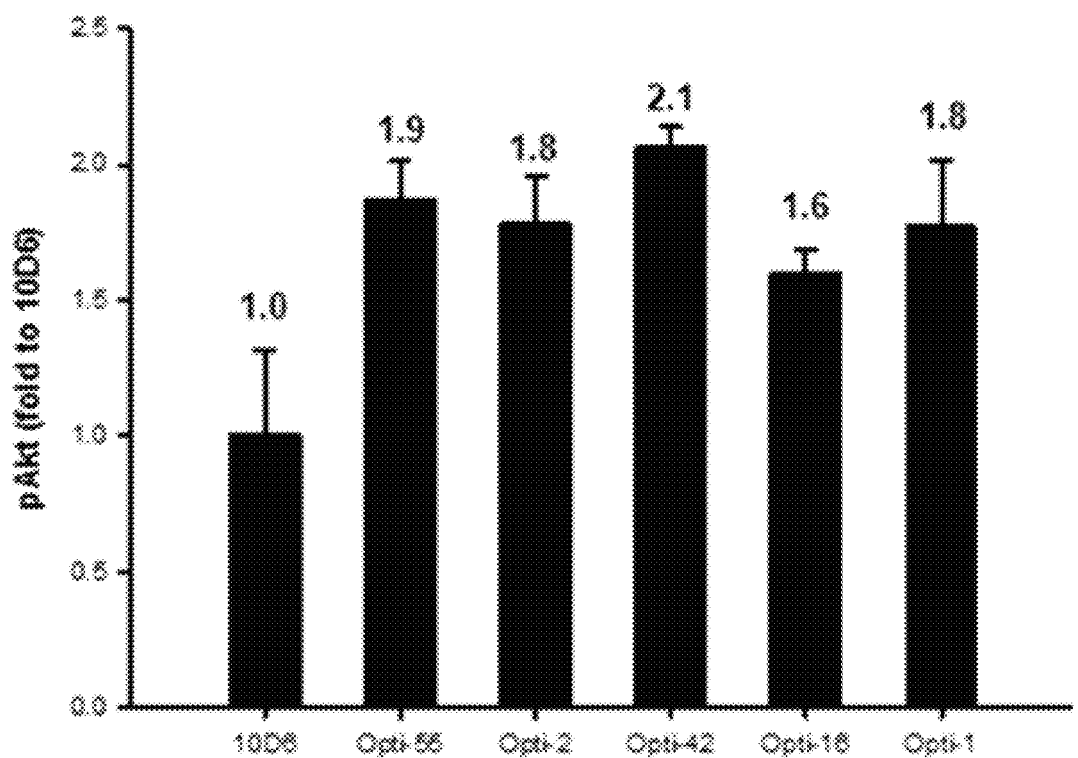
FIG. 7B is a graph showing the phosphorylation level of a protein (Akt) relating to downstream signaling of Tie2 receptor by treatment of a humanized and affinity-matured anti-Ang2 antibody (1.2 nM) together with Ang2 (4 nM).

The obtained results are shown in FIGS. 7A and 7B. As seen in FIGS. 7A and 7B, the humanized and/or affinity-matured antibodies of Reference Example 2.13 induce the downstream signaling more intensively compared to mouse antibody 10D6.

2.16. Synthesis of a Polynucleotide for Preparing an scFv of Humanized Antibody of 10D6 (Opti-1)

The gene for preparing scFv of a humanized 10D6 antibody was designed using the heavy chain variable region and the light chain variable region of humanized 10D6 antibody Opti-1. The heavy chain variable region (amino acid sequence: Hu2 6.6 (SEQ ID NO: 160); coding nucleotide sequence: SEQ ID NO: 172), and the light chain variable region (amino acid sequence: SEQ ID NO: Hu1 (SEQ ID NO: 165); coding nucleotide sequence: SEQ ID NO: SEQ ID NO: 177) were linked to form a 'VH-linker-VL' construct, and the linker was designed so as to have the amino acid sequence of 'GGGGSGGGGSGGGGS (SEQ ID NO: 184)'. The polynucleotide (SEQ ID NO: 191) encoding the designed scFv (VH-linker-VL; SEQ ID NO: 190) of antibody 10D6 opti-1 was synthesized by Bioneer, Inc.

2.17. Preparation of Gene Library for the Secondary Affinity Maturation 2.17.1. Selection of Target CDR and Preparation of Primers To perform affinity maturation of antibody 10D6 opti-1, three complementary determining regions (CDRs) were defined from the prepared antibody 10D6 opti-1 according to the 'Kabat numbering' rule. The CDRs are summarized in Table 18:

TABLE 18

| CDR | Amino acid sequence |
|---|---|
| CDR-L1 | KASQSVSNDVA (SEQ ID NO: 112) |
| CDR-L2 | YASNRYP (SEQ ID NO: 113) |
| CDR-L3 | QQDYSSPWT (SEQ ID NO: 6) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of 10D6 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

2.17.2. Construction of Gene Library of scFv of 10D6 Opti-1 Antibody

Figure 8:
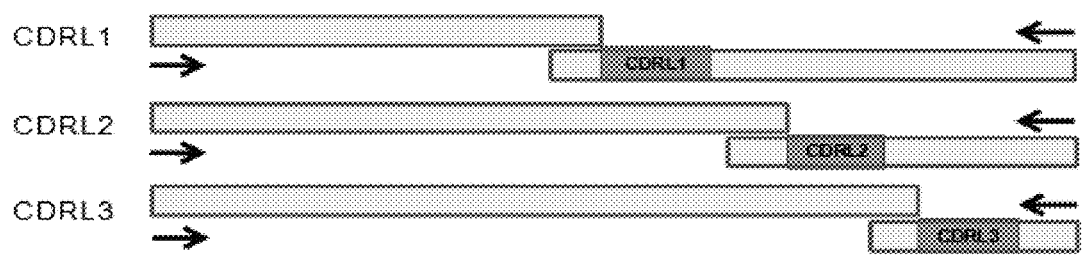
FIG. 8 schematically shows the process of overlap extension PCR for establishing scFv library genes of 10D6 antibody variants wherein a certain desired CDR is modified according to another embodiment.

The construction of antibody gene libraries through the introduction of random sequences was carried out using the primers synthesized in the same manner as in Reference Example 2.17.2. Two PCR products were obtained using a polynucleotide covering the 10D6 opti-1 scFv (SEQ ID NO: 191) as a template (see FIG. 8), and were subjected to overlap extension PCR to give scFv library genes for 10D6 antibodies in which only desired CDRs were mutated. $10^7$~$10^8$ libraries targeting each of the six CDRs prepared from the scFv library genes were constructed.

The affinity for Ang2 of each library was compared to that of the wild-type. Most libraries were lower in affinity for Ang2, compared to the wild-type. However, in some mutants, the affinity for Ang2 was retained.

2.18. Selection of Antibody with Improved Affinity from Libraries

Among the scFv libraries provided in Reference Example 2.17, the scFv fragments showing upper 1.0 percent (%) of affinity to Ang-2 were selected, and this process was repeated four times. The nucleotide sequence of each of the selected scFv was analyzed. The obtained nucleotide sequences are summarized in Table 19, and were converted into IgG forms (a heavy chain constant region: constant region of human IgG1, a light chain constant region: constant region of human KAPPA Chain). Four antibodies which were respectively produced from clones 10D6_VL-Hu1-2.1, 10D6_VL-Hu1-2.4, 10D6_VL-Hu1-2.7, 10D6_VL-Hu1-2.8 were used in the subsequent experiments.

TABLE 19

| Clone | Library constructed | CDR sequence |
|---|---|---|
| 10D6_VL-Hu1-2.1 | CDR-L1 | KASQFVSTDVH (SEQ ID NO: 125) |
| 10D6_VL-Hu1-2.4 | CDR-L2 | YASIPYP (SEQ ID NO: 126) |
| 10D6_VL-Hu1-2.7 | CDR-L1 + L2 | KASQSVSNDVH (SEQ ID NO: 124) + YASIPYP (SEQ ID NO: 126) |
| 10D6_VL-Hu1-2.8 | CDR-L1 + L2 | KASQFVSTDVH (SEQ ID NO: XX) + YASIPYP (SEQ ID NO: 126) |

2.19. Incorporation of the Selected CDRs into Humanized Antibody and Transformation to IgG The selected CDRs were incorporated into the heavy chain and the light chain of the humanized antibodies. The heavy chain was derived from the antibody cloned with Hu2-6.6 or Hu3-6.6. Polynucleotides encoding the light chain of the antibodies were synthesized by Bioneer, Inc. so as to consist of 'EcoRI-signal sequence-VL-BsiWI-CL-XhoI' (see Table 20). The polynucleotides encoding the heavy chain were respectively cloned into a vector of pOptiVEC™-TOPO TA Cloning Kit included in OptiCHO™ Antibody Express Kit (Cat no. 12762-019; Invitrogen), and the polynucleotides encoding the light chain were respectively cloned into a vector of pcDNA™3.3-TOPOTA Cloning Kit (Cat no. 8300-01), using EcoRI (NEB, R0101S) and XhoI (NEB, R0146S), to establish vectors for expressing affinity matured antibodies.

The constructed vectors were amplified using a Qiagen Maxiprep kit (Cat No. 12662), and the vectors including the heavy chain and the vector including the light chain were added to 293T cells ($2.5 \times 10^7$) at a ratio of about 4:1 (about 80 µg:20 µg) with 360 µl of 2 M $CaCl_2$ and were transfected. Next, the mixture was cultured in a DMEM medium with 10% (w/v) FBS at 37° C. in 5% (v/v) $CO_2$ conditions for 5 hours, and then cultured in a DMEM medium without FBS at 37° C. in 5% (v/v) $CO_2$ conditions for 48 hours.

The cultured cells were centrifuged, and 100 ml of each supernatant was purified using AKTA Prime (GE healthcare). Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was replaced with a PBS buffer, and thus final affinity-matured antibodies (hereinafter, named as h10D6-Opti-63, h10D6-Opti-65, h10D6-Opti-67, h10D6-Opti-71, h10D6-Opti-68, h10D6-Opti-70, h10D6-Opti-72, and h10D6-Opti-73) were purified.

TABLE 20

| Clone | Antibody sequence (VH) | Antibody sequence (VL) |
|---|---|---|
| h10D6-OPTI-63 | >HU2-6.6: QVQLQESGPGLVKPSETLSLTCAV SGYSISDYAWNWIRQPPGKGLE WMGKISYSGKTDYNPSLKSRSTIS | >10D6_VL-Hu1-2.1: DIQMTQSPSSLSASVGDRVTITCK ASQFVSTDVHWYQQKPGKAPKL LIYYASNRYPGVPSRFSGSGSGTD |

TABLE 20-continued

| Clone | Antibody sequence (VH) | Antibody sequence (VL) |
|---|---|---|
| | RDTSKNQFSLKLSSVTAADTAVYY<br>CARGNFEGAMDYWGQGTLVTVS<br>S (SEQ ID NO: 160)<br>(Coding nucleotide sequence):<br>CAGGTGCAACTGCAGGAGTCAGG<br>CCCCGGCCTGGTAAAACCTTCTG<br>AAACGCTCTCACTTACCTGTGCC<br>GTTAGTGGATACTCTATCACTTCC<br>GACTACGCTTGGAATTGGATTCG<br>GCAGCCTCCAGGCAAAGGGCTGG<br>AATGGATGGGAAAGATTTCCTAT<br>TCCGGTAAGACTGACTACAATCC<br>CAGTCTGAAGAGCAGGTCAACAA<br>TCTCCAGAGACACCAGCAAGAAT<br>CAGTTTTCCCTGAAATTGTCCTCG<br>GTGACAGCAGCGGATACCGCAGT<br>GTATTATTGCGCCCGCGGTAACT<br>TCGAGGGAGCTATGGATTACTGG<br>GGGCAGGGTACTCTCGTCACTGT<br>GAGCAGC (SEQ ID NO: 172) | FTLTISSLQPEDFATYYCQQDYSS<br>PWTFGQGTKLEIK (SEQ ID NO:<br>168)<br>(Coding nucleotide sequence):<br>GACATCCAGATGACCCAGTCTCC<br>ATCCTCCCTGTCTGCATCTGTAG<br>GAGACAGAGTCACCATCACTTG<br>CAAGGCCAGTCAGTTCGTGAGT<br>ACTGATGTACATTGGTATCAGCA<br>GAAACCAGGGAAAGCCCCTAAG<br>CTCCTGATCTATTATGCATCCAA<br>TCGCTACCCTGGGGTCCCATCAA<br>GGTTCAGTGGCAGTGGATCTGG<br>GACAGATTTCACTCTCACCATCA<br>GCAGTCTGCAACCTGAAGATTTT<br>GCAACTTACTACTGTCAGCAGGA<br>TTATAGCTCTCCGTGGACGTTCG<br>GTGGAGGCACCAAGGTGGAAAT<br>CAAA (SEQ ID NO: 180) |
| h10D6-OPTI-65 | >HU2-6.6:<br>QVQLQESGPGLVKPSETLSLTCAV<br>SGYSITSDYAWNWIRQPPGKGLE<br>WMGKISYSGKTDYNPSLKSRSTIS<br>RDTSKNQFSLKLSSVTAADTAVYY<br>CARGNFEGAMDYWGQGTLVTVS<br>S (SEQ ID NO: 160)<br>(Coding nucleotide sequence):<br>CAGGTGCAACTGCAGGAGTCAGG<br>CCCCGGCCTGGTAAAACCTTCTG<br>AAACGCTCTCACTTACCTGTGCC<br>GTTAGTGGATACTCTATCACTTCC<br>GACTACGCTTGGAATTGGATTCG<br>GCAGCCTCCAGGCAAAGGGCTGG<br>AATGGATGGGAAAGATTTCCTAT<br>TCCGGTAAGACTGACTACAATCC<br>CAGTCTGAAGAGCAGGTCAACAA<br>TCTCCAGAGACACCAGCAAGAAT<br>CAGTTTTCCCTGAAATTGTCCTCG<br>GTGACAGCAGCGGATACCGCAGT<br>GTATTATTGCGCCCGCGGTAACT<br>TCGAGGGAGCTATGGATTACTGG<br>GGGCAGGGTACTCTCGTCACTGT<br>GAGCAGC (SEQ ID NO: 172) | >10D6_VL-Hu1-2.4:<br>DIQMTQSPSSLSASVGDRVTITCK<br>ASQSVSNDVAWYQQKPGKAPKL<br>LIYYASIPYPGVPSRFSGSGSGTDF<br>TLTISSLQPEDFATYYCQQDYSSP<br>WTFGQGTKLEIK (SEQ ID NO: 169)<br>(Coding nucleotide sequence):<br>GACATCCAGATGACCCAGTCTCC<br>ATCCTCCCTGTCTGCATCTGTAG<br>GAGACAGAGTCACCATCACTTG<br>CAAGGCCAGTCAGAGTGTGAGT<br>AATGATGTAGCTTGGTATCAGCA<br>GAAACCAGGGAAAGCCCCTAAG<br>CTCCTGATCTATTATGCATCCAT<br>CCCATACCCTGGGGTCCCATCAA<br>GGTTCAGTGGCAGTGGATCTGG<br>GACAGATTTCACTCTCACCATCA<br>GCAGTCTGCAACCTGAAGATTTT<br>GCAACTTACTACTGTCAGCAGGA<br>TTATAGCTCTCCGTGGACGTTCG<br>GTGGAGGCACCAAGGTGGAAAT<br>CAAA (SEQ ID NO: 181) |
| h10D6-OPTI-67 | >HU2-6.6:<br>QVQLQESGPGLVKPSETLSLTCAV<br>SGYSITSDYAWNWIRQPPGKGLE<br>WMGKISYSGKTDYNPSLKSRSTIS<br>RDTSKNQFSLKLSSVTAADTAVYY<br>CARGNFEGAMDYWGQGTLVTVS<br>S (SEQ ID NO: 160)<br>(Coding nucleotide sequence):<br>CAGGTGCAACTGCAGGAGTCAGG<br>CCCCGGCCTGGTAAAACCTTCTG<br>AAACGCTCTCACTTACCTGTGCC<br>GTTAGTGGATACTCTATCACTTCC<br>GACTACGCTTGGAATTGGATTCG<br>GCAGCCTCCAGGCAAAGGGCTGG<br>AATGGATGGGAAAGATTTCCTAT<br>TCCGGTAAGACTGACTACAATCC<br>CAGTCTGAAGAGCAGGTCAACAA<br>TCTCCAGAGACACCAGCAAGAAT<br>CAGTTTTCCCTGAAATTGTCCTCG<br>GTGACAGCAGCGGATACCGCAGT<br>GTATTATTGCGCCCGCGGTAACT<br>TCGAGGGAGCTATGGATTACTGG<br>GGGCAGGGTACTCTCGTCACTGT<br>GAGCAGC (SEQ ID NO: 172) | >10D6_VL-Hu1-2.7:<br>DIQMTQSPSSLSASVGDRVTITCK<br>ASQSVSNDVHWYQQKPGKAPKL<br>LIYYASIPYPGVPSRFSGSGSGTDF<br>TLTISSLQPEDFATYYCQQDYSSP<br>WTFGQGTKLEIK (SEQ ID NO: 170)<br>(Coding nucleotide sequence):<br>GACATCCAGATGACCCAGTCTCC<br>ATCCTCCCTGTCTGCATCTGTAG<br>GAGACAGAGTCACCATCACTTG<br>CAAGGCCAGTCAGAGTGTGAGT<br>AATGATGTACATTGGTATCAGCA<br>GAAACCAGGGAAAGCCCCTAAG<br>CTCCTGATCTATTATGCATCCAT<br>CCCATACCCTGGGGTCCCATCAA<br>GGTTCAGTGGCAGTGGATCTGG<br>GACAGATTTCACTCTCACCATCA<br>GCAGTCTGCAACCTGAAGATTTT<br>GCAACTTACTACTGTCAGCAGGA<br>TTATAGCTCTCCGTGGACGTTCG<br>GTGGAGGCACCAAGGTGGAAAT<br>CAAA (SEQ ID NO: 182) |
| h10D6-OPTI-71 | >HU2-6.6:<br>QVQLQESGPGLVKPSETLSLTCAV<br>SGYSITSDYAWNWIRQPPGKGLE | 10D6_VL-Hu1-2.8:<br>DIQMTQSPSSLSASVGDRVTITCK<br>ASQFVSTDVHWYQQKPGKAPKL |

TABLE 20-continued

| Clone | Antibody sequence (VH) | Antibody sequence (VL) |
|---|---|---|
| | WMGKISYSGKTDYNPSLKSRSTIS<br>RDTSKNQFSLKLSSVTAADTAVYY<br>CARGNFEGAMDYWGQGTLVTVS<br>S (SEQ ID NO: 160)<br>(Coding nucleotide sequence):<br>CAGGTGCAACTGCAGGAGTCAGG<br>CCCCGGCCTGGTAAAACCTTCTG<br>AAACGCTCTCACTTACCTGTGCC<br>GTTAGTGGATACTCTATCACTTCC<br>GACTACGCTTGGAATTGGATTCG<br>GCAGCCTCCAGGCAAAGGGCTGG<br>AATGGATGGGAAAGATTTCCTAT<br>TCCGGTAAGACTGACTACAATCC<br>CAGTCTGAAGAGCAGGTCAACAA<br>TCTCCAGAGACACCAAGAAGAAT<br>CAGTTTTCCCTGAAATTGTCCTCG<br>GTGACAGCAGCGGATACCGCAGT<br>GTATTATTGCGCCCGCGGTAACT<br>TCGAGGGAGCTATGGATTACTGG<br>GGGCAGGGTACTCTCGTCACTGT<br>GAGCAGC (SEQ ID NO: 172) | LIYYASIPYPGVPSRFSGSGSGTDF<br>TLTISSLQPEDFATYYCQQDYSSP<br>WTFGQGTKLEIK (SEQ ID NO: 171)<br>(Coding nucleotide sequence):<br>GACATCCAGATGACCCAGTCTCC<br>ATCCTCCCTGTCTGCATCTGTAG<br>GAGACAGAGTCACCATCACTTG<br>CAAGGCCAGTCAGTTCGTGAGT<br>ACTGATGTACATTGGTATCAGCA<br>GAAACCAGGGAAAGCCCCTAAG<br>CTCCTGATCTATTATGCATCCAT<br>CCCATACCCTGGGGTCCCATCAA<br>GGTTCAGTGGCAGTGGATCTGG<br>GACAGATTTCACTCTCACCATCA<br>GCAGTCTGCAACCTGAAGATTTT<br>GCAACTTACTACTGTCAGCAGGA<br>TTATAGCTCTCCGTGGACGTTCG<br>GTGGAGGCACCAAGGTGGAAAT<br>CAAA (SEQ ID NO: 183) |
| h10D6-OPTI-68 | >HU3-6.6:<br>EVQLVESGGGLVQPGGSLRLSCAA<br>SGYSITSDYAWNWVRQAPGKGLE<br>WMGKISYSGKTDYNPSLKSRSTIS<br>RDTSKNTFYLQMNSLRAEDTAVY<br>YCARGNFEGAMDYWGQGTLVTV<br>SS (SEQ ID NO: 162)<br>(Coding nucleotide sequence):<br>GAGGTTCAGCTGGTCGAAAGCGG<br>TGGGGGACTCGTGCAGCCAGGCG<br>GTTCTCTTAGATTATCATGTGCCG<br>CATCCGGGTACTCCATCACCTCT<br>GATTATGCATGGAACTGGGTCAG<br>ACAAGCCCCCGGAAAGGGCCTG<br>GAGTGGATGGGAAGATCTCCTA<br>TTCAGGGAAGACAGATTATAATC<br>CTTCGCTGAAAAGCAGATCAACA<br>ATTAGTAGAGACACTTCTAAAAA<br>TACTTTTTACCTCCAGATGAACA<br>GTCTGCGCGCCGAAGACACCGCC<br>GTGTACTACTGCGCTAGGGGAAA<br>TTTCGAGGGAGCTATGGACTATT<br>GGGGCCAGGGCACGTTGGTAACC<br>GTGAGCAGC (SEQ ID NO: 174) | >10D6_VL-Hu1-2.1:<br>DIQMTQSPSSLSASVGDRVTITCK<br>ASQFVSTDVHWYQQKPGKAPKL<br>LIYYASNRYPGVPSRFSGSGSGTD<br>FTLTISSLQPEDFATYYCQQDYSS<br>PWTFGQGTKLEIK (SEQ ID NO: 168)<br>(Coding nucleotide sequence):<br>GACATCCAGATGACCCAGTCTCC<br>ATCCTCCCTGTCTGCATCTGTAG<br>GAGACAGAGTCACCATCACTTG<br>CAAGGCCAGTCAGTTCGTGAGT<br>ACTGATGTACATTGGTATCAGCA<br>GAAACCAGGGAAAGCCCCTAAG<br>CTCCTGATCTATTATGCATCCAA<br>TCGCTACCCTGGGGTCCCATCAA<br>GGTTCAGTGGCAGTGGATCTGG<br>GACAGATTTCACTCTCACCATCA<br>GCAGTCTGCAACCTGAAGATTTT<br>GCAACTTACTACTGTCAGCAGGA<br>TTATAGCTCTCCGTGGACGTTCG<br>GTGGAGGCACCAAGGTGGAAAT<br>CAAA (SEQ ID NO: 180) |
| h10D6-OPTI-70 | >HU3-6.6:<br>EVQLVESGGGLVQPGGSLRLSCAA<br>SGYSITSDYAWNWVRQAPGKGLE<br>WMGKISYSGKTDYNPSLKSRSTIS<br>RDTSKNTFYLQMNSLRAEDTAVY<br>YCARGNFEGAMDYWGQGTLVTV<br>SS (SEQ ID NO: 162)<br>(Coding nucleotide sequence):<br>GAGGTTCAGCTGGTCGAAAGCGG<br>TGGGGGACTCGTGCAGCCAGGCG<br>GTTCTCTTAGATTATCATGTGCCG<br>CATCCGGGTACTCCATCACCTCT<br>GATTATGCATGGAACTGGGTCAG<br>ACAAGCCCCCGGAAAGGGCCTG<br>GAGTGGATGGGAAGATCTCCTA<br>TTCAGGGAAGACAGATTATAATC<br>CTTCGCTGAAAAGCAGATCAACA<br>ATTAGTAGAGACACTTCTAAAAA<br>TACTTTTTACCTCCAGATGAACA<br>GTCTGCGCGCCGAAGACACCGCC<br>GTGTACTACTGCGCTAGGGGAAA<br>TTTCGAGGGAGCTATGGACTATT<br>GGGGCCAGGGCACGTTGGTAACC<br>GTGAGCAGC (SEQ ID NO: 174) | >10D6_VL-Hu1-2.4:<br>DIQMTQSPSSLSASVGDRVTITCK<br>ASQSVSNDVAWYQQKPGKAPKL<br>LIYYASIPYPGVPSRFSGSGSGTDF<br>TLTISSLQPEDFATYYCQQDYSSP<br>WTFGQGTKLEIK (SEQ ID NO: 169)<br>(Coding nucleotide sequence):<br>GACATCCAGATGACCCAGTCTCC<br>ATCCTCCCTGTCTGCATCTGTAG<br>GAGACAGAGTCACCATCACTTG<br>CAAGGCCAGTCAGAGTGTGAGT<br>AATGATGTAGCTTGGTATCAGCA<br>GAAACCAGGGAAAGCCCCTAAG<br>CTCCTGATCTATTATGCATCCAT<br>CCCATACCCTGGGGTCCCATCAA<br>GGTTCAGTGGCAGTGGATCTGG<br>GACAGATTTCACTCTCACCATCA<br>GCAGTCTGCAACCTGAAGATTTT<br>GCAACTTACTACTGTCAGCAGGA<br>TTATAGCTCTCCGTGGACGTTCG<br>GTGGAGGCACCAAGGTGGAAAT<br>CAAA (SEQ ID NO: 181) |
| h10D6-OPTI-72 | >HU3-6.6:<br>EVQLVESGGGLVQPGGSLRLSCAA<br>SGYSITSDYAWNWVRQAPGKGLE | >10D6_VL-Hu1-2.7:<br>DIQMTQSPSSLSASVGDRVTITCK<br>ASQSVSNDVHWYQQKPGKAPKL |

TABLE 20-continued

| Clone | Antibody sequence (VH) | Antibody sequence (VL) |
|---|---|---|
| | WMGKISYSGKTDYNPSLKSRSTIS<br>RDTSKNTFYLQMNSLRAEDTAVY<br>YCARGNFEGAMDYWGQGTLVTV<br>SS (SEQ ID NO: 162)<br>(Coding nucleotide sequence):<br>GAGGTTCAGCTGGTCGAAAGCGG<br>TGGGGGACTCGTGCAGCCAGGCG<br>GTTCTCTTAGATTATCATGTGCCG<br>CATCCGGGTACTCCATCACCTCT<br>GATTATGCATGGAACTGGGTCAG<br>ACAAGCCCCCGGAAAGGGCCTG<br>GAGTGGATGGGGAAGATCCCTA<br>TTCAGGGAAGACAGATTATAATC<br>CTTCGCTGAAAAGCAGATCAACA<br>ATTAGTAGAGACACTTCTAAAAA<br>TACTTTTTACCTCCAGATGAACA<br>GTCTGCGCGCCGAAGACACCGCC<br>GTGTACTACTGCGCTAGGGGAAA<br>TTTCGAGGGAGCTATGGACTATT<br>GGGGCCAGGGCACGTTGGTAACC<br>GTGAGCAGC (SEQ ID NO: 174) | LIYYASIPYPGVPSRFSGSGSGTDF<br>TLTISSLQPEDFATYYCQQDYSSP<br>WTFGQGTKLEIK (SEQ ID NO: 170)<br>(Coding nucleotide sequence):<br>GACATCCAGATGACCCAGTCTCC<br>ATCCTCCCTGTCTGCATCTGTAG<br>GAGACAGAGTCACCATCACTTG<br>CAAGGCCAGTCAGAGTGTGAGT<br>AATGATGTACATTGGTATCAGCA<br>GAAACCAGGGAAAGCCCCTAAG<br>CTCCTGATCTATTATGCATCCAT<br>CCCATACCCTGGGGTCCCATCAA<br>GGTTCAGTGGCAGTGGATCTGG<br>GACAGATTTCACTCTCACCATCA<br>GCAGTCTGCAACCTGAAGATTTT<br>GCAACTTACTACTGTCAGCAGGA<br>TTATAGCTCTCCGTGGACGTTCG<br>GTGGAGGCACCAAGGTGGAAAT<br>CAAA (SEQ ID NO: 182) |
| h10D6-OPTI-73 | >HU3-6.6:<br>EVQLVESGGGLVQPGGSLRLSCAA<br>SGYSITSDYAWNWVRQAPGKGLE<br>WMGKISYSGKTDYNPSLKSRSTIS<br>RDTSKNTFYLQMNSLRAEDTAVY<br>YCARGNFEGAMDYWGQGTLVTV<br>SS (SEQ ID NO: 162)<br>(Coding nucleotide sequence):<br>GAGGTTCAGCTGGTCGAAAGCGG<br>TGGGGGACTCGTGCAGCCAGGCG<br>GTTCTCTTAGATTATCATGTGCCG<br>CATCCGGGTACTCCATCACCTCT<br>GATTATGCATGGAACTGGGTCAG<br>ACAAGCCCCCGGAAAGGGCCTG<br>GAGTGGATGGGGAAGATCCCTA<br>TTCAGGGAAGACAGATTATAATC<br>CTTCGCTGAAAAGCAGATCAACA<br>ATTAGTAGAGACACTTCTAAAAA<br>TACTTTTTACCTCCAGATGAACA<br>GTCTGCGCGCCGAAGACACCGCC<br>GTGTACTACTGCGCTAGGGGAAA<br>TTTCGAGGGAGCTATGGACTATT<br>GGGGCCAGGGCACGTTGGTAACC<br>GTGAGCAGC (SEQ ID NO: 174) | 10D6_VL-Hu1-2.8:<br>DIQMTQSPSSLSASVGDRVTITCK<br>ASQFVSTDVHWYQQKPGKAPKL<br>LIYYASIPYPGVPSRFSGSGSGTDF<br>TLTISSLQPEDFATYYCQQDYSSP<br>WTFGQGTKLEIK (SEQ ID NO: 171)<br>(Coding nucleotide sequence):<br>GACATCCAGATGACCCAGTCTCC<br>ATCCTCCCTGTCTGCATCTGTAG<br>GAGACAGAGTCACCATCACTTG<br>CAAGGCCAGTCAGTTCGTGAGT<br>ACTGATGTACATTGGTATCAGCA<br>GAAACCAGGGAAAGCCCCTAAG<br>CTCCTGATCTATTATGCATCCAT<br>CCCATACCCTGGGGTCCCATCAA<br>GGTTCAGTGGCAGTGGATCTGG<br>GACAGATTTCACTCTCACCATCA<br>GCAGTCTGCAACCTGAAGATTTT<br>GCAACTTACTACTGTCAGCAGGA<br>TTATAGCTCTCCGTGGACGTTCG<br>GTGGAGGCACCAAGGTGGAAAT<br>CAAA (SEQ ID NO: 183) |

(In Table 20, the bold letters are CDR1, CDR2, and CDR3 in sequence)

2.20. Analysis of Binding Affinity of Selected Antibodies

The binding affinity (KD values) of the antibodies to human Ang2 protein was measured by an SPR method using a BIAcore T100 (GE Healthcare). 25 μg/ml anti-His antibody was immobilized on a CM5 sensor chip (GE healthcare) using a pH 5.0 acetate solution and an amine coupling kit (GE Healthcare). 6 μg/ml of a recombinant hAng2 (C-His, R&D Systems) protein was flowed onto the chip to be captured at 100 to 200 RU levels. The antibodies obtained in the above examples were diluted serially to twice each time starting from 100 nM concentration and it was each flowed onto the chip to allow it to be bound to (on), dissociated from (off), and regenerated (using 10 mM NaOH solution) from the antigen captured on the sensor chip, thereby to measure antigen-antibody affinity. The KD values were calculated from the values of $k_{on}$, $k_{off}$, and the results are as shown in the following Table 21.

TABLE 21

| Antibody | kon (1/Ms) | koff (1/s) | KD (M) |
|---|---|---|---|
| h10D6-OPTI-63 | $2.676 \times 10^6$ | $7.421 \times 10^{-5}$ | $2.773 \times 10^{-11}$ |
| h10D6-OPTI-65 | $4.960 \times 16^5$ | $2.250 \times 10^{-5}$ | $4.536 \times 10^{-12}$ |
| h10D6-OPTI-67 | $2.080 \times 16^6$ | $2.684 \times 10^{-7}$ | $1.291 \times 10^{-13}$ |
| h10D6-OPTI-68 | $5.355 \times 10^5$ | $1.696 \times 10^{-4}$ | $3.168 \times 10^{-10}$ |
| h10D6-OPTI-70 | $2.650 \times 10^5$ | $1.159 \times 10^{-4}$ | $4.374 \times 10^{-10}$ |

As shown in Table 21, all the affinity-matured and humanized antibodies show high affinity to Ang2 from about 0.000129 nM to about 0.43 nM.

2.21. Analysis of In Vitro Biological Property of the Selected Affinity-Matured Antibodies—Akt Phosphorylation To examine whether the humanized and/or affinity-matured 10D6 antibodies can induce activation of downstream signaling as well as Tie2 receptor, the levels of Akt phosphorylation in HUVEC (ATCC) cells treated with Ang2 and each of the antibodies (see Table 20) of Reference Example 2.19 were measured and compared to that of the case treated with Ang2 only. HUVEC (ATCC) cells ($2 \times 10^4$ cells) were cultured in 96 well plate using EGM-2 medium (Lonza) at 37° C., and when they reached 80~90% confluency, the media were replaced with serum-free medium (Lonza) and cultured at 37° C. for 6 hours. The cultured cells were treated with a mixture prepared by mixing 6 nM or 1.2 nM of each of the anti-Ang2 antibodies of Example 13 with 4 nM of Ang2 protein (R&D systems) and letting them stand for 20 min. and further cultured for 30 min.

The phosphorylation of Akt which participates in downstream signaling of Tie2 receptor was examined using PathScan® Phospho-Akt Chemiluminescent Sandwich ELISA Kit (Cell signaling, #7134). The cells were washed using PBS, treated with 30 µl of a lysis buffer (Roche), to be subjected to cell lysis at 4° C. for 30 minutes. Then, 30 µl of diluent buffer (Cell signaling) was added to each well and sufficiently mixed with pipet, and 50 µl of the diluted product was collected and transferred to a phosphor-Akt Ab coated microwell, to react at room temperature for 2 hours. After 2 hours, the well was washed with 1× washing buffer (Cell signaling) four times, and treated with 50 µl of Akt1 detection antibody solution (Cell signaling), to react at room temperature for one hour. As the same process, the well was washed, and reacted with 50 µl of HRP-conjugated secondary antibody (Cell signaling) at room temperature for 30 minutes. As the same process, the well was washed, and treated with 50 µl of a mixture solution of luminol/enhancer solution (GE healthcare) and stable peroxide buffer (GE healthcare) at the ratio of 1:1 (v/v). Then the plate was placed in a luminometer (Envision 2104 plate reader, Perkin Elmer), to measure a relative light unit (RLU).

Figure 9:
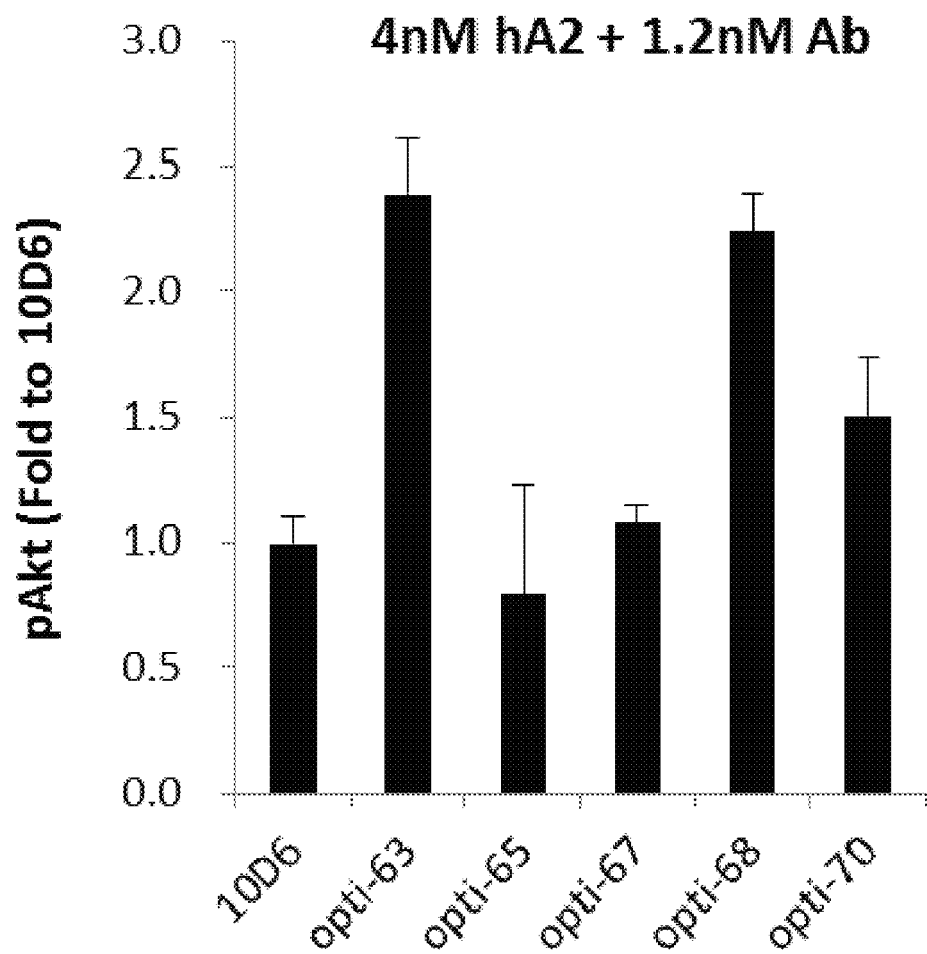
FIG. 9 is a graph showing the phosphorylation level of Akt relating to downstream signaling of Tie2 receptor by treatment of a humanized and affinity-matured anti-Ang2 antibody together with Ang2.

The obtained results are shown in FIG. 9. As seen in FIG. 9, the humanized and/or affinity-matured antibodies of Reference Example 2.19 induce the downstream signaling more intensively compared to mouse antibody 10D6.

Example 1: Preparation of an
Anti-c-Met/Anti-Ang2 Bispecific Antibody

The anti-Ang2 scFv [(heavy chain variable region (Amino acid sequence: Hu2 6.6 (SEQ ID NO: 160); Coding nucleotide sequence: SEQ ID NO: 172))-(linker: SEQ ID NO: 184)-(light chain variable region (Amino acid sequence: Hu1-1 (SEQ ID NO: 192; the 100$^{th}$ amino acid residue "Q" of Hu1 (SEQ ID NO: 165) is substituted with "G" (Q100G)); Coding nucleotide sequence: SEQ ID NO: SEQ ID NO: 193))] obtained on Reference Example 2.16 was fused to the C-terminus of Fc of the anti-c-Met antibody L3-1Y-IgG2 prepared in Reference Example 1, to prepare a bispecific antibody.

The heavy chain part of L3-1Y-IgG2 antibody which was used in the bispecific antibody cloning was prepared as follows. A DNA fragment encoding the heavy chain of the anti-c-Met antibody was synthesized by deleting the part encoding C-terminus part from position 1393 of SEQ ID NO: 67 and inserting "ggcggtggtggttccggaggcggcggatcc" instead of the deleted part (Bioneer Corporation). Thereafter, the DNA fragment was ligated to a vector from the pOp-tiVEC™-TOPO TA Cloning Kit included in OptiCHO™ Antibody Express Kit (Cat no. 12762-019) (Invitrogen).

An anti-Ang2 scFv was prepared by linking the heavy chain variable region (SEQ ID NO: 160) and the light chain variable region (SEQ ID NO: 192) of anti-Ang2 antibody via a peptide linker (GGGGS)$_2$. In particular, a nucleotide sequence (SEQ ID NO: 172) encoding the heavy chain variable region (SEQ ID NO: 160) of anti-Ang2 antibody, a nucleotide sequence (SEQ ID NO: 193) encoding the light chain variable region (SEQ ID NO: 192) of anti-Ang2 antibody, and a nucleotide sequence encoding the peptide linker were all synthesized by Bioneer Corporation (in the form including a N-terminal BamHI restriction site and C-terminal XhoI restriction site).

Then, the obtained anti-Ang2 scFv was cloned in the prepared L3-1Y-IgG2 containing vector using restriction enzymes BamHI and XhoI, to construct an expression vector for the heavy chain of the bispecific antibody.

Each region of the amino acid sequence (SEQ ID NO: 194; Coding nucleotide sequence: SEQ ID NO: 195) encoding the heavy chain of the bispecific antibody (wherein the heavy chain of the c-Met antibody and the anti-Ang2 scFv are linked through the peptide linker) is summarized in following Table 22:

TABLE 22

| SEQ ID NO: 194 N-terminus → C-terminus | |
|---|---|
| Signal peptide sequence | MEWSWVFLVTLLNGIQC |
| Heavy chain variable region of anti-c-Met antibody | EVQLVESGGGLVQPGGSLRLSCAASGFTFT<u>DYYMS</u>WVRQAPG KGLEWLG<u>FIRNKANGYTTEYSA</u>SVKGRFTISRDNSKNTLYLQM NSLRAEDTAVYYCAR<u>DNWFAY</u>WGQGTLVTVSS |
| Fc (IgG2) | ASTKGPSVFPLAPCSRSTSESTAALGCLVKDYFPEPVTVSWNSG ALTSGVHTFPAVLQSSGLYSLSSVVTVPSSNFGTQTYTCNVDHK PSNTKVDKTVERKCCVECPPCPAPPVAGPSVFLFPPKPKDTLMI SRTPEVTCVVVDVSHEDPEVQFNWYVDGVEVHNAKTKPREEQ FNSTFRVVSVLTVVHQDWLNGKEYKCKVSNKGLPAPIEKTISK TKGQPREPQVYTLPPSREEMTKNQVSLTCLVKGFYPSDIAVEW ESNGQPENNYKTTPPMLDSDGSFFLYSKLTVDKSRWQQGNVFS CSVMHEALHNHYTQKSLSLSPGK |
| Peptide linker (linking the C-terminus of Fc and the anti-Ang2 scFv) | GGGGSGGGGS |
| Heavy chain variable region of the anti-Ang2 scFv | QVQLQESGPGLVKPSETLSLTCAVSGYSIT<u>SDYAWN</u>WIRQPPGK GLEWMG<u>KISYSGKTDYNPSLKS</u>RSTISRDTSKNQFSLKLSSVTA ADTAVYYCAR<u>GNFEGAMDY</u>WGQGTLVTVSS |

TABLE 22-continued

SEQ ID NO: 194
N-terminus → C-terminus

| | |
|---|---|
| Peptide linker (linking the heavy chain variable region and the light chain variable region of the anti-Ang2 scFv) | GGGGSGGGGSGGGGS |
| Light chain variable region of the anti-Ang2 scFv | DIQMTQSPSSLSASVGDRVTITC<u>KASQSVSNDVA</u>WYQQKPGKA PKLLIY<u>YASNRYP</u>GVPSRFSGSGSGTDFTLTISSLQPEDFATYYC <u>QQDYSSPWT</u>FGGGTKLEIK<br>(Coding nucleotide sequence:<br>GACATCCAGATGACCCAGTCTCCATCCTCCCTGTCTGCATCT<br>GTAGGAGACAGAGTCACCATCACTTGCAAGGCCAGTCAGAG<br>TGTGAGTAATGATGTAGCTTGGTATCAGCAGAAACCAGGGA<br>AAGCCCCTAAGCTCCTGATCTATTATGCATCCAATCGCTACC<br>CTGGGGTCCCATCAAGGTTCAGTGGCAGTGGATCTGGGACA<br>GATTTCACTCTCACCATCAGCAGTCTGCAACCTGAAGATTTT<br>GCAACTTACTACTGTCAGCAGGATTATAGCTCTCCGTGGACG<br>TTCGGTGGAGGCACCAAGCTGGAAATCAAA (SEQ ID NO: 193) |

(CDRs are underlined)

In addition, the DNA fragment encoding the light chain of the anti-c-Met antibody was synthesized so that it has the nucleotide sequence of SEQ ID NO: 69 (Bioneer Corporation). The DNA fragment encoding the light chain of the anti-c-Met antibody was inserted into a vector from the pcDNA™3.3-TOPO TA Cloning Kit (Cat no. 8300-01) included in OptiCHO™ Antibody Express Kit (Cat no. 12762-019) (Invitrogen), to construct an expression vector for the light chain of the anti-c-Met antibody.

Each region of the amino acid sequence (SEQ ID NO: 68) encoding the light chain of the anti-c-Met antibody is summarized in following Table 23:

TABLE 23

SEQ ID NO: 68
N-terminus → C-terminus

| | |
|---|---|
| anti-c-Met antibody ª¹ heavy chain variable region | DIQMTQSPSSLSASVGDRVTITC<u>KSSQSLLASGNQNNYLA</u>WY QQKPGKAPKMLII<u>WASTRVS</u>GVPSRFSGSGSGTDFTLTISSLQ PEDFATYYC<u>QQSYSRPYT</u>FGQGTKVEIKRTVAAPSVFIFPPSD EQLKSGTASVVCLLNNFYPREAKVQWKVDNALQSGNSQESV TEQDSKDSTYSLSSTLTLSKADYEKHKVYACEVTHQGLSSPV TKSFNRGEC |

(CDRs are underlined)

Each of the constructed expression vectors for the heavy chain and the light chain was amplified using Qiagen Maxiprep kit (Cat no. 12662), and a temporary expression was performed using Freestyle™ MAX 293 Expression System (Invitrogen). For the expression, 293F cells were used and subjected to a suspension culture using Free-Style™ 293 Expression Medium. One day before the temporary expression, the cells were provided at the amount of 5×10⁵ cells/ml, and 24 hours after, when the number of the cells reaches 1×10⁶ cells/ml, the temporary expression was performed. A transfection was performed by liposomal reagent method using Freestyle™ MAX reagent (Invitrogen). In 15 ml tube, the DNA fragments encoding the heavy chain and the light chain were provided at the ratio of 1:1 (heavy chain DNA:light chain DNA), and mixed with 2 ml of OptiPro™ SFM (Invitrogen) (mixture (A)). In another 15 ml tube, 100 ml of Freestyle™ MAX reagent and 2 ml of OptiPro™ SFM 2 ml were mixed (mixture (B)). Then mixtures (A) and (B) were mixed and incubated for 15 minutes, and the obtained mixture was slowly added to and mixed with the cell provided one day before. After the transfection was completed, the cells were incubated for 4 days under the conditions of 37° C., 80% humidity, and 8% CO2 in 130 rpm incubator.

The incubated cells were centrifuged and 100 ml of each supernatant was collected and purified using AKTA Prime (GE Healthcare). AKTA Prime was equipped with HiTrap MabSelect SuRe column (GE Healthcare, 11-0034-95). The cell culture solution was flowed at the flow rate of 5 ml/min, and then, eluted with IgG elution buffer (Thermo Scientific, 21004), and the obtained eluate was exchanged with PBS buffer.

Finally, an antibody wherein the anti-Ang2 scFv is fused to the C-terminus of the anti-c-Met antibody L3-1Y-IgG2 was obtained and named as an anti-c-Met/anti-Ang2 bispecific antibody MA01.

Example 2: Binding Affinity of the Anti-c-Met/Anti-Ang2 Bispecific Antibody to c-Met The binding affinity of the anti-c-Met/anti-Ang2 bispecific antibody prepared in Example 1 to c-Met was measured using Biacore T100(GE). For this, a human Fab binder (#28-9583-25, GE Healthcare) was fixed on the surface of CM5 chip (#BR-1005-30, GE) according to manufacturer's manual. About 90~120 RU of the anti-c-Met/anti-Ang2 bispecific antibody was captured and then, c-Met-Fc (#358-MT/CF, R&D Systems) was added to the captured antibody at various concentrations. Hereto, 10 mM Glycine-HCl (pH 1.5) solution was added, to regenerate the surface. To measure the affinity, the above obtained data were fitted using BIAevaluation software (GE Healthcare, Biacore T100 evaluation software).

The obtained results are illustrated in Table 24:

TABLE 24

| $R_{max}$ (RU) | $K_D$ (nM) | $k_a$ (1/Ms) | $k_d$ (1/s) | Chi² | U-Value | T ($k_a$) | T ($k_d$) |
|---|---|---|---|---|---|---|---|
| 96.74 | 0.07 | $6.2 \times 10^6$ | $4.7 \times 10^{-5}$ | 1.46 | 12 | $1.9 \times 10^3$ | 69 |

As shown in Table 24, the bispecific antibody prepared in Example 1 shows the high affinity (about 0.07 nM) to c-Met, which is similar to that of an anti-c-Met antibody, L3-1Y/IgG2 prepared in Reference Example 1.

Example 3: Binding Affinity of the Anti-c-Met/Anti-Ang2 Bispecific Antibody to Ang2

The binding affinity of the anti-c-Met/anti-Ang2 bispecific antibody prepared in Example 1 to Ang2 was measured using Biacore T100(GE). For this, an anti-histidine antibody (R&D Systems) was fixed on the surface of CM5 chip (#BR-1005-30, GE) according to manufacturer's manual. C-terminal histidine-tagged human Ang2 (R&D Systems) was captured and then, anti-c-Met/anti-Ang2 bispecific antibody MA01 was added to the captured antigen (Ang2) at various concentrations. Hereto, 10 mM Glycine-HCl (pH 1.5) solution was added, to regenerate the surface. To measure the affinity, the above obtained data were fitted using BIAevaluation software (GE Healthcare, Biacore T100 evaluation software).

The obtained results are illustrated in Table 25:

TABLE 25

| ka (1/Ms) | kd (1/s) | $K_D$ (M) | Chi² (RU²) | U-value | T (ka) | T (kd) |
|---|---|---|---|---|---|---|
| $9.049 \times 10^4$ | 0.006481 | $7.162 \times 10^{-8}$ | 2.61 | 2 | 95 | $1.8 \times 10^2$ |

As shown in Table 25, the bispecific antibody prepared in Example 1 has binding affinity to Ang2 of about $7 \times 10^{-8}$ M.

Example 4: Cancer Cell Growth Inhibiting Effect of the Anti-c-Met/Anti-Ang2 Bispecific Antibody A cancer cell inhibiting effect of anti-c-Met/anti-Ang2 bispecific antibody MA01 prepared in Example 1 was examined for a gastric cancer cell line MKN45 and a lung cancer cell line EBC1.

5000 cells of MKN45 cell line (JCRB0254) and 5000 cells of EBC1 cell line (JCRB0820) were seeded in each well including RPMI medium (GIBCO; 100 µl/well), and treated with anti-c-Met/anti-Ang2 bispecific antibody MA01 at the amount of 60 nM (per 1 treatment) for 6 days. The change in the cell number was measured by CellTiter Glo (CTG) assay. In particular, after incubating for 6 days, 100 µl of CTG solution (Promega) was added to each well, and incubated at room temperature for 30 minutes. The obtained luminescent signal was recorded using Envision 2104 Multi-label Reader (Perkin Elmer, Waltham, Mass., USA).

For comparison, the same experiment was performed for groups treated with no antibody (None), anti-c-Met antibody L3-1Y/IgG2 alone (60 nM; Reference Example 1), anti-Ang2 antibody 10D6 alone (60 nM; Reference Example 2.3), anti-Ang2 antibody 4H10 alone (60 nM; Reference Example 2.4), a combination of L3-1Y/IgG2 and 10D6 (60 nM each), a combination of L3-1Y/IgG2 and 4H10 (60 nM each), and an bispecific antibody comprising L3-1Y/IgG2 and 4H10 scFv (BsAb; prepared referring to Example 1; 60 nM).

Figure 10:
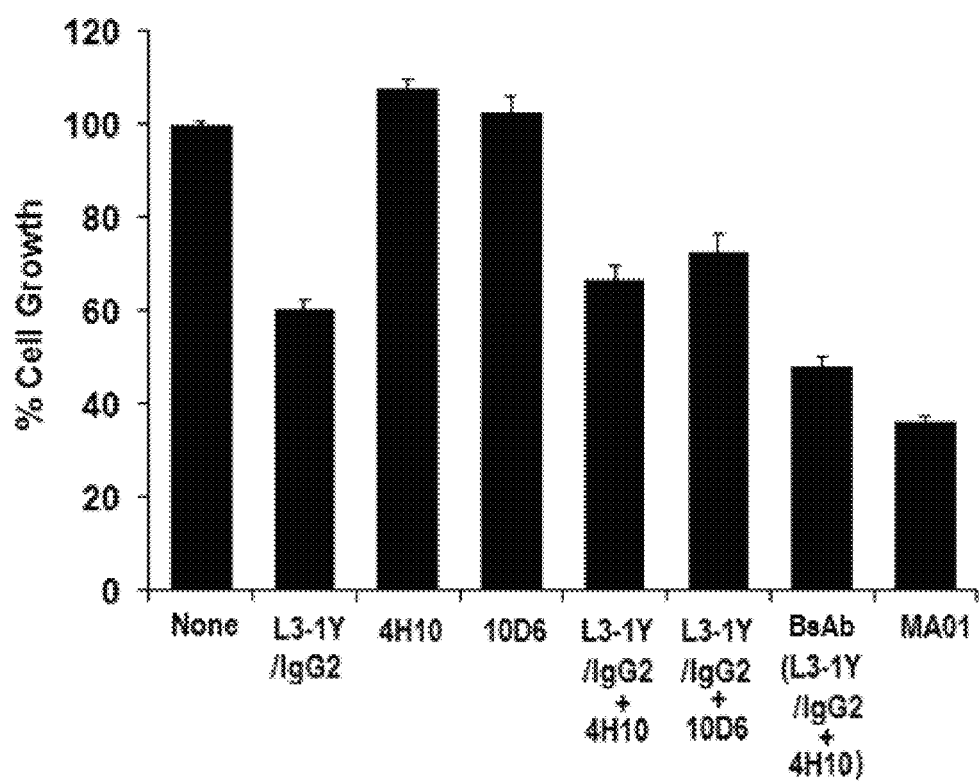
FIG. 10 is a graph showing the inhibition of cancer cell (MKN45) growth by treatment with an anti-c-Met/anti-Ang2 bispecific antibody.
Figure 11:
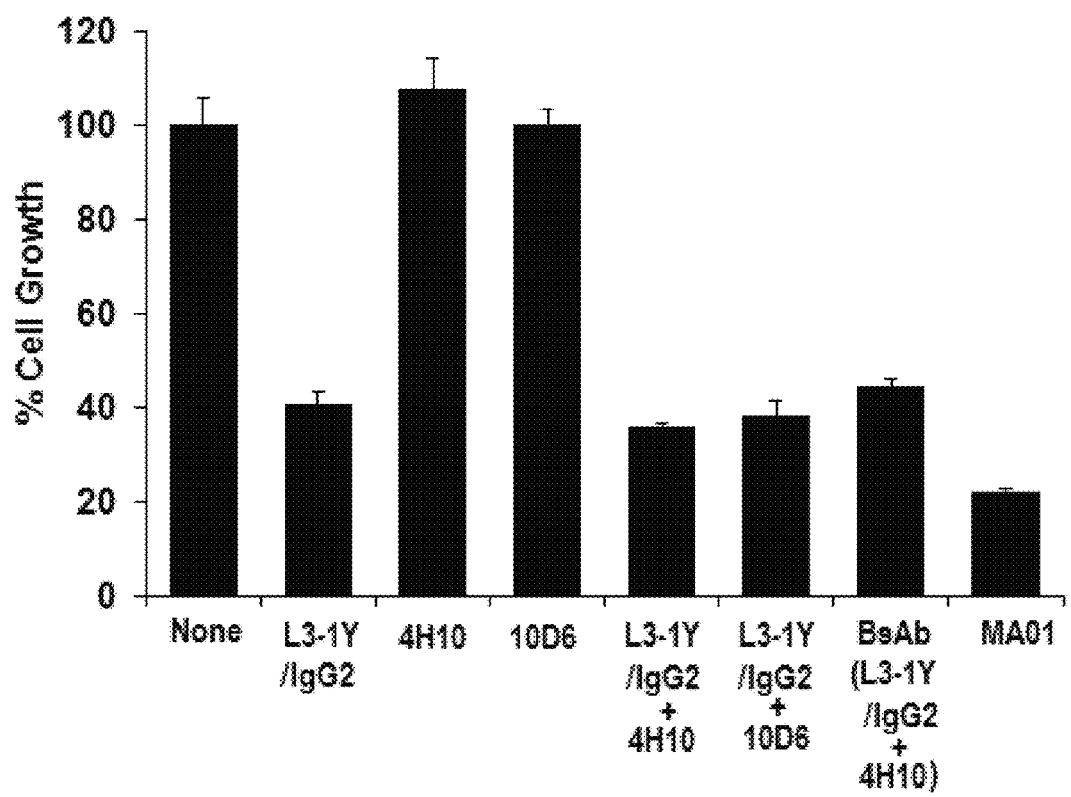
FIG. 11 is a graph showing the inhibition of cancer cell (EBC1) growth by treatment with an anti-c-Met/anti-Ang2 bispecific antibody.

The obtained results are shown in FIG. 10 (MKN45) and FIG. 11 (EBC1). As shown in FIGS. 10 and 11, anti-c-Met/anti-Ang2 bispecific antibody MA01 exhibits increased inhibition cancer cell growth, compared to the case wherein each or a combination of an anti-c-Met antibody and an anti-Ang2 antibody is administered.

To examine the inhibitory effect of anti-c-Met/anti-Ang2 bispecific antibody MA01 on the phosphorylation of signal transduction-related proteins, the Erk phosphorylation level was measured in cell lines MKN45 and EBC1 treated with anti-c-Met/anti-Ang2 bispecific antibody MA01. In particular, each of the cell lines MKN45 and EBC1 were seeded on 60 mm plate at the amount of $2 \times 10^5$ cells/ml, and 24 hours after, 5 µg/ml of anti-c-Met/anti-Ang2 bispecific antibody MA01 (serum-free) was administered to each cell line for 30 minutes. The Erk phosphorylation level by Erk kinase was measured by western blotting.

For comparison, the same experiment was performed for groups treated with no antibody (None), anti-c-Met antibody L3-1Y/IgG2 alone (5 µg/ml; Reference Example 1), anti-Ang2 antibody m10D6 alone (5 µg/ml; Reference Example 2.3), anti-Ang2 antibody 4H10 alone (5 µg/ml; Reference Example 2.4), a combination of L3-1Y/IgG2 and 10D6 (5 µg/ml each), a combination of L3-1Y/IgG2 and 4H10 (5 µg/ml each), and an bispecific antibody comprising L3-1Y/IgG2 and 4H10 scFv (BsAb; prepared referring to Example 1; 5 µg/ml).

Figure 12:
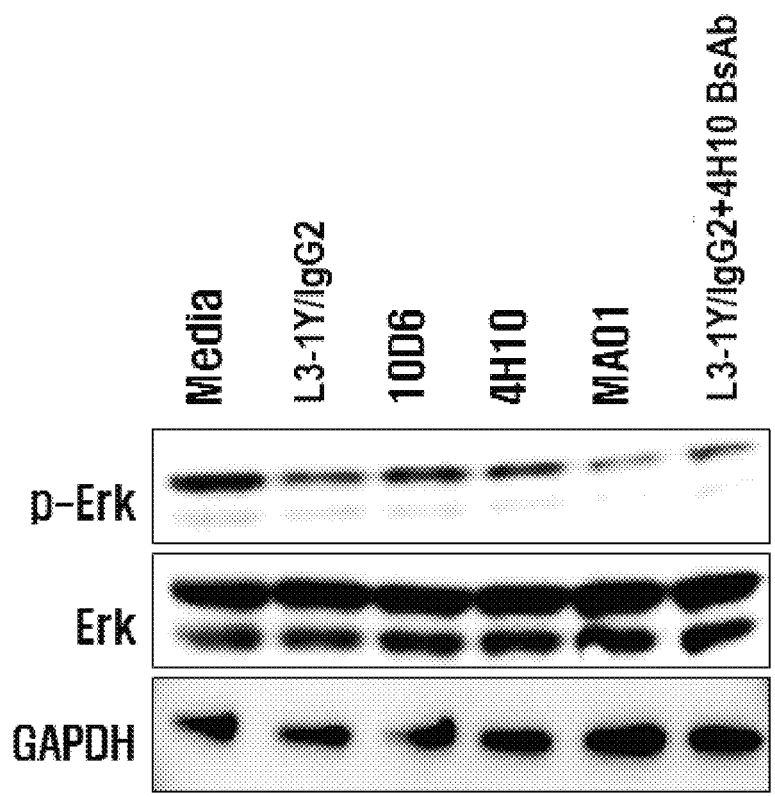
FIG. 12 provides results of immunoblotting showing the inhibition of cell growth signal in a gastric cancer cell line MKN45 by treatment with an anti-c-Met/anti-Ang2 bispecific antibody.
Figure 13:
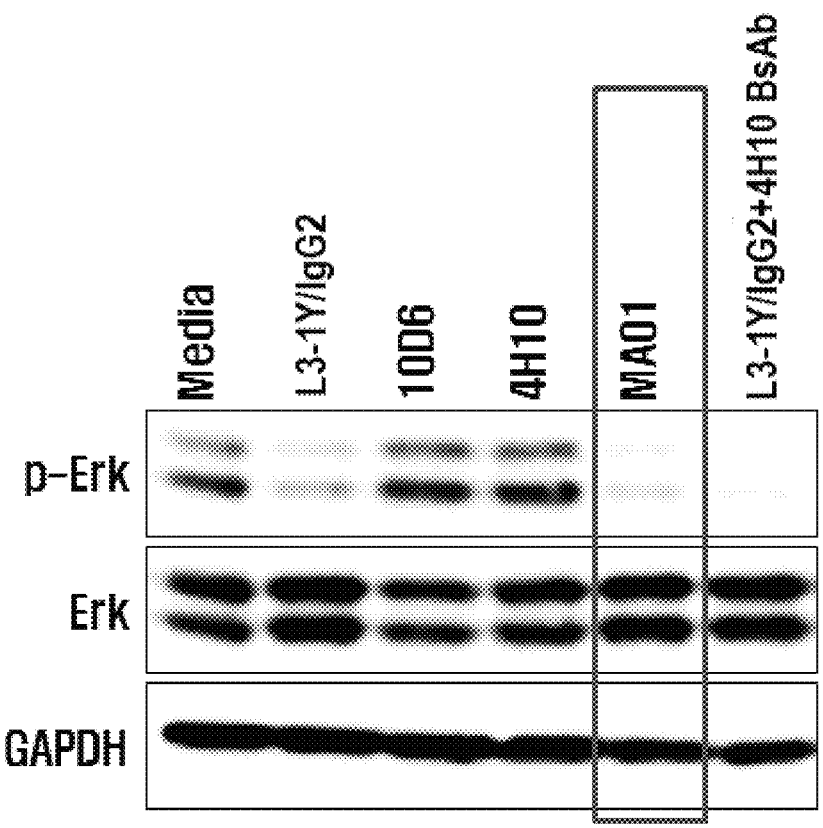
FIG. 13 provides results of immunoblotting showing the inhibition of cell growth signal in a lung cancer cell line EBC1 by treatment with an anti-c-Met/anti-Ang2 bispecific antibody.

The obtained results are shown in FIG. 12 (MKN45) and FIG. 13 (EBC1). As shown in FIGS. 12 and 13, anti-c-Met/anti-Ang2 bispecific antibody MA01 considerably inhibits the phosphorylation of Erk, compared to the case wherein each or a combination of an anti-c-Met antibody and an anti-Ang2 antibody is administered. Such inhibitory effect of MA01 on the phosphorylation of signal transduction related protein such as Erk may contribute to the cancer cell growth inhibitory effect.

Example 5: Apoptosis by the Anti-c-Met/Anti-Ang2 Bispecific Antibody

To confirm the anticancer effect of anti-c-Met/anti-Ang2 bispecific antibody MA01, the effect on apoptosis of cancer cells was examined.

The effect of anti-c-Met/anti-Ang2 bispecific antibody MA01 to kill cancer cells was examined for lung cancer cell line EBC1.

5000 cells of EBC1 cell line (JCRB0820) were seeded in each well including RPMI 1640 medium (GIBCO; 100 µl/well), and treated with anti-c-Met/anti-Ang2 bispecific antibody MA01 at the amount of 60 nM (per 1 treatment) for 6 days. The change in the cell number was measured by Caspase 3/7 Glo assay. In particular, after incubating for 6 days, 100 µl of Caspase 3/7 Glo solution (Promega) was added to each well, and incubated at room temperature for 30 minutes. The obtained luminescent signal was recorded using Envision 2104 Multi-label Reader (Perkin Elmer, Waltham, Mass., USA).

For comparison, the same experiment was performed for groups treated with no antibody (None), anti-c-Met antibody L3-1Y/IgG2 alone (60 nM; Reference Example 1), anti-Ang2 antibody 10D6 alone (60 nM; Reference Example 2.3), anti-Ang2 antibody 4H10 alone (60 nM; Reference Example 2.4), a combination of L3-1Y/IgG2 and 10D6 (60 nM each), a combination of L3-1Y/IgG2 and 4H10 (60 nM each), and an bispecific antibody comprising L3-1Y/IgG2 and 4H10 scFv (BsAb; prepared referring to Example 1; 60 nM).

Figure 14:
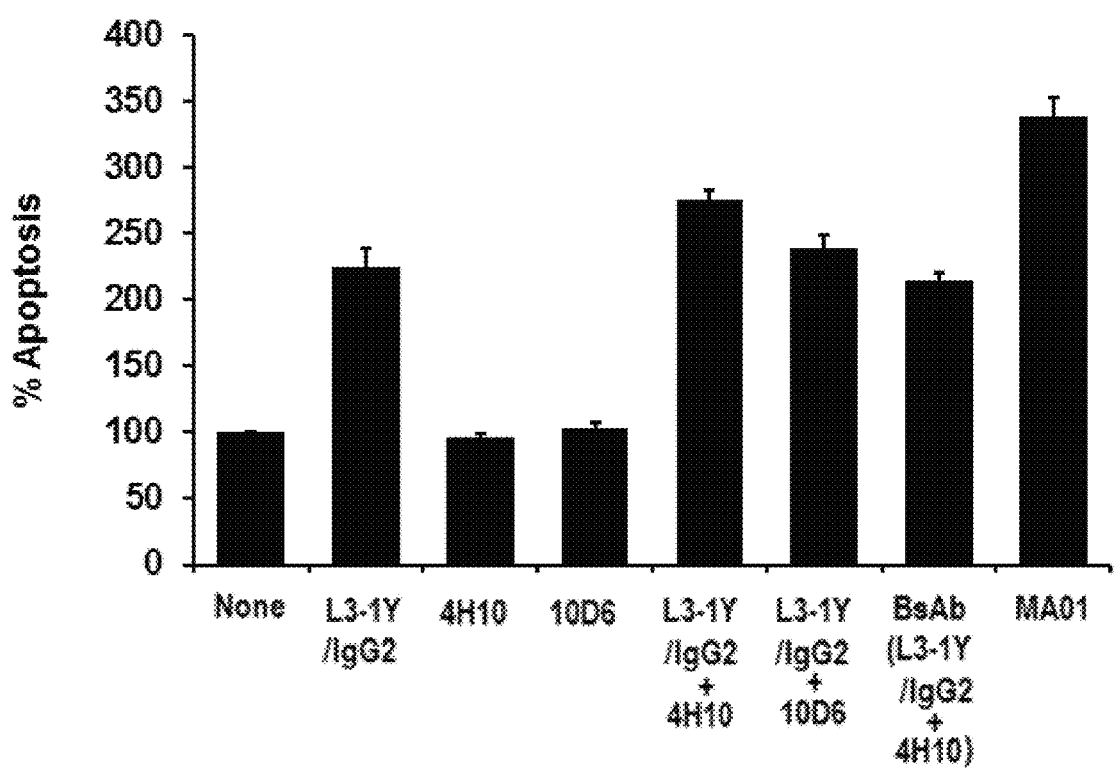
FIG. 14 is a graph showing the apoptosis effect of an anti-c-Met/anti-Ang2 bispecific antibody on a lung cancer cell line EBC1.

The obtained results are shown in FIG. 14. As shown in FIG. 14, anti-c-Met/anti-Ang2 bispecific antibody MA01 exhibits increased induction of apoptosis in cancer cells, compared to that of each or a combination of an anti-c-Met antibody and an anti-Ang2 antibody, or bispecific antibody of L3-1Y/IgG2 and 4H10.

Example 6: Cancer Cell Metastasis-Inhibiting Effect of the Anti-c-Met/Anti-Ang2 Bispecific Antibody Since Ang2 and c-Met are both related to cancer metastasis as well as cancer cell proliferation, the effect of the anti-c-Met/anti-Ang2 bispecific antibody MA01 prepared in Example 1 on cell motility was observed. The inhibition effect of the bispecific antibody on HUVEC(→EBC1) migration by Ang2+HGF was tested as follows:

A migration assay was performed using xCelligence-RTCA DP system (Roche), to confirm whether or not the motility of endothelial cells induced by HGF and Ang2 is inhibited. The xCelligence-RTCA DP system used is a non-invasive cell monitoring system capable of measuring impedance generated when a cell is attached on a gold microelectrode array in real-time thereby determining changes of cells. For the cell migration assay, CIM-plate16 (GE Healthcare) consisting of a lower chamber (having chemoattractant) and a upper chamber was used, to measure and record the impedance generated when a cell on the upper chamber moves to the lower chamber having chemoattractant passing through 8 µm pores and attaches to the bottom. As the chemoattractant, 100 ng/ml HGF (R&D systems) and 200 ng/ml Ang2, which are added to RPMI1640 medium supplemented with 10% FBS, was used. The anti-c-Met/anti-Ang2 bispecific antibody MA01 was added to the upper chamber at the concentration of 1 µg/ml. 10000 cells of lung cancer cell line EBC1 were seeded in each well. For comparison, the same experiment was performed for groups treated with no antibody (None), anti-c-Met antibody L3-1Y/IgG2 alone (1 µg/ml; Reference Example 1), and anti-Ang2 antibody 10D6 alone (1 µg/ml; Reference Example 2.3).

Figure 15:
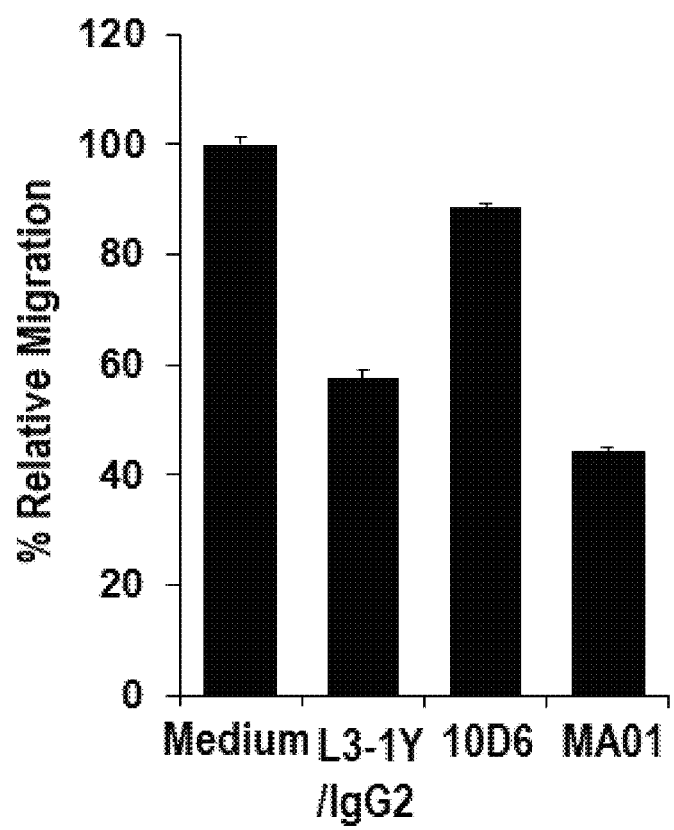
FIG. 15 is a graph showing the metastasis inhibition effect of an anti-c-Met/anti-Ang2 bispecific antibody on a lung cancer cell line EBC1.

The obtained results are illustrated in FIG. 15. As shown in FIG. 15, the anti-c-Met/anti-Ang2 bispecific antibody MA01 exhibits an inhibitory effect on EBC1 migration by Ang2+HGF wherein the inhibitory effect is considerably increased, compared with that of L3-1Y/IgG2 or 10D6 alone.

Example 7: Effect of the Anti-c-Met/Anti-Ang2 Bispecific Antibody to Overcome a Resistance to c-Met Targeting Drugs To confirm the possibility of anti-c-Met/anti-Ang2 bispecific antibody MA01 to overcome the resistance to c-Met targeting drugs, an ovarian cancer cell line SKOV3 (ATCC, HTB77) which is resistant to anti-c-Met antibody L3-1Y/IgG2 of Reference Example 1. Referring to the method described in Example 4, 5000 cells of SKOV3 were treated with anti-c-Met/anti-Ang2 bispecific antibody MA01 (60 nM), and 6 days after, the cell number was measured by CellTiter Glo assay.

For comparison, the same experiment was performed for groups treated with no antibody (None), anti-c-Met antibody L3-1Y/IgG2 alone (60 nM; Reference Example 1), anti-Ang2 antibody m10D6 alone (60 nM; Reference Example 2.3), and a combination of L3-1Y/IgG2 and 10D6 (60 nM each).

Figure 16:
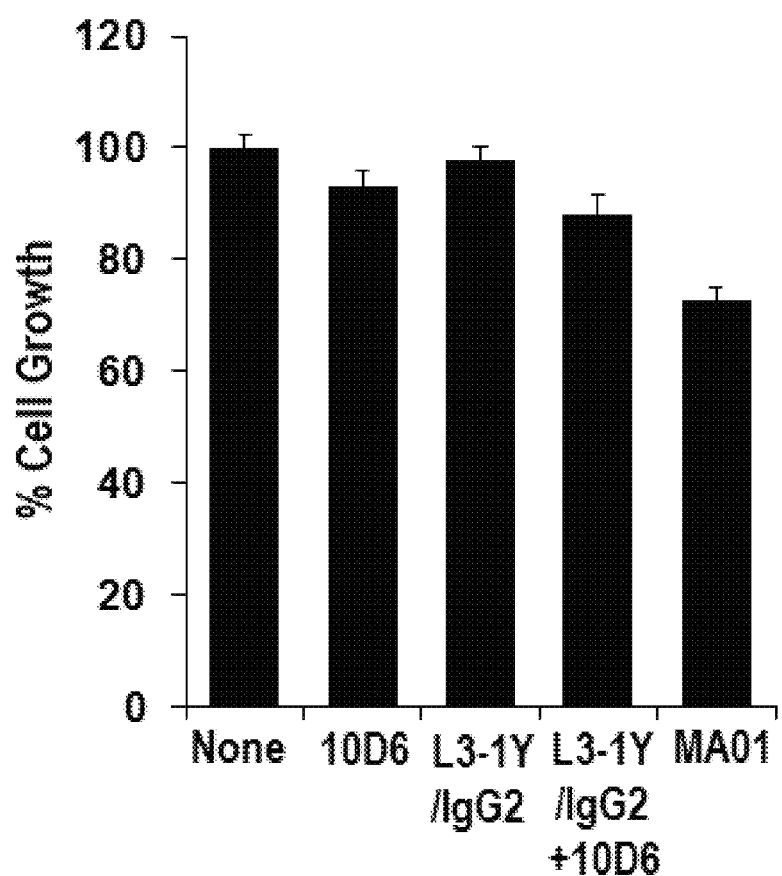
FIG. 16 is a graph showing the cell growth inhibition on a c-Met inhibitor-resistant cancer cell by treatment of an anti-c-Met/anti-Ang2 bispecific antibody.

The obtained results are shown in FIG. 16. As shown in FIG. 16, anti-c-Met/anti-Ang2 bispecific antibody MA01 has an excellent effect to overcome the resistance to c-Met targeting drugs, compared with that of L3-1Y-IgG2 and/or 10D6 alone.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-c-Met/anti-Ang2 bispecific antibody comprising (a) an anti-c-Met antibody or antigen-binding fragment thereof and (b) an anti-Ang2 antibody or antigen-binding fragment thereof, wherein the anti-c-Met antibody or antigen-binding fragment thereof comprises (i) a heavy chain variable region comprising (a) a CDR-H1 comprising SEQ ID NO: 1, 22, 23, or 24, (b) a CDR-H2 comprising SEQ ID NO: 2, 25, or 26, and (c) a CDR-H3 comprising SEQ ID NO: 3, 27, 28, or 85, and (ii) a light chain variable region comprising (a) a CDR-L1 comprising an SEQ ID NO: 10, 29, 30, 31, 32, 33 or 106, (b) a CDR-L2 comprising SEQ ID NO: 11, 34, 35, or 36, and (c) a CDR-L3 comprising SEQ ID NO: 12, 13, 14, 15, 16, 37, 86, or 89;

and the anti-Ang-2 antibody or antigen-binding fragment thereof comprises:

(i) a heavy chain variable region comprising (a) a CDR-H1 comprising SEQ ID NO: 109, (b) a CDR-H2 comprising SEQ ID NO: 128, and (c) a CDR-H3 comprising SEQ ID NO: 111, and (ii) a light chain variable region comprising a CDR-L1 comprising SEQ ID NO: 129, a CDR-L2 comprising SEQ ID NO: 130, and a CDR-L3 comprising SEQ ID NO: 131.

2. The anti-c-Met/anti-Ang2 bispecific antibody of claim 1, wherein the anti-Ang2 antibody or antigen-binding fragment thereof comprises:

a heavy chain variable region comprising a CDR-H1 comprising SEQ ID NO: 109, a CDR-H2 comprising SEQ ID NO: 110, and a CDR-H3 comprising SEQ ID NO: 111; and a light chain variable region comprising a CDR-L1 comprising SEQ ID NO: 112, a CDR-L2 comprising SEQ ID NO: 113, and a CDR-L3 comprising SEQ ID NO: 114.

3. The anti-c-Met/anti-Ang2 bispecific antibody of claim 2, wherein the anti-Ang2 antibody or antigen-binding fragment thereof comprises a heavy chain variable region comprising SEQ ID NO: 115 and a light chain variable region comprising SEQ ID NO: 117.

4. The anti-c-Met/anti-Ang2 bispecific antibody of claim 1, wherein the anti-Ang2 antibody or antigen-binding fragment thereof comprises:

a heavy chain variable region comprising a CDR-H1 comprising SEQ ID NO: 109, a CDR-H2 comprising SEQ ID NO: 128, and a CDR-H3 comprising SEQ ID NO: 111; and a light chain variable region comprising a CDR-L1 comprising SEQ ID NO: 129, a CDR-L2 comprising SEQ ID NO: 130, and a CDR-L3 comprising SEQ ID NO: 131, with the proviso that an anti-Ang2 antibody or an antigen-binding fragment thereof does not comprise a heavy chain variable region comprising a CDR-H1 of SEQ ID NO: 109, a CDR-H2 of SEQ ID NO: 110, and a CDR-H3 of SEQ ID NO: 111, and a light chain variable region comprising a CDR-L1 of SEQ ID NO: 112, a CDR-L2 of SEQ ID NO: 113, and a CDR-L3 of SEQ ID NO: 114.

5. The anti-c-Met/anti-Ang2 bispecific antibody of claim 4, wherein the anti-Ang2 antibody or antigen-binding fragment thereof comprises:

a heavy chain variable region comprising a CDR-H1 comprising SEQ ID NO: 109, a CDR-H2 comprising SEQ ID NO: 122 or 123, and a CDR-H3 comprising SEQ ID NO: 111; and a light chain variable region comprising a CDR-L1 comprising SEQ ID NO: 112, 124, or 125, a CDR-L2 comprising SEQ ID NO: 113 or 126, and a CDR-L3 comprising SEQ ID NO: 114 or 127, with the proviso that an anti-Ang2 antibody or an antigen-binding fragment thereof does not comprise a heavy chain variable region comprising a CDR-H1 of SEQ ID NO: 109, a CDR-H2 of SEQ ID NO: 110, and a CDR-H3 of SEQ ID NO: 111, and a light chain variable region comprising a CDR-L1 of SEQ ID NO: 112, a CDR-L2 of SEQ ID NO: 113, and a CDR-L3 of SEQ ID NO: 114.

6. The anti-c-Met/anti-Ang2 bispecific antibody of claim 5, wherein the anti-Ang2 antibody or antigen-binding fragment thereof comprises:

a heavy chain variable region comprising the amino acid sequence of SEQ ID NO: 160, 161, 162, 163, or 164, and a light chain variable region comprising the amino acid sequence of SEQ ID NO: 165, 166, 167, 168, 169, 170, or 171.

7. The anti-c-Met/anti-Ang2 bispecific antibody of claim 1, wherein the anti-c-Met antibody or antigen-binding fragment thereof comprises:

a heavy chain variable region comprising SEQ ID NO: 17, 74, 87, 90, 91, 92, 93, or 94; and a light chain variable region comprising SEQ ID NO: 196, 18, 19, 20, 21, 75, 88, 95, 96, 97, 98, 99, or 107.

8. A recombinant nucleic acid encoding the anti-c-Met/anti-Ang2 bispecific antibody of claim 1.

9. The recombinant nucleic acid of claim 8, wherein the recombinant nucleic acid is in an isolated vector.

10. The recombinant nucleic acid of claim 8, wherein the recombinant nucleic acid is in an isolated cell.

11. A method of preparing an anti-c-Met/anti-Ang2 bispecific antibody of claim 1 by expressing a nucleic acid encoding the anti-c-Met/anti-Ang2 bispecific antibody in a cell and isolating the bispecific antibody from the cell.

12. A method of treating a disease associated with overexpression of c-Met or Ang2 in a subject, comprising administering the anti-c-Met/anti-Ang2 bispecific antibody of claim 1 to the subject, wherein the disease associated with overexpression of c-Met or Ang2 is lung cancer, gastric cancer, or ovarian cancer.

13. The method of claim 12, further comprising administering Ang2 to the subject.

* * * * *